(12) United States Patent
Sundstrom

(10) Patent No.: US 7,270,975 B2
(45) Date of Patent: Sep. 18, 2007

(54) **METHODS FOR REGULATING BUD-HYPHA TRANSITIONS AND CAMP LEVELS IN *CANDIDA ALBICANS***

(75) Inventor: Paula Sundstrom, Lebanon, NH (US)

(73) Assignee: Trustees of Dartmouth College, Hanover, NH (US)

(*) Notice: Subject to any disclaimer, the term of this patent is extended or adjusted under 35 U.S.C. 154(b) by 767 days.

(21) Appl. No.: 10/672,074

(22) Filed: Sep. 29, 2003

(65) Prior Publication Data

US 2004/0120968 A1 Jun. 24, 2004

Related U.S. Application Data

(63) Continuation-in-part of application No. 09/801,774, filed on Mar. 9, 2001, now Pat. No. 6,706,688.

(51) Int. Cl.
*C12Q 1/44* (2006.01)
*C12N 9/16* (2006.01)

(52) U.S. Cl. .......................... 435/19; 435/21; 435/196; 536/23.2

(58) Field of Classification Search .................... 435/6, 435/19, 21, 196, 287.2; 536/23.2; 514/12
See application file for complete search history.

(56) References Cited

U.S. PATENT DOCUMENTS

| 5,627,153 | A | 5/1997 | Little, II et al. |
| 5,652,332 | A | 7/1997 | Little, II |
| 5,733,872 | A | 3/1998 | Little |
| 5,763,567 | A | 6/1998 | Little |
| 5,858,974 | A | 1/1999 | Little, II et al. |
| 5,863,762 | A | 1/1999 | Buratowski et al. |
| 2003/0104994 | A1 | 6/2003 | Sundstrom .................... 514/12 |

FOREIGN PATENT DOCUMENTS

| WO | WO 90/06997 | 6/1990 |
| WO | WO 92/15676 | 9/1992 |
| WO | WO 00/63442 | 10/2000 |

OTHER PUBLICATIONS

Alspaugh et al., 11 Genes & Development 3206-17 (1997).
Anderson and Soll, 132 J. Gen. Microbiol. 2035-47 (1986).
Anderson, 2 Hum. Gene Ther. 99-100 (1991).
Anderson, 256 Science 808-13 (1992).
Anderson et al., 6 Biotechniques 650-60 (1988).
Bahn et al., Sequence Alignment Report Accession #Q9Y873.
Barlow et al., 82 Pt. 2 J. Gen Microbiol. 261-72 (1974).
Barr et al., 254 Science 1507-9 (1991).
Baum and Perrimon, 10(16) Curr. Biol. 964-73 (2000).
Behr et al., 86 Proc. Natl. Acad. Sci. USA 6982-6 (1989).
Birse et al., 61 Infect. Immun. 3648-55 (1993).
Boeke et al., 197 Mol. Gen Genet. 345-6 (1984).
Brash et al., 7 Mol. Cell Biol. 2031-4 (1987).
Bruckmann et al., 146 Microbiol. 2755-64 (2000).
Caddick, Molecular Biology of Filamentous Fungi 141-52 (1992).
Calera et al., 67 Infect. Immun. 4280-4 (1999).
Calera et al., 68 Infect. Immun. 518-25 (2000).
Capecchi, 22 Cell 479-88 (1980).
Castilla et al., 10 Cell. Signal 713-19 (1998).
Cepko et al., 37 Cell 1053-62 (9184).
Chapman et al., 71 Circ. Res. 27-33 (1992).
Chattaway et al., 123 J. Gen. Microbiol. 233-40 (1981).
Chen et al., 20 Mol. Cell. Biol. 8696-708 (2000).
Cho et al., 30 J. Med. Vet. Mycol. 35-42 (1992).
Clapp et al., 78 Blood 1132-9 (1991).
Cox et al., 15(8) Yeast 703-13 (1999).
Csank et al., 8 Mol. Bio. Cell 2539-51 (1997).
Csank et al., 66 Infect. Immun. 2713-21 (1998).
Dabrowa et al., 13 Infect. Immun. 830-5 (1976).
Dai et al., 89 Proc. Natl. Acad. Sci. 10892-5 (1992).
DeRisi et al., 11(1) Curr. Opin. Oncol. 76-9 (1999).
Egidy et al., 13 Exp. Mycol. 428-32 (1989).
Fedor-Chaiken 61 Cell 329-40 (1990).
Felgner et al., 349 Nature 351-2 (1991).
Felgner et al., 84 Proc. Natl. Acad. Sci. USA 7413-7 (1987).
Feng et al., 181 J. Bacteriol. 6339-46 (1999).
Field et al., 61 Cell 319-27 (1990).
Fonzi et al., 134 Genetics 717-28 (1993).
Freeman et al., 16(2) Mol. Cell. Biol. 548-56 (1996).
Freeman et al., 270 J. Biol. Chem. 5680-5 (1995).
Fu et al., 4(11) Mol. Microbiol. 1847-52 (1990).
Fu et al., 7(5) Mol. Cell. Biol. 1691-6 (1987).
Gancedo, 25 FEMS Microbiol. Rev. 107-23 (2001).
Ghannoum et al., 63 Infect. Immun. 4528-30 (1995).
Gimeno et al., 68(6) Cell 1077-90 (1992).
Griffioen et al., 275 j. Biol. Chem. 1449-56 (2000).
Haas et al., 27(2) Curr. Genet. 150-8 (1995).
Hall et al., 17 EMBO J. 4370-8 (1998).
Hazen et al., 24 Infect. Immun. 661-6 (1979).
Higgins & Sharp, 73 Gene 237-44 (1988).
Hilberg et al., 84 Proc. Natl. Acad. Sci. USA 5232-6 (1987).
Holland et al., 84 Proc. Natl. Acad. Sci. USA 8662-6 (1987).
Holmes et al., 133 J. Gen. Microbiol. 3219-28 (1987).
Houghten et al., 354 Nature 84-6 (1991).
Huang et al., 27(2 Pt. 1) Cell 245-55 (1981).
Iyer et al., 283(5398) Science 83-7 (1999).
Jeme et al., 1 EMBO 234 (1982).
Jeme, 125 Ann. Immunol. 373 (1974).
Johnston, 346 Nature 776-7 (1990).
Kawamukai et al., 3 Mol. Biol. Cell. 167-80 (1992).
Kimura and Pearsall, 21 Infect. Immun. 64-8 (1978).

(Continued)

*Primary Examiner*—Tekchand Saidha
(74) *Attorney, Agent, or Firm*—Licata & Tyrrell P.C.

(57) ABSTRACT

The infection of a mammalian host by a microorganism can be prevented or treated through the alteration of the *C. albicans* homologue of the high affinity phosphodiesterase, PDE2, gene and/or the adenylate cyclase-associated protein gene. These methods may be used in the identification, prevention or treatment of microbial infection of mammalian hosts such as immunocompromised or immunosuppressed humans, for example, those having AIDS or undergoing transplantation or anti-cancer therapy.

30 Claims, 25 Drawing Sheets

OTHER PUBLICATIONS

Kinsman et al., 31 Mycoses 617-26 (1988).
Kohler and Fink, 93 Proc. Natl. Acad. Sci. USA 13223-8 (1996).
Kohler et al., 6 Eur. J. Immunol. 511-19 (1976).
Kohler et al., 256 Nature 495-97 (1975).
Kronstad et al., 170 Arch. Microbiol. 395-404 (1998).
Kronstad et al., 73 Suppl. 1 Can. j. Bot. S258-65 (1995).
Kübler et al., 272 J. Biol. Chem. 20321-3 (1997).
Kudla et al., 9(5) EMBO J. 1355-64 (1990).
Kalkarni et al., 5 Exp. Mycol. 148-54 (1981).
Kurtz et al., 6 Mol. Cell. Biol. 142-9 (1986).
Lam et al., 354 Nature 82-4 (1991).
Lambrechts et al., 93 Proc. Natl. Acad. Sci. USA 8419-24 (1996).
Land et al., 11(5) Infect. Immun. 1014-23 (1975).
Larrick et al., Gene Therapy. Application of Molecular Biology 71-104 (Elsevier Science Publishing Co., Inc.) (1991).
Leberer et al., 7 Curr. Biol. 539-46 (1997).
Leclerc et al., 90 J. Clin. Invest. 936-44 (1992).
Lengeler et al., 64 Microbiol. Mol. Biol. Rev. 746-85 (2000).
Lila and Drubin, 8 Mol. Biol. Cell. 367-85 (1997).
Lim et al., 83 Circulation 2007-11 (1991).
Lo and Dranginis, 9 Mol. Biol. Cell. 161-71 (1998).
Lo et al., 90 Cell 939-49 (1997).
Loeb et al., 19 Mol. Cell. Biol. 4019-27 (1999).
Loeffler et al., 54 J. Neurochem. 1812-5 (1990).
Lorenz and Heitman 16 EMBO J. 7008-18 (1997).
Lorenz et al., 154 Genetics 609-22 (2000).
Lynch et al., 89 Proc. Natl. Acad. Sci. USA 1138-42 (1992).
Marzluf, 61(1) Microbiol. Mol. Biol. Rev. 17-21 (1997).
Matviw et al., 12 Mol. Cell. Biol. 5033-40 (1992).
Miller et al. in Hybridomas in Cancer Diagnosis and Therapy 134 (1982).
Miller, 357 Nature 455-60 (1992).
Miller, 76 Blood 271-8 (1990).
Minehart et al., 11(12) Mol. Cell. Biol. 6216-28 (1991).
Mösch and Fink, 145 Genetics 671-84 (1997).
Mösch et al., 10 Mol. Biol. Cell. 1325-35 (1999).
Nabel et al., 244 Science 1342-4 (1989).
Niimi et al., 142 J. Bacteriol. 1010-4 (1980).
Niimi, 20 Fungal Genet. Biol. 79-83 (1996).
Palmer et al., 88 Proc. Natl. Acad. Sci. USA 1330-34 (1991).
Quantin et al., 89 Proc. Natl. Acad. Sci. USA 2581-4 (1992).
Reimann et al., 89 J. Immunol. Meth. 93-101 (1986).
Roemer et al., 208 Eur. J. Biochem. 211-25 (1992).
Roman et al., 18 Som. Cell Mol. Gen. 247-58 (1992).
Rupp et al., 18 EMBO J. 1257-69 (1999).
Schaller et al., 34 Mol. Microbiol. 169-80 (1999).
Scharfmann et al., 88 Proc. Natl. Acad. Sci. USA 4626-30 (1991).
Schweizer et al., 38 Mol. Microbiol. 435-45 (2000).
Selden et al., 317 New Eng. J. Med. 1067-76 (1987).
Sobel et al., 44 Infect. Immun. 576-80 (1984).
Songyang et al., 72 Cell 767-78 (1993).
Staab et al., 271 J. Biol. Chem. 6298-305 (1996).
Staab et al., 283 Science 1535-38 (1999).
Staib et al., 97 Proc. Natl. Acad. Sci. USA 6102-7 (2000).
Stewart et al., 46(2-3) Gene 291-5 (1986).
Straus, The Adenovirus 451-96 (H.S. Ginsberg, ed., Plenum Press) (1984).
Sundstrom et al., 174 J. Bacteriol. 6789-99 (1992).
Temin, Retrovirus vectors for gene transfer, in Gene Transfer 149-87 (Kucherlapati, ed., Plenum) (1986).
Terrell, 74 Mayo Clin. Proc. 78-100 (1999).
Toda et al., 40 Cell 27-36 (1985).
Valerio et al., 84 Gene 419-27 (1989).
Vojtek and Cooper, 105 J. Cell. Sci. 777-85 (1993).
Wolff et al., 247 Science 1465-8 (1990).
Yamada-Okabe et al., 181 J. Bacteriol. 7243-7 (1999).
Yanagita, 26 Arch. Microbiol. 329-44 (1957).
Yu, et al., 274 J. Biol. Chem. 19985-91 (1999).
Zhang et al., Mol. Microbiol. 36(3) 618-29 (2000).
Zelada et al., 42 Cell. Mol. Biol. (Noisy-le-grand) 567-76 (1996).
Zelicof et al., 271 J. Biol. Chem. 18243-52 (1996).
Jung et al., "The cAMP phosphodiesterase encoded by CaPDE2 is required for hyphal development in *Candida albicans*", Microbiology 2003 149:2961-2976.

| Strain | Genotype | Parent Strain | References |
|---|---|---|---|
| SC5314 | Wild type | | Gillum et al., 198 MOL. GEN. GENET. 179-82 (1984) |
| CAI4 | Δura3::imm434/Δura3::imm434 | SC5314 | Fonzi et al., 134 GENETICS 717-28 (1993) |
| *UnoPP-1 | Δura3::imm434/Δura3::imm434 Δeno1::URA3/ENO1 | CAI4 | Postlethwait et al., 177 J. BACTERIOL. 1772-9 (1995) |
| CAC1 | Δura3::imm434/Δura3::imm434 CAP1/cap1::hisG-URA3-hisG | CAI4 | This study |
| CAC1-1 | Δura3::imm434/Δura3::imm434 CAP1/cap1::hisG | CAC1 | This study |
| CAC1-1A | Δura3::imm434/Δura3::imm434 CAP1/cap1::hisG-URA3-hisG | CAC1-1 | This study |
| CAC1-1A1 | Δura3::imm434/Δura3::imm434 CAP1/cap1::hisG/cap1::hisG | CAC1-1A | This study |
| CACRE1 | Δura3::imm434/Δura3::imm434 CAP1/cap1::hisG ENO1/eno13 | CAC1-1A1 | This study |

*a CAI4 derivative made Ura+ by disruption of an enolase gene with URA3

```
                  RLE/RLE MOTIF
CaCAP1      1   MSTEESQFNVQGYNIITILKRLEAATSRLEDITIFQEEANKNHYGVDSLTEKGTPKSRTVESSEATSDGKSLESTSFATFSEAPV        85
ScCAP1      1   MPDSKYTMQGYNLVKLLKRLEEATARLEDVTIYQEGYIQNKLEAS---KNNKP------SDSGADANTTNEPSAENAPEVEQ        73
SpCAP1      1   MSDMINIRETGYNFTTILKRLEAATSRLEDLVESGHKPLPNMHRPSR-DSNSQTHNISFNIGTPTAPTVSTGSPAVASLHDQVA       83
MouseCAP1   1   MADMQNLVERLERAVGRLEAVSHTSDMH----------------------------------CGYGDSPS-------------K       37
HumanCAP1   1   MADMQNLVERLERAVGRLEAVSHTSDMH----------------------------------RGYADSPSK------------A       38

CaCAP1     86   EKS---------------KLIVEFENFVESYVHPLVETSKKIDSLVGESAQYFYEAFVEQGKFLELVLQSQQPDMTDPALAKA      153
ScCAP1     74   DP----------------KCITAFQSYIGENIDPLVELSGKIDTVVLDALQLLKGGFQSQLTFLRAAVRSRKPDYSSQTFADS      140
SpCAP1     84   AAISPRNRSLTSTSAVEAVPASISAYDEFCSKYLSKYMELSKKIGGLIAEQSEHVEKAFNLLRQVLSVALKAQKPDMDSPELLEF    168
MouseCAP1  38   GAV---------------PYVQAFDSLLANPVAEYLKMSKEIGGDVQKHAEMVHTGLKLERALLATASQCQQP--AGNKLSDL    103
HumanCAP1  39   GAA---------------PYVQAFDSLLAGPVAEYLKISKEIGGDVQKHAEMVHTGLKLERALLVTASQCQQP--AENKLSDL    104

CaCAP1    154   LEPMNAKCTKINELKDSNRKSPFFNHLSTFSESNAVFYWIGIP-TPVSYITDTKDTVKFWSDRVLKEYKTKDQVHVEWVKQTLSV    237
ScCAP1    141   LRPINENIIKLGQLKESNRQSKYFAYLSALSEGAPLFSWVAVD-TPVSMVTDFKDAAQFWTNRILKEYRESDPNAVEWVKKFLAS    224
SpCAP1    169   LKPIQSELLTITNIRDEHRTAPEFNQLSTVMSGISILGWVTVEPTPLSFMSEMKDSSQFYANRVMKEFKGKDDLQIEWVRSYLTL    253
MouseCAP1 104   LAPISEQIQEVITFREKNRGSKFFNHLSAVSESIQALGWVALAAKPGFVKEMNDAAMFYTNRVLKEYRDVDKKHVDWVRAYLSI    188
HumanCAP1 105   LAPISEQIKEVITFREKNRGSKLFNHLSAVSESIQALGWVAMAPKPGYVKEMNDAAMFYTNRVLKEYKDVDKKHVDWVKAYLSI    189

POLYPROLINE REGION
CaCAP1    238   FDELKNYVKEYHTTGVAWNPKGKPFAEVVSQQTESAAKNSS-SASGSAGGAAPPPPPPATFFDDTEKDSENPSPAS-GGINA     320
ScCAP1    225   FDNLKAYIKEYHTTGVSWKKDGMDFADAMAQSTKNTGATSSPSPASATAAPAPPPPAPPASVFEISNDTPATSSDANKGGIGA    309
SpCAP1    254   LTELITYVKTHFKTGLTWSTKQDAVPLKTALANLSASKTQAPSSGDSANGGLPPPPPPPPPSNDFWKDSNEP-APADNK-GDMGA  336
MouseCAP1 189   WTELQAYIKEFHTTGLAWSKTG------------------------PVAKELSGLPSGPSVGSGPPPPPPGPPPPIPTS-----SGSDDS-ASRSA   255
HumanCAP1 190   WTELQAYIKEFHTTGLAWSKTG------------------------PVAKELSGLPSGPSAGSGPPPPPPGPPPPPVSTS-----SGSDES-ASRSA  256

SH3 BINDING MOTIFS
CaCAP1    321   VFAELNQGANITSGLKKVDKSEMTHKNPELRKQPPVAPK--KPAPPKKPSSLSGG-VSSAPVKKPAKKELIDGTKWIIQNFTKAD    402
ScCAP1    310   VFAELNQGENITKGLKKVDKSQQTHKNPELRQSSTVSSTGSKSGPPPRK--KP---STLKTKRPPRKELVG-NKWFIENYEN--   386
SpCAP1    337   VFAEINKGEGITSGLRKVDKSEMTHKNPNLR------KTGPTPGPKPKIKSSAPSKPAETAPVKPPRIELEN-TKWFVENQVD-- 412
MouseCAP1 256   LFAQINQGESITHALKHVSDDMKTHKNPALKAQSGPVRSGPKPFSAPKPQ-TSPS-PKPATKKEPALLELEG-KKWRVENQEN-- 335
HumanCAP1 257   LFAQINQGESITHALKHVSDDMKTHKNPALKAQSGPVRSGPKPFSAPKPQ-TSPS-PKRATKKEPAVLELEG-KKWRVENQEN-- 336
```

FIG. 3A

```
CaCAP1      403  ISDLSPITIEVEMHQSVFIGNCSDVTIQLKGKANAVSVSETKNVALVIDSLISGVDVIKSYKFGIQVLGLVPMLSIDKSDEGTIY  487
ScCAP1      387  --ETESLVIDANKDESIFIGKCSQVLVQIKGKVNAISLSETESCSVVLDSSISGMDVIKSNKFGIQVNHSLPQISIDKSDGGNIY  469
SpCAP1      413  --NHSIVLDSVELNHSVQIFGCSNCTIIIKGKLNTVSMSNCKRTSVVVDTLVAAFDIAKCSNFGCQVMNHVPMIVIDQCDGGSIY  495
MouseCAP1   336  --VSNLVIDDTELKQVAYIYKCVNTTLQIKGKINSITVDNCKKLGLVFDDVVGIVEIINSRDVKVQVMGKVPTISINKTDGCHAY  418
HumanCAP1   337  --VSNLVIEDTELKQVAYIYKCVNTTLQIKGKINSITVDNCKKLGLVFDDVVGIVEIINSKDVKVQVMGKVPTISINKTDGCHAY  419

CaCAP1      488  LSQESIDNDSQVFTSSTTALNINAPK-ENDDYEELAVPEQFVSKVVN-GKLVTQIVEHAG   545
ScCAP1      470  LSKESLN--TEIYTSCSTAINVNLPIGEDDDYVEFPIPEQMKHSFAD-GKFKSAVFEHAG   526
SpCAP1      496  LSKSSLS--SEVVTSKSTSLNINVPN-EEGDYAERAVPEQIKHKVNEKGELVSEIVRHE   551
MouseCAP1   419  LSKNSLD--CEIVSAKSSEMNVLIPT-EGGDFNEFPVPEQFKTLWNG-QKLVTTVTEIAG   474
HumanCAP1   420  LSKNSLD--CEIVSAKSSEMNVLIPT-EGGDFNEFPVPEQFKTLWNG-QKLVTTVTEIAG   475
```

FIG. 3B

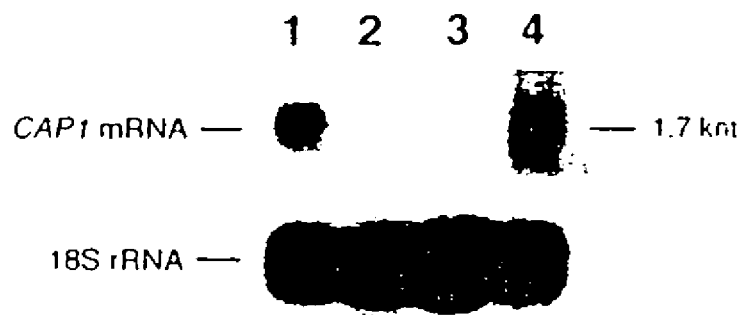
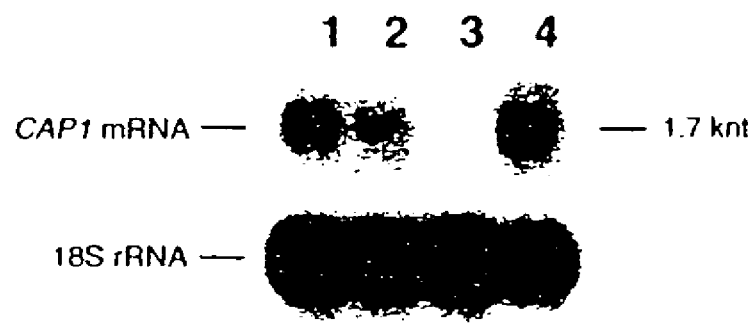
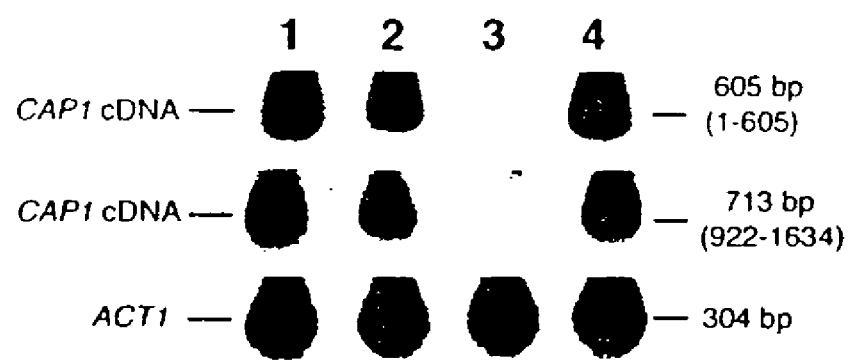
Figure 4

| Strains | Doubling Time (hour)* | | | | | |
|---|---|---|---|---|---|---|
| | Rich media (YPD) | | | Minimal media (YNB) | | |
| | 27°C | 30°C | 37°C | 27°C | 30°C | 37°C |
| UnoPP-1 | 2.2 | 1.6 | 2.0 | 2.9 | 2.9 | 3.0 |
| CAC1 | 2.2 | 1.7 | 2.0 | 2.9 | 2.9 | 3.0 |
| CAC1-1A | 2.3 | 1.7 | 2.2 | 3.9 | 3.7 | 3.8 |
| CACRE1 | 2.2 | 1.7 | 2.1 | 2.8 | 2.9 | 2.9 |

*Mean value from two independent experiments that differed by less than 20%

Figure 5

A
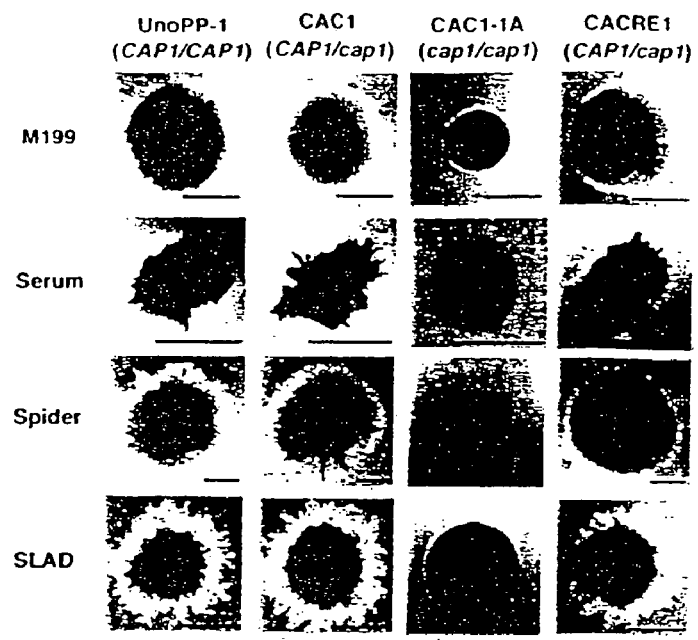
B
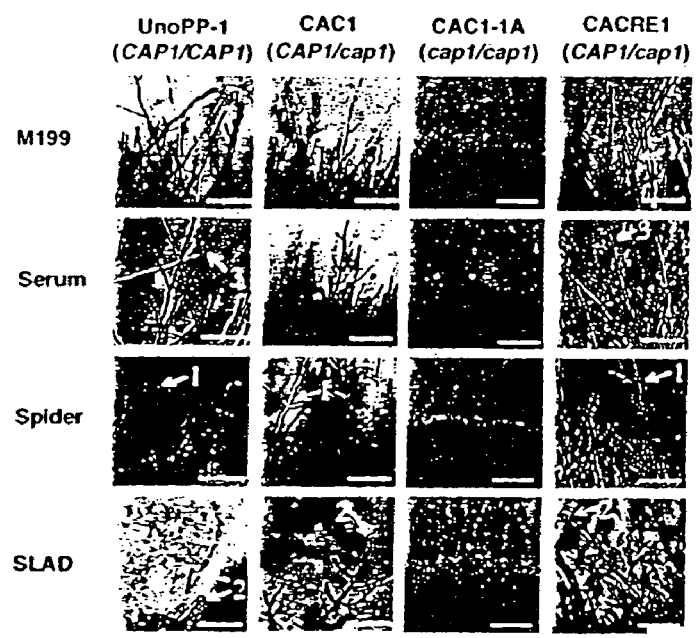
Figure 7

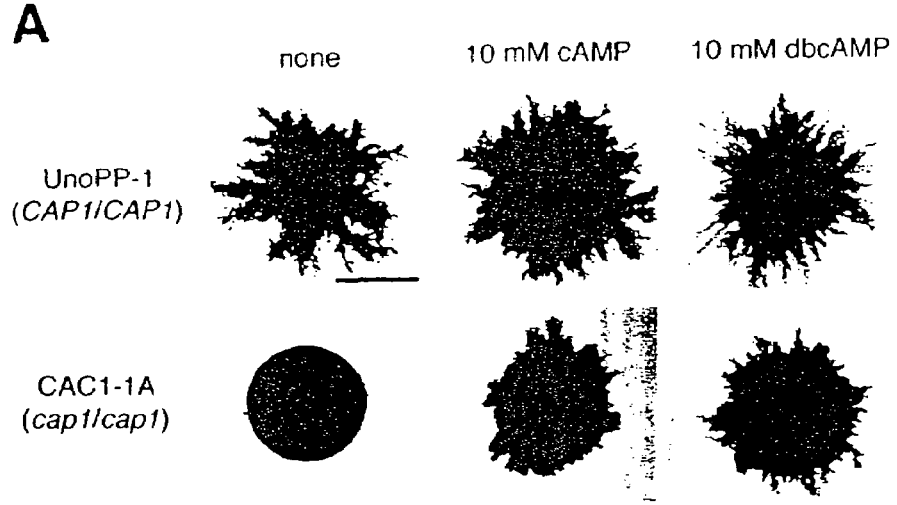
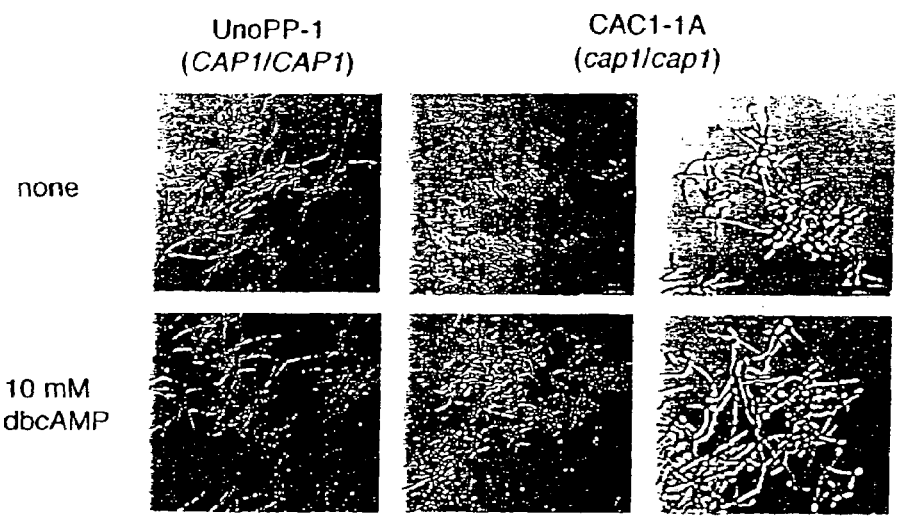
Figure 9

| Strain | Genotype | Parent Strain | References |
|---|---|---|---|
| SC5314 | Wild type | | (Gillum et al., 1984) |
| CAI4 | Δura3::imm434/Δura3::imm434 | SC5314 | (Fonzi and Irwin, 1993) |
| UnoPP-1 | As CAI4, but Δeno1::URA3/ENO1 | CAI4 | (Postlethwait and Sundstrom, 1995) |
| CAC1-1A | As CAI4, but cap1::hisG/cap1::hisG-URA3-hisG | CAC1-1 | (Bahn and Sundstrom, 2001) |
| CAC1-1A1 | As CAI4, but cap1::hisG/cap1::hisG | CAC1-1A | (Bahn and Sundstrom, 2001) |
| CAC1-1A1E1 | As CAC1-1A1, but Δeno1::URA3/ENO1 | CAC1-1A1 | This study |
| BPS1 | As CAI4, but PDE2/pde2::hisG-URA3-hisG | CAI4 | This study |
| BPS2 | As CAI4, but PDE2/pde2::hisG | BPS1 | This study |
| BPS3 | As CAI4, but pde2::hisG-URA3-hisG/pde2::hisG | BPS2 | This study |
| BPS4 | As CAI4, but pde2::hisG-URA3-hisG/pde2::hisG | BPS2 | This study |
| BPS7 | As CAI4, but pde2::hisG/pde2::hisG | BPS4 | This study |
| BPS13 | As BPS2, but Δeno1::URA3/ENO1 | BPS2 | This study |
| BPS15 | As BPS7, but Δeno1::URA3/ENO1 | BPS7 | This study |
| BPS9 (revertant) | As CAI4, but PDE2/pde2::hisG Δeno1::URA3/ENO1 | BPS7 | This study |
| BPS10 (revertant) | As CAI4, but PDE2/PDE2 Δeno1::URA3/ENO1 | BPS7 | This study |
| BPS11 (revertant) | As CAI4, but PDE2/PDE2 Δeno1::URA3/ENO1 | BPS7 | This study |
| BPS16 | As CAC1-1A1, but PDE2/pde2::hisG-URA3-hisG | CAC1-1A1 | This study |
| BPS17 | As CAC1-1A1, but PDE2/pde2::hisG | BPS16 | This study |
| BPS18 | As CAC1-1A1, but pde2::hisG-URA3-hisG/pde2::hisG | BPS17 | This study |
| BPS19 | As CAC1-1A1, but pde2::hisG-URA3-hisG/pde2::hisG | BPS17 | This study |
| BPS20 | As CAC1-1A1, but pde2::hisG/pde2::hisG | BPS18 | This study |
| BPS24 | As BPS17, but Δeno1::URA3/ENO1 | BPS17 | This study |
| BPS27 | As BPS20, but Δeno1::URA3/ENO1 | BPS20 | This study |
| BPS22 (revertant) | As CAC1-1A1, but PDE2/pde2::hisG Δeno1::URA3/ENO1 | BPS20 | This study |
| EGFP3 | As CAI4, but Δeno1::ENOp-GFP-URA3/ENO1 | CAI4 | (Staab et al., unpublished) |
| EPDE2-3 | As CAI4, but Δeno1::ENOp-PDE2-URA3/ENO1 | CAI4 | This study |

Figure 12

```
CaPDE2    335  NPIQTLGLLVAALGHDVGHPGTTNDFMIKFSAPTALLY  372
ScPDE2    288  NPVQTLLLCMAAIGHDVGHPGTNNQLLCNCESEVAQNF  325
HuPDE2A3  682  EDIEIFALFISCMCHDLDHRGTNNSFQVASKSVLAALY  719

CaPDE2    373  NDR-SVLESYHASLFINKVLRICWPDLLTCTIEEKSEL  409
ScPDE2    326  KNV-SILENFHRELFQ-QLLSEHWP--LKLSISKKK--  357
HuPDE2A3  720  SSEGSVMERHHFAQAI-AILNTHGCN-IFDHFSRKDYQ  755

CaPDE2    410  TIRSLIISSILATDMGEHNEYVNRLKSFKTHNEILNHD  447
ScPDE2    358  --FDFISEAILATDMALHSQYEDRLMHENPMKQIT---  390
HuPDE2A3  756  RMLDLMRDIILATDLAHHLRIFKDLQKMAEVGYDRNNK  793

CaPDE2    448  NTVKLISALLIKCADISNVTRPLRVSAQWAMVLSREF   484
ScPDE2    391  ----LISLIIKAADISNVTRTLSISARWAYLITLEF   422
HuPDE2A3  794  QHHRLLLCLLMTSCDLSDQTKGWKTTRKIAELIYKEF   830
```

FIG. 13

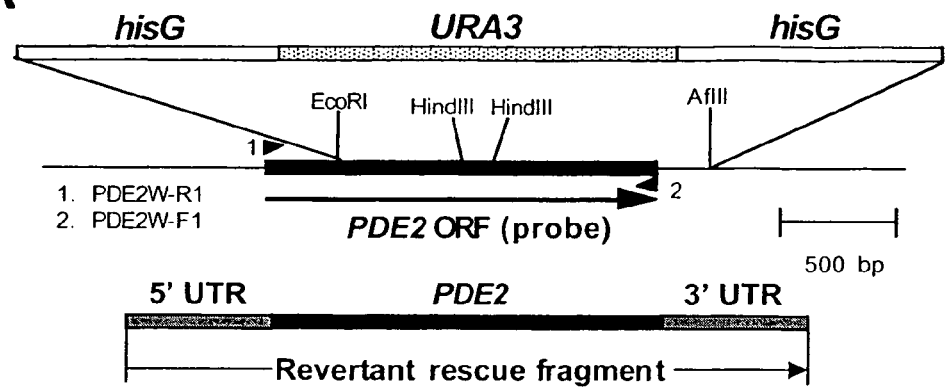
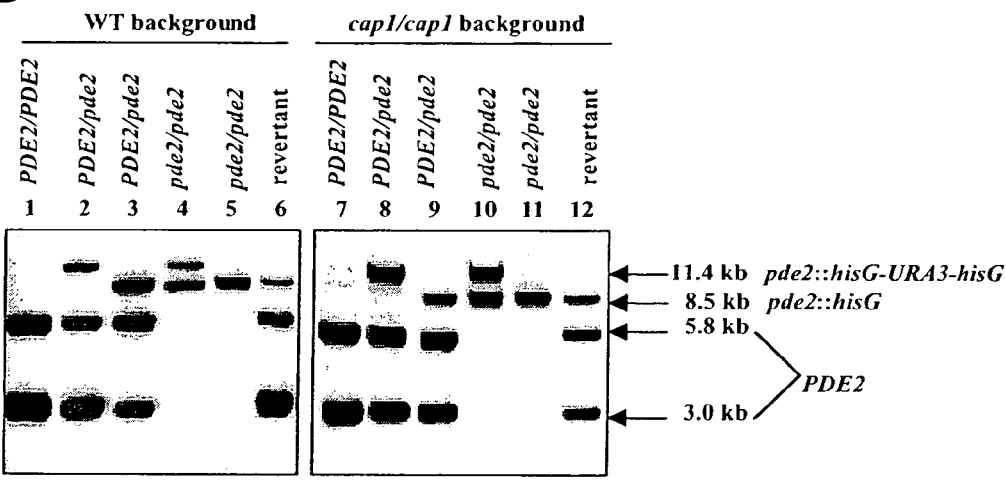
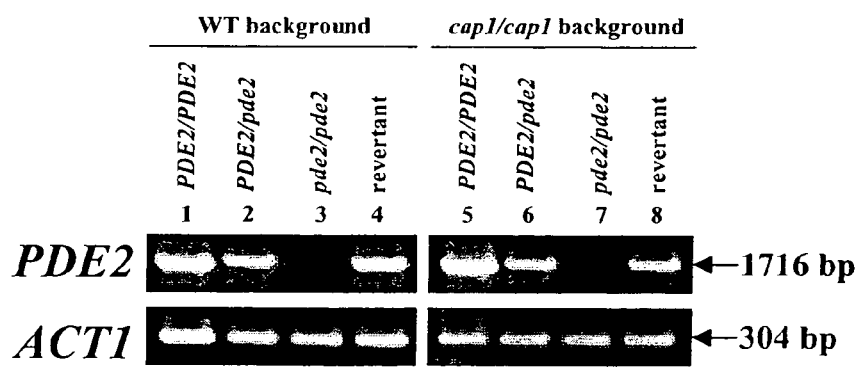
Figure 14

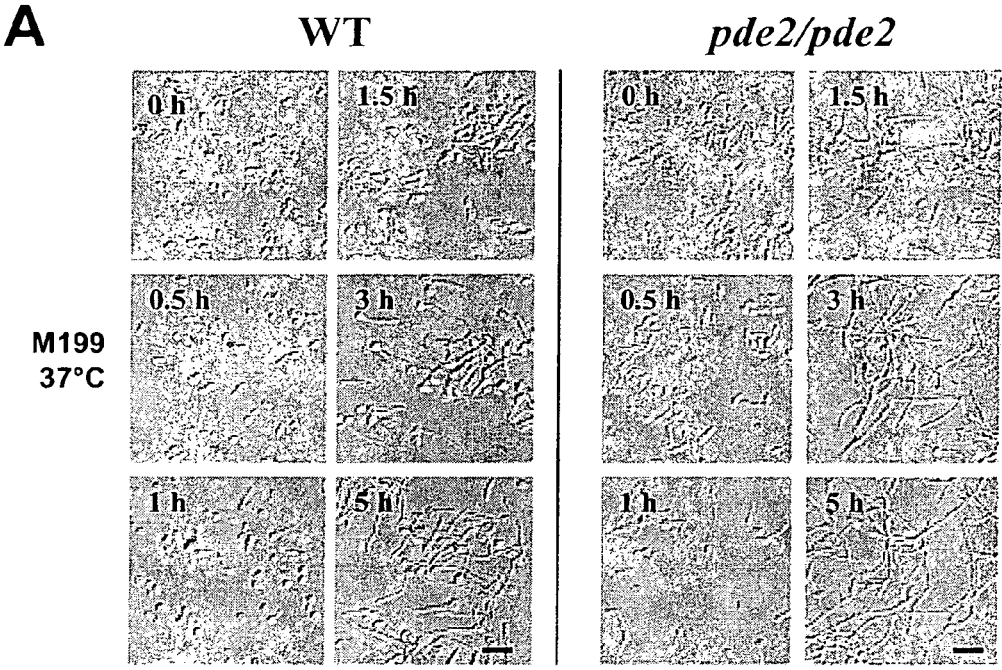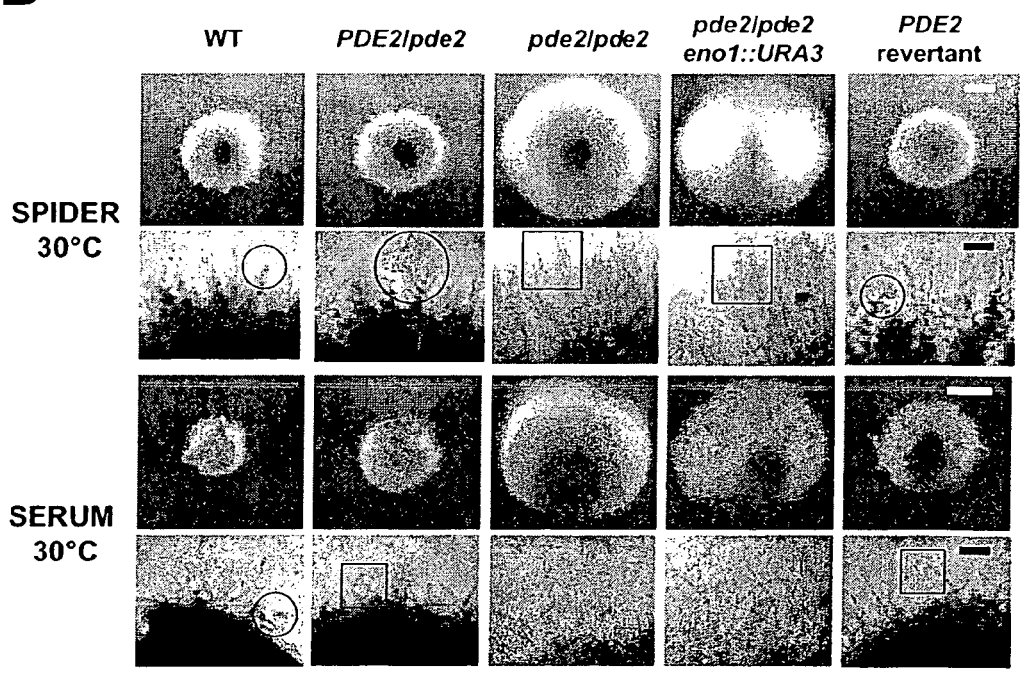
Figure 16

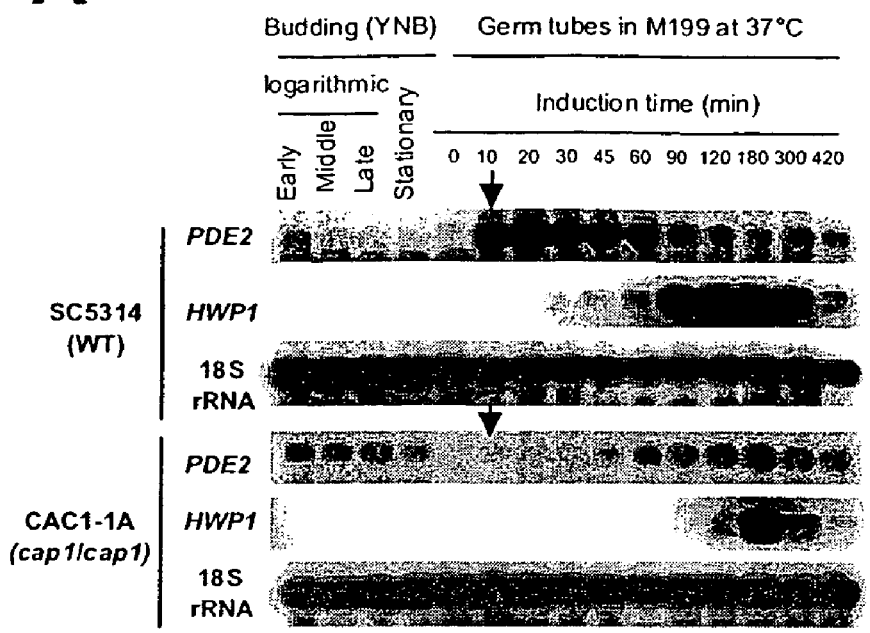
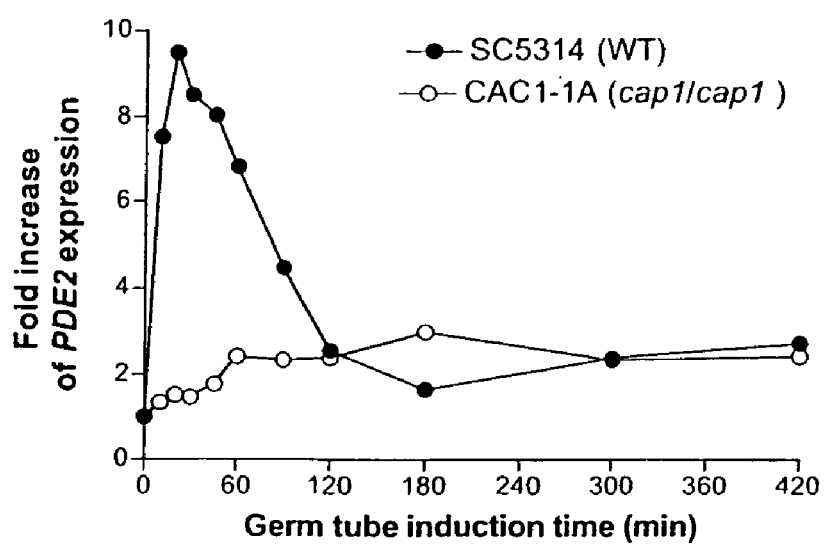
Figure 21

METHODS FOR REGULATING BUD-HYPHA TRANSITIONS AND CAMP LEVELS IN *CANDIDA ALBICANS*

CROSS REFERENCE

This application is a continuation-in-part of application Ser. No. 09/801,774, now U.S. Pat. No. 6,706,688, filed 9 Mar. 2001, for Methods for Regulating Bud-Hypha Transitions and cAMP Levels by the Adenylate Cyclase-Associated Protein Gene, CAP1, which is expressly incorporated fully herein by reference.

STATEMENT REGARDING FEDERALLY SPONSORED RESEARCH

This invention was made, at least in part, with US government support under grant numbers 2R01DE011375 and 5R01AI046608, awarded by NIH. The US government may have certain rights in the invention.

FIELD OF THE INVENTION

The present invention relates to methodologies and molecular targets for the prevention and treatment of microbial infection of a mammalian host through the alteration of the *Candida albicans* homologue of the high affinity phosphodiesterase gene (PDE2) alone or with the *C. albicans* homologue of the adenylate cyclase-associated protein (CAP1) gene. Preferably, these methods and molecular targets may be used in the prevention and treatment of microbial infection of mammalian hosts such as immunocompromised patients at risk for opportunistic fungal infections, organ transplant patients, cancer patients undergoing chemotherapy, burn patients, AIDS patients, and patients with diabetic ketoacidosis.

BACKGROUND OF THE INVENTION

Whether pathogenic or opportunistic, microorganisms have evolved numerous mechanisms to facilitate their establishment and proliferation in mammalian hosts. During initial infection, the interaction of a microorganism with its mammalian host can include attachment or adhesion to the host cell surface, and invasion of host cells, for example. In certain instances, this interaction can be nonspecific. In others, such microbial interaction involves the specific binding of the microorganism to a particular receptor or receptor complex expressed on the host cell surface. In turn, the binding event can trigger changes in the microorganism and/or the mammalian host cell, leading to the progression of infection.

*Candida* is an ubiquitous yeast recognized as the causative agent of candidiasis (*Candida* mycosis). At least 90% of the disorders are caused by the species in normal individuals. However, destabilization of the host-parasite equilibrium upon inopportune loss or deficiencies in protective innate and immune deterrents favors overgrowth of the common gastrointestinal tract denizen and opportunistic pathogen, *C. albicans*. Acquired immunodeficiency syndrome (AIDS) or iatrogenic immunosuppression are risk factors for oropharyngeal and esophageal candidiasis (Hood et al., 28 CLIN. INFECT. DIS. 587-96 (1999)). Thus, oropharyngeal and esophageal candidiasis are among the most frequent opportunistic fungal infections observed in human immunodeficiency virus positive (HIV+) and AIDS patients, occurring in the majority of patients. Candidal infections increase in severity and recur more frequently as the immunodeficiency progresses. The current status of the AIDS epidemic is one of increasing numbers of individuals infected and no cure. Many infected individuals may live for a long time with HIV in an essentially permanent immunocompromised state. Because of the loss of the cellular component of the immune system, AIDS patients are susceptible to invasion of submucosal tissue by *C. albicans*. In addition to HIV infected patients, oral candidiasis occurs in patients with leukemia or other cancers, as well as in patients with other underlying diseases. Prematurely-born infants are also at risk and may acquire mucosal infections causing permanent sequelae (Huang et al., 30 SCAND. J. INFECT. DIS. 137-42 (1998); Sood et al., 41 MYCOSES 417-9 (1998)). Candidiasis in denture wearers, or denture stomatitis, is the most common of all *C. albicans* associated diseases.

Although *C. albicans* is sensitive to antifungal drugs, treatment over long periods of time is required. At present, the treatment for invasive infections is based on relatively few antimycotics. Nystatin, ketoconazole, and amphotericin B are drugs, which are used to treat oral and systemic *Candida* infections. However, orally administered nystatin is limited to treatment within the gut and is not applicable to systemic treatment. Some systemic infections are susceptible to treatment with ketoconazole or amphotericin B, but these drugs may not be effective in such treatment unless combined with additional drugs. Amphotericin B has a relatively narrow therapeutic index and numerous undesirable side effects and toxicities occur even at therapeutic concentrations. While ketoconazole and other azole antifungals exhibit significantly lower toxicity, their mechanism of action, inactivation of cytochrome $P_{450}$ prosthetic group in certain enzymes (some of which are found in humans), precludes use in patients that are simultaneously receiving other drugs that are metabolized by the body's cytochrome $P_{450}$ enzymes. See, e.g., U.S. Pat. No. 5,863,762.

Other known antifungal agents include: polyene derivatives, such as amphotericin B (including lipid or liposomal formulations thereof) and the structurally related compounds nystatin and pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer, Groton, Conn.] and SCH56592 [Schering-Plough, Kenilworth, N.J.]); allylamines-thiocarbamates (including tolnaftate, naftifine and terbinafine); griseofulvin; ciclopirox; haloprogin; echinocandins (including MK-0991 [Merck, Whitehouse Station, N.J.]); nikkomycins; and bactericidal/permeability-increasing protein (BPI), as described in U.S. Pat. Nos. 5,627,153; 5,858,974; 5,652,332; 5,763,567; and 5,733,872. Unfortunately, antimycotics cause serious, sometimes different, side effects, such as renal insufficiency, hypocalcemia and anemia, as well as unpleasant constitutional symptoms such as fever, shivering and low blood pressure.

The frequency of candidal infections may be a result of the prophylactic use of antibacterial drugs used in AIDS patients to minimize other opportunistic infections. Emergence of drug-resistant isolates and the limited selection of antifungal drugs point to the need for research aimed at identifying new anti-fungal targets (Terrell, 74 MAYO CLIN. PROC. 78-100 (1999)). However, the pathogenesis is complex and is thought to involve multiple host factors that include loss of cell mediated immunity and altered phagocytic cell activity. High frequencies of nosocomial candidemia reflect the ability of *C. albicans* to translocate across the gastrointestinal tract, disrupting internal tissues in debilitated patients (Viscoli et al., 28 CLIN. INFECT. DIS. 1071-9 (1999)).

Thus far, studies have shown that development of candidiasis is a multi-stage process requiring sensing environmental conditions and transducing signals to regulate expression of appropriate genes at balanced levels in *C. albicans*. Filamentous growth of *C. albicans* includes not only pseudohyphal, elongated yeast-like forms described for *Saccharomyces cerevisiae*, but true hyphae as well. Compared to most pathogenic fungi, the morphological response of *C. albicans* to environmental conditions is rapid. Germ tubes are produced within one hour of placing cells in appropriate conditions. The mechanisms employed by *C. albicans* to achieve this apparently advantageous spectrum of growth morphologies and optimized metabolic activities are poorly understood.

A feature of *C. albicans* growth that is correlated with pathogenicity in the oral cavity is the ability to transform from budding to filament-extending growth. Filamentous forms adhere more readily to buccal epithelial cells than budding yeasts, and histologically are a prominent feature of invasion of the mucosa. In mucosal disease, filamentous forms, particularly true hyphae, invade the keratinized layer of differentiated, stratified squamous epithelium. True hyphae are septate, cylindrical structures with parallel sides that are formed by extension of germ tubes that emerge from yeasts in appropriate environmental conditions.

The relative contribution of yeast and filamentous forms to the pathogenesis of candidiasis is an unresolved issue. However, mutants that do not produce hyphae in vitro have reduced virulence in animal models (Ghannoum et al., 63 INFECT. IMMUN. 4528-30 (1995); Lo et al., 90 CELL 939-49 (1997); Sobel et al., 44 INFECT. IMMUN. 576-80 (1984)). Expression of hypha-specific virulence factors such as the hyphal wall protein (HWP1) adhesin gene (Staab et al., 283 SCIENCE 1535-38 (1999); Staab et al., 271 J. BIOL. CHEM. 6298-305 (1996)) and secreted aspartyl proteinase (SAP) genes (Schaller et al., 34 MOL. MICROBIOL. 169-80 (1999); Staab et al., 97 PROC. NATL. ACAD. SCI. USA 6102-7 (2000)) are correlated with the virulence of hyphal forms. Research into the mechanisms that lead to the production of these virulence factors is important for developing strategies to interfere with candidiasis.

Thus, an alternative method to the prevention and treatment of candidiasis may be approached via disruption of molecular events that transform *C. albicans* to the pathogenic filamentous form. In many pathogenic fungi, interconversions between morphological growth forms, particularly between yeast growth and filamentous growth, coincide with adaptation to a host environment followed by tissue destruction. Morphological transitions are accompanied by expression of virulence attributes for many pathogenic fungi. A central pathway that regulates these transitions is the conserved cyclic AMP (cAMP)/protein kinase A (PKA) signaling pathway, which modulates yeast and pseudohyphal growth of the model non-pathogenic yeast, *Saccharomyces cerevisiae* (D'Souza and Heitman, 25 FEMS MICROBIOL. REV. 349-364 (2001); Kronstad et al., 170 ARCH. MICROBIOL. 395-404 (1998); and Lengeler et al., 64 MICROBIOL. MOL. BIOL. REV. 746-785 (2000)). In response to specific environmental cues, *S. cerevisiae* transmits signals to the adenylate cyclase complex through a GTP-binding protein (G protein, Gpa2 and Gpb1/Gpb2) associated with a G protein-coupled receptor (Gpr1) or small G protein such as Ras (Gimeno et al., 68 CELL 1077-1090 (1992); Harashima and Heitman, 10 MOL. CELL BIOL. 163-173 (2002); Kübler et al., 272 J. BIOL. CHEM. 20321-20323 (1997); Lorenz et al., 154 GENETICS 609-622 (2000)). The adenylate cyclase complex of *S. cerevisiae* produces cAMP and is composed of adenylate cyclase (Cyr1) (Matsumoto et al., 79 PROC. NAT. ACAD. SCI. 2355-2359 (1982) and the adenylate cyclase-associated protein (CAP/Srv2)(Fedor-Chaiken et al., 61 CELL 329-340 (1990); and Gerst et al., 11 MOL. CELL BIOL. 1248-1257 (1991)). cAMP binds to the regulatory subunit (Bcy1/Sra1) of PKA (Cannon and Tatchell, 7 MOL. CELL BIOL. 2653-2663 (1987); Kunisawa et al., 15 NUCL. ACIDS RES. 368-369 (1987)), releasing the active catalytic subunits Tpk1, Tpk2, and Tpk3 from PKA. Although these catalytic subunits are functionally redundant in many cellular processes, Tpk2 is a positive regulator of filamentous growth, whereas Tpk1 and Tpk3 play an inhibitory role (Pan and Heitman, 19 MOL. CELL BIOL. 4874-4887 (1999)). Negative regulation of the cAMP-signaling pathway by *S. cerevisiae* occurs when two cAMP phosphodiesterases, Pde1 (low-affinity) and Pde2 (high-affinity), hydrolyze cAMP to AMP and restore PKA to the inactive state (Nikawa et al., 7 MOL. CELL BIOL. 3629-3636 (1987); and Sass et al., 83 PROC. NAT. ACAD. SCI. 9303-9307 (1986)). Pde2 is implicated in filamentous growth in that exogenous cAMP enhances production of pseudohyphae in pde2 mutants (Lorenz and Heitman, supra). Downstream targets of the cAMP/PKA pathway include a transcription factor, Flo8, and a cell wall flocculin, Flo11p, that modulates pseudohyphal differentiation, invasive growth, and cell-cell adhesion of *S. cerevisiae* (Gagiano et al., 31 MOL. MICROBIOL. 103-116 (1999); Guo et al., 97 PROC. NAT. ACAD. SCI. 12158-12163 (2000); and Rupp et al., 18 EMBO J. 1257-1269 (1999)).

Thus, an emerging theme of pathogenesis for plant and animal pathogenic fungi is that modulation of the cAMP dependent signaling pathway is required for morphological transitions to forms expressing virulence attributes necessary for attachment and invasion of host tissues. Induction of virulence gene expression may be accompanied by a morphological transition; however, the morphological form carrying the virulence attributes varies among fungi. In *Magnaporthe grisea*, the CPKA and MAC1 genes, encoding the PKA catalytic subunit and adenylate cyclase respectively, are required for appressorium formation (Choi and Dean, 9 PLANT CELL. 1973-1983 (1997); Mitchell and Dean, 7 PLANT CELL. 1869-1878 (1995)) and subsequent invasion of the hydrophobic surface of the plant. A mutant lacking the MAGB gene encoding the α-subunit of G protein was found to be defective in conidiation and appressorium formation (Liu and Dean, 10 MOL. PLANT MICROBE. INTERACT. 1075-1086 (1997)). In the corn smut fungus, *Ustilago maydis*, null mutants in any component of the cAMP-signaling pathway cause defects in morphological conversions and in pathogenesis (Gold et al., 8 GENES DEV. 2805-2816 (1994); Kruger et al., 13 MOL. PLANT MICROBE. INTERACT. 1034-1040 (2000); and Regenfelder et al., 16 EMBO J. 1934-1942 (1997)). In the case of *Cryptococcus neoformans*, activation of the cAMP dependent signaling pathway by the G protein α-subunit, Gpa1, and the PKA catalytic subunit, Pka1, leads to production of the virulence factors, such as capsule and melanin, on yeasts without changing cell morphology (Alspaugh et al., 11 GENES DEV. 3206-3217 (1997); and D'Souza et al., 21 MOL. CELL BIOL. 3179-3191 (2001)). Whereas genes that serve to activate the cAMP pathway are required for virulence in pathogenic fungi in general, the effects of genes that down-regulate the pathway are poorly understood.

The theme of activation of the cAMP dependent signaling pathway to express virulence attributes necessary for attachment and invasion of host tissue extends to the human fungal pathogen *Candida albicans*. A pulse of cAMP that requires the CAP1 gene (Bahn and Sundstrom, 183 J. BACTERIOL. 3211-3223 (2001)) in response to germ tube inducing conditions leads to production of germ tubes and surface expression of the germ tube specific adhesin, Hwp1, which is required for mucosal and systemic candidiasis (Staab et al., 283 SCIENCE 1535-1538 (1999); Sundstrom et al., 185 J. INFECT. DIS. 521-530 (2002a); and Sundstrom et al., 70 INFECT. IMMUN. 3281-3283 (2002b)). Other studies have found that the CaCDC35 and Tpk1/2 genes, encoding adenylate cyclase and two catalytic subunits of PKA respectively, are required for filamentous growth and virulence of *C. albicans* (Bockmühl et al., 42 MOL. MICROBIOL. 1243-1257 (2001); and Rocha et al., 12 MOL. BIOL. CELL 3631-3643 (2001)). For *C. albicans*, activation of the cAMP-signaling pathway promotes invasiveness and adherence as a consequence of the growth as germ tubes and hyphae.

Although studies of the cap1/cap1 mutant allowed assessment of impaired activation of cAMP signaling (Bahn and Sundstrom, supra), the effects of enhanced or hyperactivation of the cAMP-signaling pathway were not possible. Hypervirulence in the presence of hyperactivation of the cAMP-signaling pathway is found in *C. neoformans* where deletion of PKR1, which encodes the regulatory subunit of PKA, may lead to hypervirulence in animal models due to enhanced capsule production (D'Souza et al., supra). Additionally, detrimental effects of hyperactivation of the cAMP-signaling pathway were found for the plant pathogen, *U. maydis*. Enhanced activation of the cAMP-signaling pathway by constitutive activation of a Gα subunit or by mutation of the UBC1 gene in *U. maydis* led to normal tumor induction, however, fungal proliferation and development were reduced, indicating that detrimental effects may be at play (D'Souza and Heitman, supra; and Kruger et al., supra).

The *C. albicans* PDE1 gene was previously cloned and found to complement heat-shock sensitivity of *S. cerevisiae pde2* mutants, but did not affect morphogenesis (Hoyer et al., 140 MICROBIOLOGY 1533-1542 (1994)). The present invention illustrates that disruption of PDE2 activates the cAMP-signaling pathway by limiting the ability to degrade cAMP in *C. albicans*, whereas overexpression down-regulates the cAMP-signaling pathway in *C. albicans*. The present invention is the first to show that a pde2/pde2 mutant may be hyperactive in forming germ tubes and production of HWP1, which may be accompanied by attenuated virulence. Further, the present invention is the first to describe genetic evidence showing that cAMP promotes true hyphae formation in *C. albicans*. The present invention also describes interference with CAP1 function, which has potential for providing novel strategies for interfering with candidiasis.

By defining the molecular events associated with the cAMP-signalling pathway through the identification of new genes that are associated with the cAMP-signalling pathway, the present invention has strong potential for identifying new and novel ways to interfere with candidiasis. The long-term medical benefits of the present invention may be the development of alternative or adjunctive therapies based on new knowledge about expression of PDE2 and CAP1 genes in *C. albicans*.

Other objects, features and advantages of the present invention will become apparent from the following detailed description. The detailed description and the specific examples, however, indicate only preferred embodiments of the invention. Various changes and modifications within the spirit and scope of the invention will become apparent to those skilled in the art from this detailed description.

SUMMARY OF THE INVENTION

The present invention relates to methods for altering the expression of one or more genes associated with the regulation of the cAMP-PKA signaling pathway in *C. albicans*, resulting in the interference of the virulence properties and disrupting the morphological transitions of *C. albicans*. In particular, virulence properties may include, but are not limited to, adhesive properties, invasive properties (e.g., ability to degrade extracellular matrix proteins and ability to block neutrophil oxygen radical production and degranulation) and proliferative properties. Additionally, the disruption of the morphological transitions comprises the transition from the budding form to the hyphal growth form.

In a further embodiment, the genes associated with the cAMP-PKA pathway comprise the *C. albicans* PDE2 gene and the *C. albicans* homologue of the CAP1 gene. In a yet further embodiment of the present invention, expression of the PDE2 gene may be disrupted by interfering with PDE2 transcription mediated by cis acting sequences. The cis acting sequences of the present invention comprise cis-regulatory elements, such as upstream activating sequences (UAS) and upstream regulatory sequences. In a particular embodiment of the present invention, the cis-regulatory element comprises a cAMP response element (CRE) located in the promoter region of the PDE2 gene. In an alternate embodiment, PDE2 gene expression may be disrupted by interfering with DNA binding proteins (BP) that bind to PDE2 cis-regulatory elements. In particular, the DNA BP comprises the CRE binding protein. Disruption of PDE2 gene expression may lead to enhanced activation of the cAMP-PKA signaling pathway, hyperactive germ tube formation, avirulence, attenuated avirulence, hyperactive production of HWP1, sensitivity to nutrient starvation, defective entry into stationary phase, and/or increased sensitivity to exogenous cAMP in *C. albicans*.

In yet a further embodiment of the present invention, PDE2 gene activity may be enhanced resulting in the overexpression of the PDE2 gene. The activity of the PDE2 gene may be induced by phosphorylation of PKA. Phosphorylation sites on PKA may comprise, but are not limited to, T-26, T-65, S-129, S-209, T-266, S-295, S-436, and S-473. Overexpression of the *C. albicans* PDE2 gene may result in defects in germ tube formation, inhibition of bud-hypha transitions, reduced filamentous growth, and a down-regulation of the cAMP-PKA signaling pathway in *C. albicans*.

Another embodiment of the present invention further comprises a patient infected with *C. albicans*. The patients of the present invention may be immunocompromised and at risk for opportunistic infections. In particular, the patients may be, but are not limited to, an organ transplant recipient, a cancer patient undergoing chemotherapy, a burn patient, an AIDS patient, or a patient with diabetic ketoacidosis.

Another embodiment of the present invention comprises a microarray comprising at least one nucleotide sequence, or fragment thereof, of the PDE2 gene. A further embodiment of the present invention is a method for detecting the expression of a protein capable of regulating the cAMP levels in a microorganism using microarrays and genome-wide expression. In a particular embodiment, the microorganism is bacteria or yeast.

An additional embodiment of the present invention comprises methods for altering the levels of cAMP in *C. albicans* by modifying the expression of the PDE2 gene alone or with the CAP1 gene. Further, the altered levels of cAMP may interfere with the morphogenic transitions of *C. albicans*.

Also, the altered levels of cAMP may interfere with the virulence properties of *C. albicans*. Altered levels of cAMP may comprise either an increase or decrease in intracellular levels of cAMP. In a further embodiment, modifying gene expression may comprise inhibiting or inducing PDE2 gene expression alone or with CAP1 gene expression. One embodiment may comprise inhibiting PDE2 gene expression alone or with CAP1 gene expression. Another embodiment may comprise inhibiting PDE2 gene expression and inducing CAP1 gene expression. A further embodiment may comprise inducing PDE2 gene expression alone or with CAP1 gene expression. Additionally, an embodiment may comprise inducing PDE2 gene expression and inhibiting CAP1 gene expression.

BRIEF DESCRIPTION OF THE DRAWINGS

FIG. 1 is a table of the *Candida albicans* strains used in the present invention.

FIG. 2A is the genetic organization of the CAP1 locus. The CAP1 open reading frame (shaded bar) and PCR products (solid line) (PCR-1.2 and PCR-1.6) are indicated. Each arrowhead indicates primers used for RT-PCR to confirm the disruption of CAP1 (arrow 1: CAP-NRT1, arrow 2: CAP-F1, arrow 3: CAP-R3, arrow 4: CAP-3F1). FIG. 2B depicts a Southern blot analysis of HindIII-digested *C. albicans* genomic DNA probed with PCR-1.2. Lanes 1-6 show parental strain CAI4 (lane 1); CAP1/cap1 strains CAC1 and CAC1-1, Ura$^+$ and Ura$^-$ respectively (lanes 2 and 3); homozygous cap1/cap1 strains CAC1-1A and CAC1-1A1 Ura$^+$ and Ura$^-$ respectively (lanes 4 and 5); and CAP1 complemented strain CACRE1 (lane 6).

FIGS. 3A-3B depict the primary structure alignment of *C. albicans* Cap1 with CAPs of other organisms. Multiple sequence alignments of CAPs from *C. albicans* (CaCAP1; SEQ ID NO:1), *S. cerevisiae* (ScCAP; SEQ ID NO:16), *S. pombe* (SpCAP; SEQ ID NO:17), Mouse (MouseCAP1; SEQ ID NO:18), and Human (HumanCAP1 ; SEQ ID NO:19) were performed with ClustalW (Thompson et al., 22 NUCL. ACIDS RES. 4673-80 (1994)) and illustrated with MACVECTOR® 6.5.3 (Oxford Molecular Company). Solid lines indicate residues for the conserved RLE/RLE motif (Hazen et al., 24 INFECT. IMMUN. 661-6 (1979); Hood et al., 28 CLIN. INFECT. DIS. 587-96 (1999); Huang et al., 30 SCAND. J. INFECT. DIS. 137-42 (1998); Kawamukai et al., supra; Kawarabayashi et al., 28 GYNECOL. OBSTET. INVEST. 132-7 (1989); Kimura and Pearsall, 21 INFECT. IMMUN. 64-8 (1978); Kohler and Fink, 93 PROC. NATL. ACAD. SCI. USA 13223-8 (1996); Kurtz et al., 6 MOL. CELL. BIOL. 142-9 (1986); Kyte and Doolittle, 157 J. MOL. BIOL. 105-32 (1982); Lebrerer et al., 7 CURR. BIOL. 539-46 (1997)), the polyproline region (289-297) and two consensus SH3-binding motifs (358-361 and 364-367) *C. albicans*.

FIGS. 4A-4B depict Northern blot and RT-PCR analysis of cap1/cap1 mutants. CAP1 mRNA is absent in the cap1/cap1 strain and present at equivalent low levels in other strains during yeast growth (FIG. 4A) or germ tube induction (FIG. 4B). Total RNA (7 μg/lane) isolated was separated in a formaldehyde agarose gel transferred to a nitrocellulose membrane, and probed with radiolabeled PCR-1.2 to detect CAP1 mRNA and 18S rRNA as a control. The membrane was exposed to X-ray film for seven days for detection of CAP1 mRNA and for four hours for detection of 18S rRNA. FIG. 4C depicts amplification of 5'-(605 bp, 1 to 605) and 3'-portions (713 bp, 922 to 1634) of CAP1 mRNA using RT-PCR and Southern blot using radiolabeled PCR-1.6 as probe. ACT1 mRNA (304 bp) was amplified as a positive control. Lanes 1-4 show strains UnoPP-1, CAC1, CAC1-1A, and CACRE1, respectively.

FIG. 5 shows a table of the time required for *C. albicans* strains to double in numbers.

FIGS. 7A-7B depict the phenotypic analyses of cap1/cap1 mutants in agar media. cap1/cap1 strains were defective in filamentous growth. Colonial appearances (FIG. 7A) and cellular morphologies at colony rims (FIG. 7B), respectively, in each agar media condition are shown. FIG. 7A depicts colonies of the cap1/cap1 mutant. The colonies consisted of budding yeasts (third columns in FIGS. 7A and 7B), whereas strains with CAP1 (UnoPP-1, CAC1, and CACRE1) produced filamentous growths of differing characteristics depending on the media. The asymmetric colonies formed by strains with CAP1 in serum contained infrequent thick plumes composed of filaments covered with buds radiating from the colony center (arrow). FIG. 7B depicts strains with CAP1. These strains produced uniform hyphae with short branches in M199 and Spider plates (arrows "1") or hyphae with thick-walled terminal buds in SLAD media (arrows "2"). In media with serum, colonies of strains with CAP1 were composed primarily of hyphae bereft of buds (arrows "3"). M199 plates were incubated first at 30° C. for 48 h and transferred to 37° C. for another 48 h, whereas the other plates were incubated for 6 days at 37° C. Black and white bars indicate lengths of 1 mm and 50 μm, respectively.

FIG. 8A displays germ tube inducing conditions (M199 at 37° C.). cAMP levels (pmol per mg protein) at time zero for UnoPP-1, CAC1, CAC1-1A, and CACRE were 45.3±4.6, 55.1±6.9, 61.8±6.5, and 51.4±6.7 (mean value±standard deviation), respectively. The decreased cAMP level in the cap1/cap1 mutant compared to strains with CAP1 at 1 h was statistically significant (*, $p<0.01$ (UnoPP-1 or CAC1 vs. CAC1-1A) and $p<0.05$ (CACRE1 vs. CAC1-1A) using Bonferroni's multiple comparison test performed with Prism 2.0b (GraphPad Software)). FIG. 8B shows budding growth in M199 at 27° C. cAMP levels (pmol per mg protein) at time zero for UnoPP-1, CAC1, CAC1-1A, and CACRE were 50.9±22.4, 58.1±8.4, 37.4±2.9, and 52.6±6.6, respectively. FIG. 8C depicts the morphological changes of UnoPP-1 (CAP1/CAP1), CAP1/cap1 strain (CAC1 and CACRE1) and cap1/cap1 strain (CAC1-1A) were monitored during germ tube induction. Bars indicate a length of 5 µm.

FIGS. 9A-9B depict the suppression of defective bud-hypha transitions and filamentous growth in the cap1/cap1 mutant by exogenous cAMP or its derivative, dbcAMP. The wild type CAP1/CAP1 strain, UnoPP-1, and the cap1/cap1 mutant strain, CAC1-1A, were grown in (FIG. 9A) SLAD media with or without 10 mM cAMP or dbcAMP for 5 days at 37° C. Bars indicate a length of 1 mm. FIG. 9B depicts bud-hypha transitions induced at cell concentrations of $1\times10^6$ cells/ml in pre-warmed M199+serum with or without 10 mM dbcAMP for 13 hours (first (UnoPP-1) and second (CAC1-1A) columns, 20× objective; third (CAC1-1A) column, 40× objective). Bars indicate a length of 30 µm.

FIG. 12 provides a listing of the C. albicans strains used in Example 9.

FIG. 13 depicts the highly conserved phosphodiesterase signature sequence of Pde2 of C. albicans, S. cerevisiae and humans (CaPDE2 (SEQ ID NO:3), ScPDE2 (SEQ ID NO:4) and HuPDE2A3 (SEQ ID NO:5), respectively). The alignment was created with ClustalW (Thompson et al., 22 NUCL. ACIDS RES. 4673-4680 (1994)) and illustrated with MACVECTOR® 6.5.3 (Oxford Molecular Company, Burlington, Mass.). Conserved phosphodiesterase signature motif was found using the ProDom database.

FIGS. 14A-14C depict disruption of the PDE2 gene in the wild type and cap1/cap1 backgrounds. FIG. 14A illustrates a strategy for disruption of PDE2. The horizontal arrow indicates the complete 1713-bp coding region of PDE2. The numbers 1 and 2 represent primers, PDE2W-R1 and PDE2W-F1 that were used to amplify the PDE2 open reading frame. This fragment was used as a probe for Southern and Northern blot analyses and also for constructing the PDE2 overexpression strains. The insertion site of the hisG-URA3-hisG cassette is indicated. The 3-kbp revertant rescue fragment was used for constructing the PDE2 revertant strain. FIG. 14B depicts a Southern blot analysis of HindIII-digested genomic DNA of pde2/pde2 mutants probed with PDE2. Lanes: 1, parental strain CAI4; 2 and 3, BPS1 (Ura+) and BPS2 (Ura−); 4 and 5, BPS4 (Ura+) and BPS7 (Ura−); 6, the PDE2 revertant strain BPS9; 7, CAC1-1A1 (Ura−); 8 and 9, BPS 16 (Ura+) and BPS17 (Ura−); 10 and 11, BPS18 (Ura+) and BPS20 (Ura−); 12, the PDE2 revertant strain BPS22. The wild type, heterozygous PDE2/pde2, and PDE2 revertant strains exhibited 3.0/5.8-kb hybridization bands for the wild type PDE2 allele. Site-specific disruption of PDE2 genes with hisG-URA3-hisG or hisG generated 11.4-kb and 8.5-kb bands, respectively. FIG. 14C depicts the RT-PCR analysis of pde2/pde2 or cap1/cap1 pde2/pde2 mutants. Lanes: 1, UnoPP-1; 2, BPS1; 3, BPS4; 4, BPS9; 5, CAC1-1A; 6, BPS16; 7, BPS18; 8, BPS22. ACT1 mRNA (304-bp) served as a loading control. Note the absence of PDE2 cDNA (1713-bp) in pde2/pde2 and cap1/cap1 pde2/pde2 mutants (lane 3 and 7, respectively) and recovery of PDE2 expression in revertant strains (lane 4 and 8).

FIG. 15A illustrates colonial and cellular morphologies of the control and mutant strains (UnoPP-1 (WT), BPS1 (PDE2/pde2), BPS4 (pde2/pde2), BPS 15 (pde2/pde2 eno1::URA3), and BPS9 (revertant)) grown at 30° C. for 48 hours on YPD (a1-5 and b1-5) and YNB (c1-5 and d1-5) plates, or in liquid YPD and YNB media (e1-5 and f1-5, respectively). Note the wrinkled colonial morphologies of pde2/pde2 mutants on YPD plates exhibiting mixture of elongated yeasts and filamentous forms (inserted images and black arrows, respectively, in b3 and b4). Note the massive aggregates mainly composed of hyphae in pde2/pde2 mutants (circles in b3 and b4) and lesser aggregates of yeast and short filamentous forms in PDE2/pde2 mutants (squares in b2 and b5) grown on YPD. Note the absence of wrinkled appearance in pde2/pde2 mutant colonies on YNB plates (c3 and c4). The cells appear pseudohyphal and aggregated (white arrow and circles, respectively, in d3 and d4). White and black bars, 1 mm and 15 µm, respectively. FIG. 15B illustrates the immunofluorescence assay (IFA) that was performed using anti-Hwp1 antibodies as primary antibodies as previously described (Staab et al., 271 J. BIOL. CHEM. 6298-6305 (1996)). The pde2/pde2 mutant (BPS4) was grown at 30° C. for 48 hours in either YPD or YNB media, washed and fixed in PBS containing 0.5% formaldehyde. Note the Hwp1-positive true hyphae in YPD media (white arrows) and the Hwp1-negative pseudohyphae in YNB media (yellow arrows). True hyphal forms were more frequently observed on solid YPD than in liquid YPD.

FIGS. 16A-16B illustrate the rapid induction of bud-hypha transitions and hyperfilamentous growth of C. albicans pde2/pde2 mutants compared to the wild type strain. FIG. 16A shows yeast cells of UnoPP-1 (WT) and BPS 15 (pde2/pde2) strains that were cultured to middle logarithmic phase at YNB at 25° C., briefly sonicated to disperse the cells for counting, washed with 1×PBS, inoculated into M199 prewarmed at 37° C. at a concentration of $5\times10^6$ cells/ml, and incubated for 5 hours. Cellular morphology was observed at each time point (0, 0.5, 1, 1.5, 3, and 5 hours). Germ tube formation was more rapid in pde2/pde2 cells. For example, upon 1 hour incubation, most pde2/pde2 cells (>90%) had short germ tubes whereas wild type cells did not. Bar, 15 µm. FIG. 16B depicts colonial (first and third rows) and colonial rim (second and fourth rows) appearances of the strains described in FIG. 15A in solid Spider media (first and second rows) and 4% serum media (third and fourth rows). Note the absence of buds on filaments of the pde2/pde2 mutant (squares in the second row) as compared to the other strains (circles in the second row) in Spider media. The effect was more pronounced in serum media in that filaments of the PDE2/pde2 heterozygote also appeared to lack buds (squares in the fourth row), whereas buds were evident on filaments of the wild type strain (circle in the fourth row). Each plate was incubated at 30° C. for 3 and 4 days, respectively. White and black bars, 0.5 mm and 150 µm, respectively.

FIG. 17A shows the Southern blot analysis of BglII-digested genomic DNA of the parental strain CAI4 and Ura+ PDE2 overexpressing strains (EPDE2-3, FIG. 12) probed with the 1.4-kb XbaI-XhoI fragment of p24eno (cENO)(Postlethwait and Sundstrom, 177 J. BACTERIOL. 1772-1779 (1995)). Predicted hybridization bands of 2.6/5.0 kb for a disrupted ENO1 allele with pENO1PDE2-3 (eno1::ENO1p-PDE2-URA3), and 1.3/3.4 kb bands for the wild type ENO1 allele were found in EPDE2-3. FIG. 17B depicts a Northern blot showing increased levels of PDE2 mRNA in EPDE2-3 as compared to control (EGFP3, FIG. 12) in both budding and hyphal growth (Lee's at pH 4.5 and pH 6.8 respectively). The expected cellular and colonial morphologies were verified by microscopic observation. FIG. 17C illustrates the bud-hypha transitions that were induced in M199 with or without 5% serum, and Lee's media (pH6.8), all at 37° C. Cellular morphologies were observed after 3 or 20 hours of incubation. Note that the strains overexpressing PDE2 grew predominantly as yeasts (white arrows) whereas the control strain was filamentous (black arrows). Bar, 20 µm. FIG. 17D shows that the conditions for filamentous growth were Spider, 4% serum, and SLAD media at 37° C. for 5 to 7 days as described in FIG. 16. PDE2 overexpressing strains showed reduced filamentous growth in the three media. Black and white bars, 0.5 mm and 150 µm, respectively.

FIG. 18A illustrates that the germ tubes of each strain (UnoPP-1 (WT), CAC1-1A (cap1/cap1 PDE2/PDE2), BPS 16 (cap1/cap1 PDE2/pde2), BPS 18 (cap1/cap1 pde2/pde2), and BPS22 (cap1/cap1 PDE2 revertant)) were induced at a cell concentration of $5 \times 10^6$ cells/ml in prewarmed (37° C.) M199 media for 6 hours (a1-5) and 20 hours (a6-10). Identical results were found in Lee's media (pH6.8, 37° C.)(data not shown). Germ tubes of cap1/cap1 pde2/pde2 double mutant (black arrows in a4 and a9) were equivalent to those of the wild type strain (black arrows in a1 and a6). Reintroduction of PDE2 gene restored the defective germ tube formation phenotype to the cap1/cap1 mutant (white arrow in a5). Filamentous growth of each strain was induced at 37° C. for 6 days in solid Spider media (a11-15) and 2% agar media containing 4% bovine calf serum (a16-20). Note that the cap1/cap1 pde2/pde2 mutants appeared hyperfilamentous (a14 and a19) as compared to the wild type strain (a11 and a16). The PDE2 revertant strain (a15, a20, a24, and a28) was similar to the cap1/cap1 mutant (a12, a17, a22, and a26) in the presence of budding colonies with irregular edges (a20 and a28) in serum media. Black bars, 15 µm (a1 to a10) and 150 µm (a21 to a28). White bars, 0.5 mm (a11 to a20). FIG. 18B shows SLAD agar media with or without 10 mM of the membrane permeable cAMP derivative, dibutyryl cAMP (dbcAMP) (200 cells/plate). Note that filamentation of the cap1/cap1 pde2/pde2 mutant (b4 and b9) is only slightly increased relative to the cap1/cap1 mutant (b2 and b7) and is not as extensive as in the wild type strain (b1 and b6). Filamentation is greatly enhanced by the addition of exogenous dbcAMP (b5 and b10); however, more buds are present on the filaments of these colonies (b10) than on filaments of the wild type colonies (b6). Black and white arrows indicate hyphae with or without buds, respectively. White and black bars, 0.5 mm and 150 µm, respectively.

FIG. 19A shows the susceptibility of C. albicans strains (UnoPP-1 (WT, ■), CAC1-1A (cap1/cap1, ), BPS4 (pde2/pde2, □), and BPS18 (cap1/cap1 pde2/pde2, ○)) to nutrient deprivation, as assessed by the ability to survive incubation in PBS as described in the experimental procedures, infra. Error bars indicate the standard deviation of each value from two independent experiments. For statistical analysis, Bonferroni's multiple comparison test was performed with Prism 2.0b (GraphPad Software). The difference in survival between the pde2/pde2 mutant and the other strains at 30° C. was significant at 16 and 24 hours, P<0.05 and P<0.01 respectively, and at 37° C., after 4 hours to 24 hours (P<0.01). "*" denotes time points where differences between the pde2/pde2 mutant and the other strains are significant. FIG. 19B shows that the indicated C. albicans strains (UnoPP-1 (WT), BPS1 (PDE2/pde2), BPS4 (pde2/pde2), BPS9 (PDE2 revertant), BPS 18 (cap1/cap1 pde2/pde2), and CAC1-1A (cap1/cap1) were streaked on YPD plates and incubated at 30° C. for 48 hours prior to treatment with an iodine/iodide solution as described in experimental procedures, infra. Note that the glycogen staining indicated by a brown color is most and least intense in the cap1/cap1 and pde2/pde2 mutants, respectively.

FIG. 20A shows the cell morphology after 6 hours in the presence of cAMP. Note the swollen appearance of pde2/pde2 cells grown in the presence of cAMP (arrows). Bar, 15 µm. FIG. 20B shows the effect of cAMP on growth. The relative growth rate of the pde2/pde2 mutant (BPS4) in the presence compared to the absence of cAMP was reduced whereas strains with a wild type PDE2 gene (UnoPP-1, BPS1, and BPS9) were not affected by exogenous cAMP. The results were statistically significant for both 4 mM (p<0.05) and 40 mM (p<0.001). Error bars indicate the standard deviation of each value from two independent experiments. For statistical analysis, Bonferroni's multiple comparison test was performed with Prism 2.0b (GraphPad Software).

FIGS. 21A-B depict the northern blot analysis used to assess expression of PDE2 during budding growth and germ tube induction. FIG. 21A shows that the total RNA (7.5 µg/lane) isolated from the wild type strain (SC5314) and the cap1/cap1 mutant (CAC1-1A), was separated in a formaldehyde agarose gel, transferred to a nitrocellulose membrane, and probed for PDE2, HWP1, and 18S rRNA as a loading control as described in experimental procedures, infra. The membrane was exposed to X-ray film for 2 days for detection of PDE2 mRNA, overnight for detection of HWP1 mRNA, and for 4 h for detection of 18S rRNA. FIG. 20B shows the phosphorimaging analysis of PDE2 expression in the wild type and cap1/cap1 strains. Fold induction was calculated as described in experimental procedures. Note the appearance of PDE2 message within 10 minutes of placing wild type cells in germ tube induction conditions (arrow). Induction of PDE2 mRNA is greatly reduced in the cap1/cap1 mutant.

DETAILED DESCRIPTION OF THE INVENTION

Figure 2:
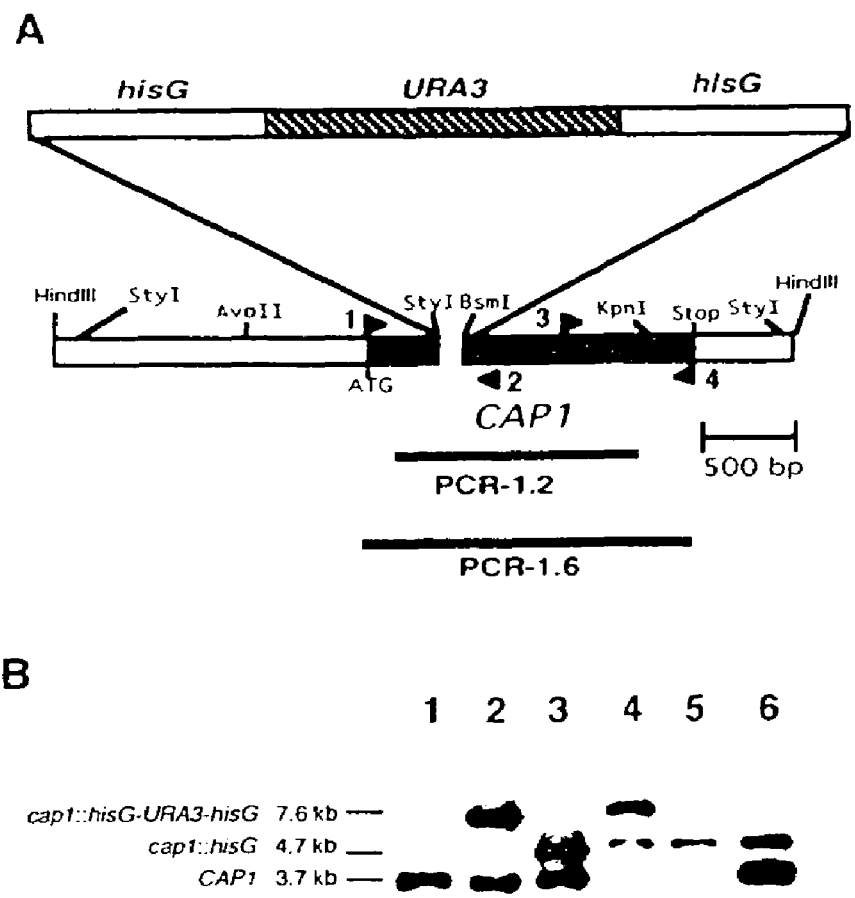
FIGS. 2A-2B represent the disruption of *C. albicans* CAP1.

It is understood that the present invention is not limited to the particular methodology, protocols, cell lines, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a Pde2" is a reference to one or more Pde2's and equivalents thereof known to those skilled in the art and so forth.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Definitions

Homologue: refers to chromosomes carrying the same genetic loci. Thus, a diploid cell has two copies of each homologue, one derived from each parent.

Virulent phage mutant: a mutant that is unable to survive in bacterium as a stable prophage component of the bacterial genome.

Morphogenic: as used herein refers to a factor that induces development of particular cell types in a manner that depends on its concentration.

Open reading frame: as defined herein, includes a sequence of nucleotides that contains a series of triplets coding for amino acids without any termination codons. Such a sequence is potentially translatable to protein.

Promoter: a recognition site on a DNA sequence or group of DNA sequences that provides an expression control element for a gene and to which RNA polymerase specifically binds and initiates RNA synthesis (transcription) of that gene.

Inducible promoter: a promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

Viral promoter: a promoter with a DNA sequence substantially similar to the promoter found at the 5' end of a viral gene. A typical viral promoter is found at the 5' end of the gene coding for the p2I protein of MMTV described by Huang et al., 27(2 Pt. 1) CELL 245-55 (1981).

Synthetic promoter: a promoter that was chemically synthesized rather than biologically derived. Usually synthetic promoters incorporate sequence changes that optimize the efficiency of RNA polymerase initiation.

Constitutive promoter: a promoter where the rate of RNA polymerase binding and initiation is approximately constant and relatively independent of external stimuli.

Heterologous Polypeptide: a linear series of amino acid residues connected one to the other by peptide bonds between the alpha-amino and carboxy groups of adjacent residues originating from a species other than the plant host system within which said linear series is produced. "Polypeptide" also encompasses a sequence of amino acids, peptides, fragments of polypeptides, proteins, globular proteins, glycoproteins, and fragments of these.

Multimeric protein: a protein containing more than one separate polypeptide or protein chain, each associated with the other to form a single protein. Both heterodimeric and homodimeric proteins are multimeric proteins.

Immunoglobulin: a polypeptide, protein or multimeric protein containing at least the immunologically active portion of an immunoglobulin heavy chain and is thus capable of specifically combining with an antigen. Exemplary immunoglobulins are immunoglobulin heavy chains, immunoglobulin molecules, substantially intact immunoglobulin molecules, any portion of an immunoglobulin that contains the paratope, including those portions known in the art as Fab fragments, Fab' fragments, $F(ab')_2$ fragments and Fv fragments.

Recombinant: as used herein, broadly describes various technologies whereby genes can be cloned, DNA can be sequenced, and protein products can be produced. As used herein, the term also describes proteins that have been produced following the transfer of genes into the cells of host systems.

Fusion protein: a protein in which peptide sequences from different proteins are covalently linked together.

Hybridization: broadly defined, any process by which a nucleic acid sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency. In particular, stringency can be increased by reducing the concentration of salt, increasing the concentration of formamide, or raising the hybridization temperature. For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. To remove nonspecific signals, blots can be sequentially washed, for example, at room temperature under increasingly stringent conditions of up to 0.1× saline sodium citrate and 0.5% sodium dodecyl sulfate. Variations on the above ranges and conditions are well known in the art.

Isolated: as used herein, refers to any element or compound separated not only from other elements or compounds that are present in the natural source of the element or compound, but also from other elements or compounds and, as used herein, preferably refers to an element or compound found in the presence of (if anything) only a solvent, buffer, ion, or other component normally present in a solution of the same.

Nucleic acid sequences: as the term is used herein, nucleic acid sequences encoding a a PDE2 and/or CAP1 gene or functional equivalents thereof including those with deletions, insertions, or substitutions of different nucleotides resulting in a polynucleotide that encodes a Pde2 and/or Cap1 or a functionally equivalent of Pde2 and/or Cap1. Included within this definition are polymorphisms which may or may not be readily detectable using a particular oligonucleotide probe of the polynucleotide encoding a protein and improper or unexpected hybridization to alleles, with a locus other than the normal chromosomal locus for the polynucleotide sequence encoding a heterologous polypeptide. The encoded protein may also be "altered" and contain deletions, insertions, or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the biological or immunological activity of a protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

The term "nucleic acid sequence," includes an oligonucleotide, nucleotide, or polynucleotide, and fragments thereof, and to DNA or RNA of genomic or synthetic origin, which may be single- or double-stranded, and represent the sense or antisense strand, to peptide nucleic acid (PNA), or to any DNA-like or RNA-like material, natural or synthetic in origin.

Antisense gene: an antisense gene is constructed by reversing the orientation of the gene with respect to its promoter so that the antisense strand is transcribed.

Antisense RNA: an RNA molecule complementary to a particular RNA transcript that can hybridize to the transcript and block its function.

Amino acid sequences: as used herein, this term includes an oligopeptide, peptide, polypeptide, or protein sequence, and fragment thereof, and to naturally occurring or synthetic molecules.

Fragments: include any portion of a heterologous peptide or nucleic acid sequence. Heterologous peptide fragments retain at least one structural or functional characteristic of the subject heterologous polypeptides. Nucleic acid sequence fragments may specifically be greater than about 60 nucleotides in length, and most specifically include fragments that are at least about 100 nucleotides, at least about 1000 nucleotides, and at least about 10,000 nucleotides in length.

Chemical derivative: as used herein, a molecule is said to be a "chemical derivative" of another molecule when it contains additional chemical moieties not normally a part of the molecule. Such moieties can improve the molecule's solubility, absorption, biological half-life, and the like. The moieties can alternatively decrease the toxicity of the molecule, eliminate or attenuate any undesirable side effect of the molecule, and the like.

Complementary or complementarity: as used herein, include the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of molecules.

Deletion: as used herein, refers to a change in the amino acid or nucleotide sequence and results in the absence of one or more amino acid residues or nucleotides.

Insertion or addition: as used herein, includes a change in an amino acid or nucleotide sequence resulting in the addition of one or more amino acid residues or nucleotides, respectively, as compared to the naturally occurring molecule.

Introduction: insertion of a nucleic acid sequence into a cell, by methods including infection, transfection, transformation or transduction.

Transfection: as used herein includes the process of introducing a DNA expression vector into a cell. Various methods of transfection are possible including microinjection or lipofection.

Transformation: a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, and lipofection.

Functional equivalent: a protein or nucleic acid molecule that possesses functional or structural characteristics that is substantially similar to a heterologous protein, polypeptide, enzyme, or nucleic acid. A functional equivalent of a protein may contain modifications depending on the necessity of such modifications for the performance of a specific function. The term "functional equivalent" is intended to include the "fragments," "mutants," "hybrids," "variants," "analogs," or "chemical derivatives" of a molecule.

Variant: an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art, for example, DNASTAR® software.

% similarity or % identity: refer to the percentage of sequence similarity or identity found in a comparison of two or more amino acid or nucleic acid sequences. Percent similarity can be determined by methods well-known in the art. For example, percent similarity between amino acid sequences can be calculated using the clustal method. See, e.g., Higgins & Sharp, 73 GENE 237-44 (1988). The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent similarity can be calculated by other methods known in the art, for example, by varying hybridization conditions, and can be calculated electronically using programs such as the MEGALIGN™ program (DNASTAR Inc., Madison, Wis.).

Operably linked: as used herein, refers to the state of any compound, including but not limited to deoxyribonucleic acid, when such compound is functionally linked to any promoter. In the context of the present invention, the nucleic acid sequence is one that encodes for Pde2 and/or Cap1. The promoter sequence initiates and mediates transcription of the nucleic acid sequence.

Vector: a cloning vector that is designed so that a coding nucleic acid sequence inserted at a particular site will be transcribed and translated. A typical expression vector may contain a promoter, selection marker, nucleic acids encoding signal sequences, and regulatory sequences, e.g., polyadenylation sites, 5'-untranslated regions, and 3'-untranslated regions, termination sites, and enhancers. "Vectors" include viral derived vectors, bacterial derived vectors, plant derived vectors and insect derived vectors.

Liposome: a "liposome" is a small vesicle composed of various types of lipids, phospholipids and/or surfactant, which is useful for delivery of a drug to a mammal. The binding partners of the present invention may be delivered by a liposome. The components of the liposome are commonly arranged in a bilayer formation, similar to the lipid arrangement of biological membranes.

Protein purification: broadly defined, any process by which proteins may be separated from other elements or compounds on the basis of charge, molecular size, or binding affinity.

Substantially purified: as used herein, includes nucleic or amino acid sequences that are removed from their natural environment, isolated or separated, and may be at least 60% free, specifically at least 75% free, and most specifically at least 90% free from other components with which they are naturally associated.

Expression cassette: is conventional and refers to a combination of regulatory elements that are required by the host for the correct transcription and translation (expression) of the genetic information contained in the expression cassette. These regulatory elements comprise a suitable (i.e., functional in the selected host) transcription promoter and a suitable transcription termination sequence.

Promoter: generally includes a regulatory region of DNA capable of initiating, directing and mediating the transcription of a nucleic acid sequence. Promoters may additionally comprise recognition sequences, such as upstream or downstream promoter elements, which may influence the transcription rate. Specifically, in the context of the present invention, the promoters may be the PDE2 or CAP1 gene promoters.

Inhibition: as used herein, refers to a reduction in the parameter being measured, whether it be *C. albicans* growth or viability. The amount of such reduction is measured relative to a standard (control). "Reduction" is defined herein as a decrease of at least around 25% relative to control, preferably at least around 50%, and most preferably of at least around 75%.

DNA template: refers to double-stranded DNA and where indicated by the particular binding assay to single-stranded DNA that may be negatively supercoiled, possesses a promoter region.

Cis-acting element: refers to a variety of modular elements or target sequences. These elements may be targets for tissue-specific or temporal regulation. Generally, these elements only affect the activity of DNA sequences of its own DNA molecule. These elements may be found within enhancers, promoters, or other regulatory elements of a particular gene.

DNA binding protein: refers to transcription factors and other regulatory proteins that recognize specific target sequences located in enhancers, promoters, or other regulatory elements that affect a particular target gene. For a repressor protein, binding to DNA may itself be sufficient to excersise its function, e.g., inhibit transcription. Alternatively, to be a positive regulatory protein, the DNABP may excersise its function by binding to regulatory proteins or other transcription factors.

Binding Partner: as used herein, the term "binding partner" refers to a molecule that may bind to Pde2 and/or Cap1 polypeptides and inhibit bud-hypha morphogenic transitions of *C. albicans* associated with expression of PDE2 and/or CAP1. Thus, in this regard, a binding partners may be considered to a be a therapeutic agent. In a specific embodiment of the present invention, a binding partner is a polypeptide, i.e., a polypeptide Pde2 and/or Cap1 binding partner. Examples of polypeptide Pde2 and/or Cap1 binding partners include, but are not limited to, immunoglobulins and functional equivalents thereof, peptides generated by rational design, etc. In another embodiment, a Pde2 and/or Cap1 binding partner may comprise a polynucleotide, i.e., a polynucleotide Pde2 and/or Cap1 binding partner. A polynucleotide Pde2 and/or Cap1 binding partner may include, but is not limited to, an antisense oligonucleotide, a ribozyme, or a peptide nucleic acid. In yet another embodiment, a Pde2 and/or Cap1 binding partner may comprise a small molecule, i.e., a small molecule Pde2 and/or Cap1 binding partner. In the context of Pde2 and/or Cap1, the term "functional equivalent" refers to a protein or polynucleotide molecule that possesses functional or structural characteristics that are substantially similar to all or part of the native Pde2 and/or Cap1 protein or native Cap 1- and/or Pde2-encoding polynucleotides. A functional equivalent of a native Pde2 and/or Cap1 protein may contain modifications depending on the necessity of such modifications for a specific structure or the performance of a specific function. The term "functional equivalent" is intended to include the "fragments," "mutants," "derivatives," "alleles," "hybrids," "variants," "analogs," or "chemical derivatives" of native Pde2 and/or Cap1.

Immunoglobulin and functional equivalent: In the context of immunoglobulins, the term "functional equivalent" refers to immunoglobulin molecules that exhibit immunological binding properties that are substantially similar to the parent immunoglobulin. As used herein, the term "immunological binding properties" refers to non-covalent interactions of the type, which occur between an immunoglobulin molecule and an antigen for which the immunoglobulin is specific. Indeed, a functional equivalent of a monoclonal antibody immunoglobulin, for example, may inhibit the binding of the parent monoclonal antibody to its antigen. A functional equivalent may comprise F(ab')$_2$ fragments, F(ab) molecules, Fv fragments, single chain fragment variable displayed on phage (scFv), single domain antibodies, chimeric antibodies, or the like so long as the immunoglobulin exhibits the characteristics of the parent immunoglobulin.

Microarray: refers to a plurality of polymeric molecules spatially distributed over, and stably associated with, the surface of a substantially planar substrate. The microarray of the present invention refers to a microfabricated array of large numbers of different oligonucleotide probes that can effectively be used to not only detect the presence or absence of target nucleic acid sequences, but to quantify the relative abundance of the target sequences in a complex nucleic acid pool. The oligonucleotide probes are complementary to the RNA transcripts or nucleic acids derived from the RNA transcripts and can quantify the hybridized nucleic acids in the array.

In accordance with the present invention, a patient may include immunocompromised or immunosuppressed humans, for example, those having AIDS or undergoing transplantation or anti-cancer therapy. The invention also preferably relates to humans with primary or secondary immunodeficiencies (see, MERCK MANUAL 16th ed., Chapter 19 (1992), herein incorporated by reference). In addition to mammalian hosts in which the normal immune response has been compromised or suppressed, the invention relates to mammalian hosts in which the normal microbial flora has been disrupted, for example, because of disease (e.g., hereditary, metabolic, infiltrative, or hematologic), trauma (e.g., burn, splenectomy, anesthesia), surgical or clinical procedure (e.g., catheterization or introduction of artificial implants such as dentures), or chemical, radiation, or other immunosuppressive prophylaxis or treatment. Accordingly, microbial infections include infections related to opportunistic as well as pathogenic microorganisms.

The present invention shows that hyperactivation of the cAMP dependent signaling pathway leads to detrimental effects such as sensitivity to nutrient starvation, defective entry into stationary phase and avirulence in C. albicans. Indeed, control of cAMP levels may be required to optimize the extent of hyphal versus budding growth and to express virulence attributes with attendant disadvantageous effects. Furthermore, the present invention relates to an important role for CAP1 and cAMP-mediated activation of PDE2 gene expression for maintaining tight control of cAMP levels in fungi. Given the frequent associations of morphological conversions with virulence attributes, strategies to interfere with modulation of cAMP levels may have wideranging applications in interfering with interactions between a variety of fungal pathogens with their corresponding plant and animal hosts.

The present invention illustrates that C. albicans PDE2 encodes a high-affinity phosphodiesterase that may serve to degrade cAMP, thereby opposing the effects of the adenylate cyclase associated protein, Cap1, which activates the pathway by increasing the levels of cAMP. A highly conserved phosphodiesterase signature sequence is present in C. albicans Pde2 and C. albicans pde2/pde2 mutants have similar phenotypes as the pde2/pde2 mutants of S. cerevisiae (Harashima et al., 10 MOL. CELL 163-173 (2002); Toda et al., 40 CELL 27-36 (1985); Wilson et al., 325 FEBS 191-195 (1993)). Generally, the pde2/pde2 phenotypes exhibit a slow rate of division and a larger cell size in the presence of exogenous cAMP, rapid loss of viability following nutrient deprivation, and failure to enter into stationary phase upon nutrient exhaustion.

The present invention also describes the sensitivity of pde2/pde2 mutants to the toxic effects of external cAMP, and the presence of normal germ tube formation in cap1/cap1 pde2/pde2 double mutants as compared to the cAMP-deficient, germ tube-defective cap1/cap1 mutants. Further, the present invention illustrates that the cAMP-signaling pathway may play a major role in morphological transitions in C. albicans with higher cAMP levels favoring filamentous growth. Suppressing the ability to degrade cAMP by disrupting the PDE2 gene may lead to enhanced filamentous growth whereas overexpression may lead to diminished filamentous growth. cAMP levels may also vary at the individual cell level as suggested by the presence of mixed morphologies in cultures of a single strain in PDE2/pde2 orpde2/pde2 mutants growing on YPD. Reasons for the presence of multiple morphologies in a single culture may be related to the cell cycle. In S. cerevisiae, the transcription of cyclins depends on cAMP (Aldea et al., 10 MICROBIOLOGIA 27-36 (1994); and Thevelein, 62 ANTONIE VAN LEEUWENHOEK 109-130 (1992)). The intracellular cAMP level in pde2/pde2 mutant cells may increase over the threshold level of cAMP required for bud-hypha transitions depending on the stage of the cell cycle, resulting in hypha production or cell elongation.

Additionally, the present invention illustrates that pde2/pde2 mutants are avirulent. The avirulent phenotype of pde2/pde2 mutants may be correlated with the detrimental effects of hyperactivation of cAMP signaling including defective entry into stationary phase, increased sensitivity to nutrient starvation and toxicity to exogenous cAMP. The impaired ability of pde2/pde2 mutants to accumulate glycogen and enter into stationary phase and the more rapid loss of viability at 37° C. than at 30° C. shows that sensitivity to nutrient starvation and entry into stationary phase may be relevant to growth in animal hosts. Premature entry into stationary phase may also be detrimental to growth in the host as shown by the enhanced glycogen accumulation in avirulent cap1/cap1 mutants. Other manifestations of hyperactivation of cAMP signaling, however, may also be involved. cAMP levels can be controlled to optimize the levels of filamentation, adherence and invasion necessary for invasion and growth in host tissue while minimizing detrimental effects on cell growth.

Figure 23:
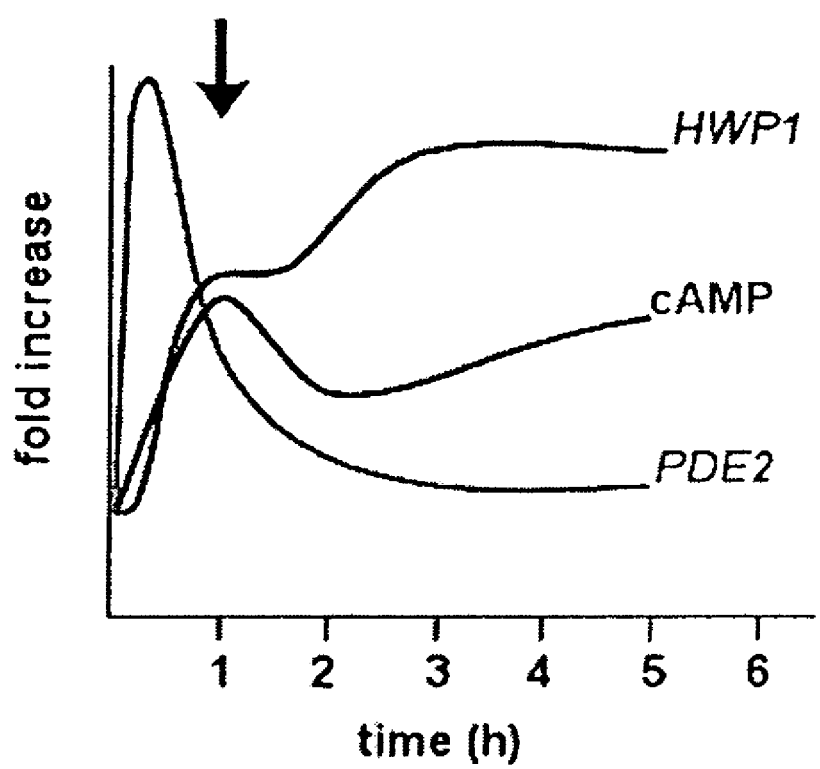
FIG. 23 shows the inferred temporal pattern of levels of cAMP, PDE2 and HWP1 mRNA, respectively, after placing yeasts in conditions inducing germ tubes (M199 at 37° C.) in wild type strains of C. albicans. Approximately 20% of cells have short germ tubes at 1 hour (black arrow). Rising cAMP causes activation of PDE2 gene expression that peaks within 20 minutes whereas HWP1 mRNA peaks at 3 hours.

The present invention further demonstrates that a requirement for regulation of cAMP levels may be imposed to accommodate the major impact of cAMP signaling on both positive and negative virulence attributes. The more rapid elongation of germ tubes in the pde2/pde2 mutant as compared to wild type cells may suggest that an increase in Pde2 activity may be tightly coupled to germ tube induction in wild type cells. PDE2 mRNA levels during germ tube induction are 5 to 10 fold higher than in yeast growth indicating a morphology-specific upregulation that preceded the peak of cAMP measured before germ tube emergence. The temporal association between the peaks of cAMP, PDE2 and HWP1 mRNA, and the emergence of germ tubes is diagramed in FIG. 23. The rapid kinetics of the increase of PDE2 expression following germ tube induction may suggest that cAMP might be involved in the expression of PDE2, which may be supported by the absence of PDE2 upregulation in cap1/cap1 cells placed in germ tube inducing conditions.

The present invention also contemplates that the mechanism of cAMP activation of PDE2 may involve a cAMP response element (CRE) motif (−457TAACGTAA-450, the core sequence of the consensus CRE motif (TGACGTCA)) (Nehlin et al., 20 NUCL. ACIDS RES. 5271-5278 (1992)) in the 5' UTR of C. albicans PDE2 promoter. Therefore, it is possible that PDE2 expression may be induced in response to the increase of cAMP during bud-hypha transition through the interaction of CRE-binding (CREB) protein to the CRE-like site in the PDE2 promoter. A similar mechanism involving cAMP-driven upregulation of a phosphodiesterase gene through a CRE in the promoter has been described in mammalian cells (Le Jeune et al., 277 J. BIOL. CHEM., 35980-35989 (2002)). In mammalian cells, many hormones can induce cAMP-related genes through CREB protein phosphorylated by PKA (Gonzalez and Montminy, 59 CELL 675-680 (1989); Lee et al., 9 EMBO 4455-4465 (1990); and Montminy and Bilezikjian, 328 NATURE 175-178 (1987)). The possibility that C. albicans has a CREB protein is supported by the presence of a CREB protein, Sko1p, in S. cerevisiae, which represses osmoinducible genes by binding to CRE motifs (Nehlin et al., supra; Pascual-Ahuir et al., 276 J. BIOL. CHEM. 37373-37378 (2001); and Proft and Serrano, 19 MOL. CELL BIOL. 537-546 (1999)). It is also possible, however, that activity of Pde2 may be induced by phosphorylation by PKA as has been shown for Pde1 (Ma et al., 10 MOL. CELL BIOL. 91-104 (1999)). Several potential phosphorylation sites for PKA (T-26, T-65, S-129, S-209, T-266, S-295, S436, and S-473) were found to exist in C. albicans Pde2 (see, World Wide Web at atbs.dtu.dk/databases/PhosphoBase/predict/predform.html). Defects in germ tube formation that are as severe as those in the cap1/cap1 mutant when PDE2 is overexpressed also may imply that Pde2 activity may be closely coupled to cAMP synthesis to achieve normal expression of target genes of the cAMP-dependent signaling pathway.

The present invention also illustrates that the absence of increased PDE2 mRNA during germ tube inducing conditions in the cap1/cap1 mutant may suggest that not only is cAMP synthesis impaired by virtue of the absence of the CAP1 gene, but that cAMP degradative activity may also be reduced. Pde2 activity, however, is not reduced enough to keep cAMP levels sufficient for germ tube formation in the cap1/cap1 mutant. Therefore, the present invention shows that Pde2 activity may be present in the cap1/cap1 mutant because cap1/cap1 pde2/pde2 double mutants produce normal germ tubes in liquid media and are hyperfilamentous in solid media. Furthermore, the present invention suggests that the avirulence of the pde2/pde2 mutant may be a result of the detrimental effects of hyperactivation of the cAMP-signaling pathway, but avirulence may also be manifested through attributes of filamentation itself. The hyperfilamentous phenotype with reduced bud formation may hinder the organisms from effectively disseminating into various anatomical sites of the host. This idea is supported by the reduced virulence of mutants with disruptions in NRG1 and RFG1, which are avirulent (Kadosh and Johnson, 21 MOL. CELL BIOL. 2496-2505 (2001); and Murad et al., 20 J. EMBO 4742-4752 (2001)).

Increases in cAMP levels under conditions used in the present invention were directly correlated with bud-hypha transitions and were not simply a response to the presence of fresh media. Comparable cultures placed under conditions supporting budding growth did not show cAMP level increases. The results of the present invention agree with earlier reports of increases in cAMP levels prior to and accompanying germ tube formation (Chattaway et al., 123 GEN. MICROBIOL. 233-40 (1981); Cho et al., 30 J. MED. VET. MYCOL. 35-42 (1992); Niimi et al., supra). In accord with the present invention, cAMP levels are generally found to be low in budding yeasts that are used to induce germ tubes, except for one study (Egidy et al., 13 EXP. MYCOL. 428-32 (1989)) that reported basal cAMP levels to be three-fold higher than in the other studies at time zero. However, cAMP levels dropped within 15 minutes to levels that were consistent with time zero values of the other studies prior to rising. Reasons for the differences are unknown, but use of late stationary phase yeasts (96 hours) to induce germ tubes might have contributed to the high cAMP levels at time zero.

The ability of the majority of cap1/cap1 mutant cells to produce hyphae upon prolonged incubation in serum is consistent with a role for cAMP in germ tube formation. An increased length of time may be required to accumulate threshold levels of cAMP in cap1/cap1 mutant cells that are unable to generate pulses of cAMP, but are able to generate cAMP at reduced rates independent of Cap1. The existence of mechanisms independent of Cap1 with lesser effects on cAMP levels is shown by the small increase in cAMP in the cap1/cap1 mutant in germ tube induction conditions. Also, cAMP levels in middle logarithmic phase cultures of cap1/cap1 and CAP1 strains were similar indicating that, as is found for S. cerevisiae (Fedor-Chaiken et al., supra), basal levels of cAMP are not under Cap1 control in C. albicans. Steroid hormones (Kinsman et al., 31 MYCOSES 617-26 (1988)) and unidentified factors of low molecular weight in serum and seminal fluid that promote hyphal formation (Feng et al., 181 J. BACTERIOL. 6339-46 (1999); Barlow et al., 82 Pt. 2 J. GEN. MICROBIOL. 261-72 (1974)) may interact with C. albicans G protein-coupled receptors leading to Cap1 independent cAMP responses in C. albicans. Even cAMP itself which is present in serum at low levels (Kawarabayashi et al., supra) may work in combination with other factors to promote delayed hyphae formation in serum in cap1/cap1 mutant cells. Superior hyphae-inducing properties of serum relative to other conditions have been noted by others (Castilla et al., 10 CELL SIGNAL 713-9 (1998), Feng et al., supra, Lo et al., 90 CELL 939-49 (1997)). Reasons for the formation of hyphae, albeit at low frequencies, upon prolonged incubation in saliva and M199 without serum are also unknown but may reflect cell cycle influences on the bud-hypha transition (Loeb et al., 19 MOL. CELL. BIOL. 4019-27 (1999)).

As described in the present invention, the availability of the cap1/cap1 mutant that grows in yeast forms under hypha-inducing conditions clearly showed for the first time that cAMP profoundly affects bud-hypha transitions and filamentous growth in C. albicans. For strains with CAP1 genes, the role of cAMP was difficult to detect because of the filamentous appearance of wild-type colonies. Addition of cAMP or its membrane permeable derivative, dbcAMP, to the cap1/cap1 mutant in agar media promoted growth as filamentous rather than yeast colonies. Filamentous growth of the cap1/cap1 mutant in the presence of dbcAMP was not quite as extensive as for CAP1 strains. Insufficient uptake or rapid degradation of exogenous cAMP or dbcAMP of cap1/cap1 cells might have led to incomplete restoration of filamentous growth. In S. cerevisiae, the ability to take up cAMP is greatly enhanced by the presence of at least one "cam" mutation. Without at least one cam mutation, strains having mutations in the gene encoding adenylate cyclase, CYR1, cannot survive. One of the cam mutations causes a loss of PDE function, whereas the others are uncharacterized (Griffioen, et al., 275 J. BIOL. CHEM. 1449-56 (2000); Hall et al., 17 EMBO J. 4370-8 (1998)). By analogy with S. cerevisiae, disruption of the C. albicans PDE2 should generate strains with enhanced filamentous growth properties (Kübler et al., supra; Lorenz and Heitmann, supra; Pan and Heitman, supra).

The positive correlation between addition of cAMP and filamentous growth in both S. cerevisiae and C. albicans along with the requirement of CAP for filamentous growth of *S. cerevisiae* suggests that the cAMP-dependent signaling pathway of *S. cerevisiae* during pseudohyphal growth is a good working model for the *C. albicans* cAMP-dependent signaling pathway during bud-hypha transitions. Gpr1-Gpa1 regulation of cAMP signaling may be also conserved in *C. albicans*. A Gpr1 homologue with 43% identity in the first five transmembrane regions and an overall identity of 19% to *S. cerevisiae* Gpr1 was found in the *C. albicans* genome, as was a Gpa2 homologue (CAG99) with overall identity of 43% to *S. cerevisiae* Gpa2. *C. albicans* Ras1 is strongly implicated in cAMP signaling by its 50% identity to Ras2 of *S. cerevisiae*, which interacts with CAP and affects cAMP levels. Importantly the phenotype of ras1/ras1 null mutants of *C. albicans* is very similar to that of the cap1/cap1 mutant, with defective bud-hypha transitions and filamentous growth in all hypha-inducing conditions investigated including both liquid and solid media containing serum at 37° C. The similarity in phenotypes between *C. albicans* ras1/ras1 mutants and cap1/cap1 mutants teach that *C. albicans* RAS1 acts in the same signal transduction pathways as CAP1, the cAMP-dependent signaling pathway (Feng et al., supra). Phenotypic similarities also potentially connect a recently identified cdc2-related kinase CRK1 (Chen et al., 20 MOL. CELL. BIOL. 8696-708 (2000)), to CAP1 and RAS1. Null mutants in the CRK1 gene have a profound defect in hyphal development in all media tested, and express reduced amounts of hypha-specific genes under germ tube inducing conditions. The present invention also describes reduced amounts of HWP1 expression in cap1/cap1 mutants. Crk1 has been reported to be one of the downstream targets of Ras 1 in hyphal development of *C. albicans*. The transcription factors in *C. albicans* targeted by cAMP signaling are less clear. Crk1 and Ras1$^{V13}$ suppress the defects in hypha production of *C. albicans* cph1/cph1 efg1/efg1 pointing to the presence of an unknown transcription factor(s) that serves as a downstream target of cAMP signaling. Expression of *C. albicans* CRK1 gene in *S. cerevisiae* led to enhanced filamentous growth that was dependent on Flo8, a PKA-dependent transcription factor. But a homologue of Flo8 has not been found in the *C. albicans* genome. Another part of the cAMP signaling pathway that is poorly understood involves PKA. Unlike cap1/cap1 and ras1/ras1 mutants, defective germ tube formation is not seen at 37° C. on solid media in *C. albicans* strains lacking TPK2 encoding the catalytic subunit of PKA. Whether additional TPK genes with differing effects on filamentous growth, as is found in *S. cerevisiae* (Pan and Heitman, supra), are present in *C. albicans* is unknown. A gene encoding the regulatory subunit of PKA has been identified in the *C. albicans* genome.

Defects in hypha formation have been reported for a growing list of null mutants in signal transduction pathway genes. However, the media and temperatures that are required to detect the phenotype for most genes are limited compared to the cap1/cap1 mutant. Null mutants devoid of any one of many other signal transduction pathway genes such as COS1, SSK1, mitogen-activated protein kinase (MAPK) genes (CST20, HST7, CEK1, CPH1), have media-conditional deficiencies in filamentous growth. Strains with mutations of both alleles of the MAPK genes are unable to produce filamentous growth in solid Spider media but make normal hyphae in all other solid or liquid media tested (Csank et al., 66 INFECT. IMMUN. 2713-21 (1998); Kohler and Fink, 93 PROC. NATL. ACAD. SCI. USA 13223-8 (1996); Liu et al., 266 SCIENCE 1723-6 (1994)). The COS1 and SSK1 genes encoding proteins involved in a two-component signaling pathway are required for hyphal development in solid but not in liquid media (Alex et al., 95 PROC. NATL. ACAD. SCI. USA 7069-73 (1998); Calera et al., 68 INFECT. IMMUN. 518-25 (2000)). The phenotypes of cap1/cap1 mutant, ras1/ras1 and crk1/crk1 mutants suggests that defective hypha-formation in serum-containing medium at 37° C. provides a means for identifying proteins involved in the cAMP-dependent pathway.

Genetic studies of *S. cerevisiae* implicate two roles for CAP, one as a positive regulator of cAMP levels and a second role as a cytoskeletal regulator. The N-terminal third of CAP is responsible for binding adenylyl cyclase and thus regulates cAMP levels, while the widely conserved C-terminal domain of CAP has been shown to sequester monomeric actin, decreasing actin incorporation into actin filaments (Freeman et al., 270(10) J. BIOL. CHEM. 5680-5 (1995); Freeman et al., 16(2) MOL. CELL. BIOL. 548-56 (1996)). Additionally, a recent study on *Drosophila* and yeast oogenesis has demonstrated that CAP also has a role in oocyte polarity. Both in *Drosophila* and yeast, CAP mutants failed to establish the proper, asymmetric distribution of mRNA determinants with the oocyte (Baum and Perrimon, 10(16) CURR. BIOL. 964-73 (2000)).

Although structural features of *C. albicans* Cap1 predict cytoskeletal interactions, phenotypic analyses indicate that *C. albicans* Cap1 differs from other CAPs in influencing cytoskeletal functions. None of the phenotypes of cap mutants of *S. cerevisiae* attributable to the carboxy terminal cytoskeletal-interacting domain of CAP (inability to grow on rich medium, temperature sensitivity, inviability in response to nitrogen starvation and swollen yeast cell morphology) (Field et al., 61 CELL 319-27 (1990)) or those of *S. pombe* (temperature sensitivity and abnormal cellular morphology) (Kawamukai et al., supra) were found for *C. albicans* cap1/cap1 mutants. Cap1 is required for normal hyphal development under all conditions examined. However, the ability of cap1/cap1 mutants to form germ tubes after a delay, and correction of the phenotype by exogenous cAMP and dbcAMP indicated that modulation of cAMP levels, and not cytoskeletal interactions, was responsible for the hypha-promoting effect of Cap1 in *C. albicans*. This result is consistent with studies in *S. cerevisiae* showing that neither targeting of CAP to actin cortical patches through the SH3 binding domain, nor interaction of CAP with actin monomers is necessary for CAP to transduce cAMP signals (Yu et al., supra; Zelicof et al., supra).

The absence of the growth defects and aberrant budding phenotypes in *C. albicans* cap1/cap1 mutants compared to *S. cerevisiae* and *S. pombe* cap null mutants points to possible differences in Cap protein-actin interactions that may related to the capacity of *C. albicans* but not the other yeasts to form germ tubes and true hyphae (Field et al., supra; Kawamukai et al., supra). Although related, pseudohyphal formation and true hyphal formation are distinct processes that are characterized both by morphological differences and differences in gene expression patterns in *C. albicans*. Cap1 may be in part responsible for the morphological differences between germ tubes and pseudohyphae. In *S. cerevisiae*, the interaction of CAP with actin monomers through the 27 carboxy terminal amino acids (Zelicof et al., supra) may prevent hyperpolarization and accentuated concentration of actin filaments seen in buds of cap null mutants (Baum and Perrimon, supra). However filamentous actin is highly concentrated at the hyphal tip in *C. albicans* germ tubes and true hyphae (Anderson and Soll, 132 J. GEN. MICROBIOL. 2035-47 (1986)). Growth from hyphal tips may require weaker interactions between Cap1 and actin in *C. albicans* compared to *S. cerevisiae* to facilitate polarized growth during germ tube and hyphae formation. The results suggest that CAP function is not required for cytoskeletal organization in *C. albicans* as it is in *S. cerevisiae*.

The mechanism of Cap1-mediated modulation of bud-hypha transitions and filamentous growth is unknown. Studies with *S. cerevisiae* suggest that the cAMP-dependent pathway causes cells to undergo unipolar budding, a process that, when coupled with elongated growth controlled by the MAPK kinase pathway, produces pseudohyphal cells (Pan and Heitman, supra). Mösch and Fink (145 GENETICS 671-84 (1997)) reported that the *S. cerevisiae* CAP/SRV2 mutant constructed by transposon mutagenesis is defective in pseudohyphal growth and undergoes random budding. These reports prompt the idea the *C. albicans* Cap 1 may function to interrupt processes important for budding, and that interruption of budding processes is required for bud-hypha transitions and filamentous growth.

Phenotypes of cap1/cap1 mutants also differed from *C. albicans* strains with mutations in a gene that functions in cytoskeletal regulation and is aberrant in both budding and hyphal morphologies (Leberer et al., 7 CURR. BIOL. 539-46 (1997)). The lack of a role for *C. albicans* Cap1 in cytoskeletal organization may represent an important attribute for resisting stresses such as nitrogen limitation. Whereas *C. albicans* appears similar to *S. cerevisiae* in employing the RAS/cAMP pathway for producing filamentous growth on SLAD media (Gimeno et al., supra, Pan and Heitman, supra) *S. cerevisiae* cap mutants are non-viable in limiting nitrogen (Field et al., supra). In contrast, *C. albicans* cap1/cap1 mutants survive as budding yeasts when nitrogen is limiting.

The divergent phenotypes of cap mutants in *S. cerevisiae* and *S. pombe* illustrate that CAP genes play a key role in the variable responses of different fungi to similar environmental conditions. The primary role of CAP1 in *C. albicans* may be to mediate rapid induction of bud-hypha transitions in response to a variety of environmental conditions, a hallmark of *C. albicans* growth. The finding that cap1/cap1 mutants are avirulent in a murine model of systemic candidiasis, as described in the present invention, suggests that antifungal strategies interfering with *C. albicans* CAP1-mediated signaling are important for preventing or inhibiting candidiasis (PCT/US02/06986).

The environmental cues that activate bud/hypha signaling cascades are unknown, but historical data strongly suggest that nitrogen regulatory circuits are involved. In many fungi, nitrogen utilization is important not only for the synthesis of essential metabolites, but also for interconversion between growth morphologies that are important for environmental adaptation. Spore germination in *Aspergillus* and *Rhizopus* is preferentially induced in poor nitrogen sources such as proline (Weber et al., 55 PHYTOPATH. 262-6 (1965); Yanagita, 26 ARCH. MICROBIOL. 329-44 (1957)). In diploid strains of *S. cerevisiae*, nitrogen starvation or use of proline as a nitrogen source leads to production of pseudohyphal cells which invade solid agar, and are thought to be necessary for growth in the natural environment (Gimeno et al., 68(6) CELL 1077-90 (1992)). In *C. albicans*, the use of proline or selected other amino acids induces production of true hyphae, as well as pseudohyphae from yeast forms (Dabrowa et al., 13 INFECT. IMMUN. 830-5 (1976); Holmes et al., 133 J. GEN. MICROBIOL. 3219-28 (1987); Land et al., 11(5) INFECT. IMMUN. 1014-23 (1975)). Morphologic variation in response to proline is also found in plant pathogenic fungi and is thought to be important for pathogenesis (Kulkarni et al., 5 EXP. MYCOL. 148-54 (1981)). Thus morphologic variation that accompanies the use of nitrogen sources is a common feature of fungal growth.

The control of nitrogen supply by prokaryotic and eukaryotic organisms is highly regulated. Fungi are able to utilize an array of compounds as nitrogen sources, and have evolved the capability to express different catabolic enzymes to make nitrogen available to the cell. Nitrogen metabolism regulation has been well studied in *S. cerevisiae, Aspergillus nidulans*, and *Neurospora crassa*. When preferred sources of nitrogen such as ammonia, glutamine, and glutamate are not available or are in concentrations too low to support growth, the synthesis of pathway-specific catabolic enzymes and permeases are derepressed (Marzluf, 61(1) MICROBIOL. MOL. BIOL. REV. 17-21 (1997)). Activating global regulatory genes in *Aspergillus* (areA; Caddick, MOLECULAR BIOLOGY OF FILAMENTOUS FUNGI 141-52 (1992), Kudla et al., 9(5) EMBO J. 1355-64 (1990)), Neurospora (nit-2; Fu et al., 7(5) MOL. CELL. BIOL. 1691-6 (1987); Stewart et al., 46(2-3) GENE 291-5 (1986)), *Saccharomyces* (gln-3; Minehart et al., 11(12) MOL. CELL. BIOL. 6216-28 (1991)), and *Penicillum* (nre; Haas et al., 27(2) CURR. GENET. 150-8 (1995)) have been found that code for GATA-type zinc finger transcription factors which activate specific catabolic genes when preferred nitrogen sources are lacking. These regulatory proteins all have a conserved DNA binding domain, which consists of a single $Cys_2/Cys_2$-type zinc finger motif with a central loop of 17 amino acid residues (Marzluf, supra). The amino acid conservation in the DNA binding region is high among the different members of this GATA family. Mutations of conserved residues in the DNA binding domains of NIT2 or AREA lead to complete lack of DNA binding in vitro and are nonfunctional in vivo (Fu et al., 4(11) MOL. MICROBIOL. 1847-52 (1990)).

An embodiment of the present invention relates to various methods for altering the expression of one or more genes associated with the regulation of the cAMP-PKA signaling pathway in *C. albicans*, resulting in the interference of the virulence properties and disrupting the morphological transitions of *C. albicans*. In particular, the *C. albicans* virulence properties may include, but are not limited to, adhesive properties, invasive properties (e.g., ability to degrade extracellular matrix proteins and ability to block neutrophil oxygen radical production and degranulation) and proliferative properties. Additionally, the disruption of *C. albicans* morphological transitions comprises the transition from the budding form to the hyphal growth form.

In a particular embodiment, the present invention teaches methods for altering gene expression of one or more genes associated with regulation of the cAMP-PKA pathway by interfering with the regulation of transcription of these genes. In particular, the present invention teaches interfering with the regulation of transcription of the gene PDE2 alone or with the CAP1 gene. Initiation of transcription control may be mediated by cis-acting sequences, termed gene response elements that interact with DNA binding proteins to repress or activate transcription in response to environmental signals. Upstream Activating Sequence (UAS) and Upstream Regulatory Sequence (URS) elements may serve to activate or repress gene expression though interactions with DNA binding proteins. In a particular embodiment of the present invention, the cis-regulatory element comprises a cAMP response element (CRE) located in the promoter region of the PDE2 gene.

The present invention also teaches the identification of additional cis-acting sequences present on the genes associated with the regulation of the cAMP-PKA pathway. UAS and URS may be identified by fusing the DNA upstream of a gene coding regions to a reporter gene whose protein level can be easily measured. URS elements may be identified by increased reporter gene expression relative to the intact DNA upon deletion of the element. Conversely, UAS elements required for expression may be identified by a loss of reporter gene activity upon deletion of the element. A second approach for identifying UAS elements is to design individual, overlapping bp sequence elements spanning the entire DNA sequence, and then look for activation of reporter gene expression relative to a simple promoter containing a TATA element (Guarente & Ptashne, 78(4) PROC. NATL. ACAD. SCI. USA 2199-203 (1981); Rupp et al. 18(5) EMBO J. 1257-69 (1999)).

In an alternate embodiment of the present invention, gene expression may be disrupted by interfering with DNA binding proteins (BP) that bind to cis-regulatory elements. In particular, the DNA BP may comprise the CRE binding protein, which may bind to the CRE associated with the PDE2 gene. The transcriptional regulation of gene expression through cis-acting sequences may be controlled by DNA binding proteins (Schleif, 241(4870) SCIENCE 1182-87 (1988)). Evidence for the presence of unknown DNA binding proteins may be provided by electrophoretic mobility shift assays, where proteins in crude nuclear extracts of cells growing in appropriate conditions are assayed for their ability to retard the migration of labeled UAS or URS elements in polyacrylamide gels. Mutations or deletions in the UAS may be employed to verify the specificity of the interactions of DNA binding proteins with the UAS element and to map the most important nucleotides for DNA binding. The presence of unknown binding proteins to UAS elements provides the groundwork for cloning genes encoding regulatory proteins.

The present invention also teaches the identification of additional proteins that bind to cis-acting sequences present on the genes associated with the regulation of the cAMP-PKA pathway. Several strategies may be used to clone genes encoding proteins that bind to UAS elements. A particular method may be to use DNA affinity beads that comprise of UAS elements that have incorporated biotinylated nucleotides to facilitate coupling to streptavidin beads (Gabrielsen & Huet, 218 METHODS ENZYMOL. 508-25 (1993)). Nuclear extracts may then be incubated with the beads to separate the desired DNA binding proteins from other proteins in the extract, followed by elution of the DNA binding protein from the beads, purification on SDS polyacrylamide gels and amino acid sequencing of HPLC-purified proteolytic fragments. The amino acid sequences may then be used to design degenerate primers for amplification of a PCR product from cDNA to be used as a probe in library screening to obtain the DNA binding protein gene. Verification of the biological activity of the DNA binding protein may be gained from creating null mutants in the gene and looking for loss of expression of the reporter gene under the control of the specific UAS elements used to identify and characterize the protein. The pattern of expression of the DNA binding protein gene itself, along with the predicted primary amino acid sequence, may provide insight into regulatory mechanisms. Predictions about whether expression is mediated by transcription, or by protein modification, are possible. In the event that the DNA binding protein gene is regulated by transcription, its non-flanking regions provide material for identification of cis-acting regulatory regions.

The present invention also teaches the expression of the PDE2 gene and the construction of a pde2/pde2 mutant. pde2/pde2 mutants may be generated through the disruption of the PDE2 gene. Disruption of the PDE2 gene may be accomplished by the construction of a disruption cassette followed by site-specific recombination targeted to genomic PDE2 nucleic acid sequences, resulting in PDE2 gene inactivation. In an alternative embodiment, the present invention teaches a PDE2 and/or CAP1 complemented strain of C. albicans. Complementation of pde2/pde2 mutants may be achieved through co-transformation with a PCR product containing wild type PDE2 and/or CAP1 DNA and the disruption cassette.

Another embodiment of the present invention teaches the expression of the CAP1 gene (SEQ ID NO. 2) and the construction of a cap1/cap1 mutant. cap1/cap1 mutants may be generated through the disruption of the CAP1 gene. Disruption of the CAP1 gene may be accomplished by the construction of a disruption cassette followed by site-specific recombination targeted to genomic CAP1 nucleic acid sequences, resulting in CAP1 gene inactivation. In an alternative embodiment, the present invention teaches a PDE2 and/or CAP1 complemented strain of C. albicans. Complementation of cap1/cap1 mutants may be achieved through co-transformation with a PCR product containing wild type PDE2 and/or CAP1 DNA and the disruption cassette.

A further embodiment of the present invention teaches the generation of pde2/pde2 cap1/cap1 mutant. The generation of the pde2/pde2 cap1/cap1 mutant may be obtained by construction of a disruption cassette targeted to genomic PDE2 and CAP1 nucleic acid sequences, followed by site-specific recombination. Further, the present invention also teaches a PDE2 and/or CAP1 complemented strain of C. albicans. Complementation of pde2/pde2 cap1/cap1 mutants may be achieved through co-transformation with a PCR product containing wild type PDE2 and/or CAP1 DNA and the disruption cassette. Another embodiment of the present invention teaches the overexpression of PDE2 and/or CAP1.

An additional embodiment of the present invention relates to the use of a PDE2 and/or CAP1 binding partner to treat or prevent the bud-hypha morphogenic transition associated with C. albicans virulence. Accordingly, in one embodiment, the present invention provides a composition comprising at least one Pde2 and/or Cap1 binding partner. The Pde2 and/or Cap1 binding partner may comprise a polynucleotide Pde2 and/or Cap1 binding partner. In another embodiment, the polynucleotide Pde2 and/or Cap1 binding partner may comprise an antisense oligonucleotide Pde2 and/or Cap1 binding partner. In another embodiment, the polynucleotide Pde2 and/or Cap1 binding partner may comprise a ribzyme Pde2 and/or Cap1 binding partner.

Alternatively, a Pde2 and/or Cap1 binding partner may comprise a polypeptide Pde2 and/or Cap1 binding partner. In one embodiment, the polypeptide Pde2 and/or Cap1 binding partner comprises a peptide generated by rational design.

In another embodiment, the polypeptide Pde2 and/or Cap1 binding partner comprises an immunoglobulin or a functional equivalent thereof. In a specific embodiment, the polypeptide Pde2 and/or Cap1 binding partner is an immunoglobulin that specifically binds Pde2 and/or Cap1. The term "immunoglobulin" is used herein in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. In one embodiment, the subject immunoglobulins comprise at least one human constant domain. In another embodiment, the Pde2 and/or Cap1 immunoglobulins comprise a constant domain that exhibits at least about 90-95% sequence identity with a human constant domain and yet retains human effector function.

An immunoglobulin Pde2 and/or Cap1 binding partner or functional equivalent thereof may be human, chimeric, humanized, murine, CDR-grafted, phage-displayed, bacteria-displayed, yeast-displayed, transgenic-mouse produced, mutagenized, and randomized. In a specific embodiment, the immunoglobulin Pde2 and/or Cap1 binding partner or functional equivalent thereof binds an epitope of the extracellular domain of Pde2 and/or Cap1 as expressed in *C. albicans*.

In another embodiment, the Pde2 and/or Cap1 binding partner may be a peptide generated by rational design or by phage display. See, e.g., WO 98/35036. In one embodiment, the peptide may be a "CDR mimic" or antibody analogue based on the CDRs of an antibody. Even though such peptides may have the ability to, by themselves, decrease or affect the bud-hypha morphogenic transition of *C. albicans* characterized by the expression of Pde2 and/or Cap1, the peptide may be fused to a therapeutic agent to add or enhance the properties of the peptide.

Regardless of the type of Pde2 and/or Cap1 binding partner, a "substantially purifed" Pde2 and/or Cap1 binding partner is one that has been identified, separated and/or recovered from a component of its natural environment. Contaminant components of its natural environment are materials that would interfere with therapeutic uses for the Pde2 and/or Cap1 binding partner, and may include enzymes, hormones, and other proteinaceous or nonproteinaceous solutes. Ordinarily, an isolated binding partner will be prepared by at least one purification step. In one embodiment, the binding partner is purified to at least about 60%, at least about 65%, at least about 70%, at least about 75%, at least about 80%, at least about 85%, at least about 88%, at least about 90%, at least about 92%, at least about 95%, at least about 97%, at least about 98%, at least about 99%, at least about 99.9%, or at least about 99.99% by weight of Pde2 and/or Cap1 binding partner as determined, for example, by the Lowry method. Alternatively, the binding partner may be purified to a degree sufficient to obtain at least 15 residues of N-terminal or internal amino acid sequence by use of a spinning cup sequenator. In yet another embodiment, the binding partner is purified to homogeneity by SDS-PAGE under reducing or nonreducing conditions using Coomassie blue or silver stain.

Another embodiment of the present invention is the gene products of the PDE2 and CAP1 genes, Pde2 and Cap1 (SEQ ID NO. 1), respectively. Structural features of *C. albicans* Cap1 conform closely to adenylate cyclase associated proteins from other organisms (Field et al., supra; Kawamukai et al., supra; Matviw et al., supra; Vojtek and Cooper, supra; Zelicof et al., 271 J. BIOL. CHEM. 18243-52 (1996)) and similarily, a highly conserved phosphodiesterase signature sequence is present in *C. albicans* Pde2 and *C. albicans* pde2/pde2 mutants have similar phenotypes as the pde2/pde2 mutants of *S. cerevisiae* (Harashima et al., 10 MOL. CELL 163-73 (2002); Toda et al., 40 CELL 27-36 (1985); Wilson et al., 325 FEBS 191-5 (1993)). Amino- and carboxy-terminal halves rich in alpha helices and beta-sheets, respectively, separated by a central loop containing a stretch of prolines are typical of CAPs that have two domains with separable functions. The SH3-binding motifs and the conserved actin-binding region at the carboxy terminus may interact with an Abp1 homologue and actin monomers in *C. albicans* as has been shown for similar regions of *S. cerevisiae* CAP (Freeman et al., 270 J. BIOL. CHEM. 5680-5 (1995); Freeman et al., 16 MOL. CELL. BIOL. 548-56 (1996); Lila and Drubin, 8 MOL. BIOL. CELL. 367-85 (1997); Yu et al., supra). An Abp1 homologue was found in the *C. albicans* genome. Differences in cAMP responses of the cap1/cap1 mutant compared to isogenic CAP1 strains suggest that Cap1 regulates adenylate cyclase activity. cAMP or its membrane permeable derivative, dbcAMP, partially restored filamentation and enhanced hyphae production of the cap1/cap1 mutant strain, further confirming that Cap1 acts through regulation of cAMP levels. CAP1 (SEQ ID NO. 2) encodes the adenylate cyclase associated protein (SEQ ID NO. 1) of *C. albicans*.

Another aspect of the present invention is the identification of new genes that are regulated by PDE2 and CAP1 controls because such genes are likely to be important in virulence. The null mutant of the putative DNA binding protein genes serves as a tool to achieve this goal as well, for identification of genes with low message levels compared to mRNA from cells with the wild-type DNA binding protein gene. A preferred methodology for the identification of new genes is genome-wide expression monitoring (DeRisi et al., 11(1) CURR. OPIN. ONCOL. 76-9 (1999)). The proven utility of genome wide expression monitoring in revealing previously unidentified genes that are up or down-regulated under any given environmental conditions has been demonstrate. For example, new sporulation-specific genes, and regulatory circuits were identified using genome-wide expression monitoring of the *S. cerevisiae* genome (Cox et al., 15(8) YEAST 703-13 (1999)). Mammalian genes in fibroblasts that are regulated in the presence of serum have also been identified using genome wide expression monitoring with the available but incomplete mammalian genome sequences (Iyer et al., 283(5398) SCIENCE 83-7 (1999)). In both cases, unexpected genes were identified underscoring the value of the technique. Similar studies are plausible using the *C. albicans* genome.

Opportunities for proliferation and invasion of mammalian hosts by *C. albicans* are continuing to increase. Because of the loss of the cellular component of the immune system, AIDS patients are susceptible to invasion of submucosal tissue by *C. albicans*. The frequency of candidal infections may also be a result of the prophylactic use of antibacterial drugs used in AIDS patients to minimize other opportunistic infections. Candidal infections increase in severity and recur more frequently as the immunodeficiency progresses. In non-AIDS patients, such as those undergoing organ transplantation, are neutropenic, or have debilitating diseases requiring advanced modalities of life support, mucosal and hematogenously disseminated candidiasis seriously threaten optimal treatment outcomes. While antifungal drugs can be effective, the increasing frequency of resistant strains of *C. albicans*, and the systemic side effects of the drugs prompts exploration of novel strategies to interrupt the sequence of events leading to disease and to expand the repertoire of antifungal drugs. By defining the molecular events leading to bud/hypha transition, and through the identification of new genes that are co-regulated with CAP1 in a putative global regulatory circuit, the present invention relates to new and novel ways to interfere with candidiasis. The long-term medical benefit(s) of this study may be the development of alternative or adjunctive therapies based on the expression of the PDE2 and CAP1 genes in *C. albicans*. Furthermore, better understanding of the role of PDE2 and CAP1 in *C. albicans* virulence and morphological transitions in multiple conditions shows that antifungal strategies interfering with *C. albicans* pde2- and Cap1-mediated signaling will be important for preventing or inhibiting candidates.

Recombinant Techniques

The DNA molecules of the present invention may be employed by recombinant techniques. Thus, for example, the DNA molecule sequence may be included in any one of a variety of expression vehicles, in particular vectors or plasmids for expressing such a polypeptide. Such vectors include: chromosomal, nonchromosomal and synthetic DNA sequences, e.g., derivatives of SV40; bacterial plasmids; phage DNA; yeast plasmids; vectors derived from combinations of plasmids and phage DNA; and viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art.

The DNA sequence in the expression vector may be operatively linked to an appropriate expression control sequence(s) (promoter) to direct mRNA synthesis. As representative examples of such promoters, there may be mentioned: LTR or SV40 promoter, the *E. coli*, lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably may contain a gene to provide a phenotypic trait for selection of transformed host cells such as dihydrofolate reductase or neomycin resistance for eukaryotic cell culture, or such as tetracycline or ampicillin resistance in *E. coli*.

An embodiment of the invention relates to an isolated DNA molecule comprising all or part of the nucleotide sequence of the PDE2 gene and/or CAP1 gene (SEQ ID NO. 2). This nucleotide sequence, or fragments or functional equivalents thereof, may be used to generate recombinant DNA molecules that direct the expression of the polypeptides of the present invention, or functionally active peptides or functional equivalents thereof, in appropriate host cells. Due to the degeneracy of the nucleotide coding sequence, other DNA sequences which encode substantially the same amino acid sequences as depicted, or analogs or fragments thereof, may be used in the practice of the invention for the cloning and expression of such a gene. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved and/or on the basis of crystallographic data. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

Techniques well known to those skilled in the art for the isolation of DNA, generation of appropriate restriction fragments, construction of clones and libraries, and screening recombinants may be used. For a review of such techniques, see, for example, SAMBROOK ET AL., MOLECULAR CLONING: A LABORATORY MANUAL, Chapters 1-18, ($2^{nd}$ ed. Cold Spring Harbor Laboratory 1989), the disclosure of which is hereby incorporated by reference. Also, the 5' untranslated and coding regions of the nucleotide sequence could be altered to improve the translational efficiency of the mRNA. In addition, based on X-ray crystallographic data, sequence alterations could be undertaken to improve protein stability, e.g., introducing disulfide bridges at the appropriate positions, and/or deleting or replacing amino acids that are predicted to cause protein instability. These are only examples of modifications that can be engineered to produce a more active or stable protein, more protein, or even change the substrate specificity of the protein.

The vector containing the appropriate DNA sequence, as well as an appropriate promoter or control sequence, may be employed to transform an appropriate host to permit the host to express the polypeptides of the present invention. Representative examples of appropriate hosts include: bacterial cells, such as *E. coli, Salmonella typhimurium, Streptomyces*; fungal cells, such as yeast; insect cells, such as *Drosophila* S2 and *Spodoptera* Sf9; animal cells, such as CHO, COS or Bowes melanoma; adenoviruses; and plant cells. The selection of an appropriate host and appropriate transformation technique is deemed to be within the scope of those skilled in the art.

More particularly, the present invention also includes recombinant constructs comprising one or more of the sequences of the present invention. The constructs may comprise a vector, such as a plasmid or viral vector, into which a sequence of the invention has been inserted, in a forward or reverse orientation. In a preferred aspect of this embodiment, the construct may further comprise regulatory sequences, including, for example, a promoter operably linked to the sequence. Large numbers of suitable vectors and promoters are known to those of skill in the art, and are commercially available. The following vectors are provided by way of example. Bacterial: pQE70, pQE60, pQE-9 (Qiagen, Valencia, Calif.), pBS, phagescript, psiX174, pBluescript SK, pBsKS, pNH8a, pNH16a, pNH18a, pNH46a (Stratagene, La Jolla, Calif.); pTRC99A, pKK223-3, pKK233-3, pDR540, PRIT5 (Pharmacia, Groton, Conn.). Eukaryotic: pWLneo, pSV2cat, pOG44, pXT1, pSG (Stratagene, La Jolla, Calif.); pSVK3, pBPV, pMSG, PSVL (Pharmacia, Groton, Conn.). However, any other plasmid or vector may be used as long as they are replicable and viable in the host.

In a further embodiment, the present invention teaches host cells containing the above-described construct. The host cell can be a higher eukaryotic cell, such as a mammalian cell, or a lower eukaryotic cell, such as a yeast cell, or the host cell can be a prokaryotic cell, such as a bacterial cell. The host cell preferably may secrete the recombinant protein. Introduction of the construct into the host cell can be effected by calcium phosphate transfection, DEAE-Dextran mediated transfection, or electroporation (DAVIS ET AL., BASIC METHODS IN MOLECULAR BIOLOGY (1986)).

Promoters

Suitable promoter regions can be selected from any desired gene using CAT (chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of skill in the art. The constructs in host cells can be used in a conventional manner to produce the gene product encoded by the recombinant sequence.

Enhancers

Transcription of a DNA encoding the polypeptides of the present invention by higher eukaryotes may be increased by inserting an enhancer sequence into the vector. Enhancers are cis-acting elements of DNA, usually from about 10 to about 300 bp, that act on a promoter to increase its transcription. Examples include the SV40 enhancer on the late side of the replication origin (base pair 100 to 270), a cytomegalovirus early promoter enhancer, a polyoma enhancer on the late side of the replication origin, and adenovirus enhancers.

Selectable Markers

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence may preferably be assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Expression Vectors

Useful expression vectors for bacterial use may be constructed by inserting a structural DNA sequence encoding a desired protein together with suitable translation, initiation and termination signals in operable reading phase with a functional promoter. The vector may comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis.). These pBR322 backbone sections are combined with an appropriate promoter and the structural sequence to be expressed.

Following transformation of a suitable host strain and growth of the host strain to an appropriate cell density, the selected promoter may be de-repressed by appropriate means (e.g., temperature shift or chemical induction) and cells may be cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Various mammalian cell culture systems can also be employed to express recombinant polypeptides. Examples of mammalian expression systems include the COS-7 lines of monkey kidney fibroblasts, described by Gluzman and other cell lines capable of expressing a compatible vector, for example, the C127, 3T3, CHO, HeLa and BHK cell lines (Gluzman, 23 CELL, 175 (1981)). Mammalian expression vectors may comprise an origin of replication, a suitable promoter and enhancer, and also any necessary ribosome binding sites, polyadenylation sites, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Microarrays

An embodiment of the present invention is a microarray containing at least one nucleotide sequence or fragment thereof, of the PDE2 gene alone or with the CAP1 gene. Such a microarray may be used to detect presence or absence of Pde2 alone or with Cap1 in a cell in context of a diagnostic kit. A further embodiment of the present invention is the use of diagnostic kit comprising the PDE2 gene alone or with the CAP1 gene for the determination of gene expression level of wild type strains versus mutant strains. The use of microarrays to monitor expression levels of a multiplicity of genes are known to those skilled in the art from references such as U.S. Pat. No. 6,040,138 issued to Affymetrix, Inc., and U.S. Pat. No. 6,004,755 issued to Incyte Pharmaceuticals, Inc., the disclosures of which are incorporated by reference herein in their entirety. For example, primers that hybridize to vector sequences are employed to amplify small genomic inserts that are robotically spotted on membranes to generate mini-arrays. In any given sample, DNA or RNA samples are labeled with a fluorescent dye and then hybridized to a DNA microarray containing hundreds to thousands of DNA sequences. DNA sequences may be selected from cDNA libraries, genomic DNA, or expressed sequence tags (ESTs). Subsequent spotting or printing onto the matrix is followed by DNA crosslinking to the matrix. The fluorescence intensities of the microarray are analyzed, and these measurements are then used to assess gene expression of a particular gene within the sample.

The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are herein incorporated by reference. For microarrays requiring the use of cDNA probes, DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents.

Means of detecting labeled sample nucleic acids hybridized to the probes of the microarray are known to those skilled in the art. Thus, for example, visualization of colorimetric label is sufficient whereas detection of radiation (e.g., with photographic film or a solid state detector) is necessary for radioactive labeled probes. Fluorescent labeled nucleic acids may be detected with fluorescent microscopy. The hybridized array is excited with a light source at the excitation wavelength of the particular fluorescent label and the resulting fluorescence at the emission wavelength is detected. Automated fluorescent microscopy systems are described in U.S. Pat. No. 5,143,854, and International PCT Application WO 00/63,442, the disclosures of which are herein incorporated by reference.

One skilled in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location on the microarray (e.g., where the label is a fluorescent label, detection of the amount of fluorescence produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

The above described gene expression profiles of thousands of genes can now be examined en masse via cDNA and oligonucleotide microarrays (Shalon et al., 46 PATHOL. BIOL. 107-9 (1998); Lockhart et al., NUCL. ACIDS SYMP. SER. 11-2 (1998); Schena et al., 16 TRENDS BIOTECHNOL. 301-306 (1998)). Gene expression profiles in yeast, mammalian cell lines, and disease tissues have recently been studied (Cho et al., 2 MOL. CELL. 65-73 (1997); Schena et al., 93 PROC. NATL. ACAD. SCI. USA 10614-9 (1996); Heller et al., 94 PROC. NATL. ACAD. SCI. USA 2150-5 (1997); Welford et al., 26 NUCL. ACIDS RES. 3059-65 (1998)).

Given the high significance of the identification of new genes with potential importance in virulence in an organism where random mutagenesis approaches are not possible, exploration of alternatives other than genome wide expression monitoring are also warranted. Consequently, a "work-around" method that does not require the production of gene-specific probes may be utilized. Primers that hybridize to vector sequences are employed to amplify small genomic inserts that are robotically spotted on membranes to generate mini-arrays. This array method is being used for genome wide expression monitoring in *H. capsulatum*. The null mutant of the PDE2 gene alone or with the CAP1 gene may serve as a tool to achieve this goal as well, for identification of genes with low message levels compared to mRNA from cells with the wild-type PDE2 gene and/or CAP1 gene. A methodology for the identification of new genes is genome wide expression monitoring. DeRisi & Iyer, 11(1) CURR. OPIN. ONCOL. 76-79 (1999). The proven utility of genome wide expression monitoring in revealing previously unidentified genes that are up or down-regulated under any given environmental conditions has been demonstrated multiple times. For example, new sporulation-specific genes, and regulatory circuits were identified using genome-wide expression monitoring of the *S. cerevisiae* genome (Cox et al., 15(8) YEAST 703-13 (1999)). Mammalian genes in fibroblasts that are regulated in the presence of serum have also been identified using genome wide expression monitoring with the available but incomplete mammalian genome sequences (Iyer et al., 283(5398) SCIENCE 83-87 (1999)). In both cases, unexpected genes were identified underscoring the value of the technique. Similar studies are plausible using the *C. albicans* genome. The sequence of the *C. albicans* genome has been completed to five times coverage.

Gene Therapy

Another embodiment of the present invention involves the use of gene therapy applications, which will interfere with the transcription of *C. albicans* PDE2 gene alone or with the CAP1 gene. Gene therapy has been broadly defined as "the correction of a disease phenotype through the introduction of new genetic information into the affected organism" (Roemer et al., 208 EUR. J. BIOCHEM. 211-25 (1992)). Two basic approaches to gene therapy have evolved: (1) ex vivo gene therapy and (2) in vivo gene therapy. In ex vivo gene therapy, cells are removed from a subject and cultured in vitro. A functional replacement gene is introduced into the cells (transfection) in vitro, the modified cells are expanded in culture, and then re-implanted in the subject. These genetically modified, re-implanted cells are reported to secrete detectable levels of the transfected gene product in situ (Miller, 76 BLOOD 271-8 (1990)) and Selden et al., 317 NEW ENG. J. MED. 1067-76 (1987)). The development of improved retroviral gene transfer methods (transduction) facilitates the transfer into and subsequent expression of genetic material by somatic cells (Cepko et al., 37 CELL 1053-62 (1984)). Accordingly, retrovirus-mediated gene transfer has been used in clinical trials to mark autologous cells and as a way of treating genetic disease (Rosenberg et al., 323 NEW ENG. J. MED. 570-8 (1990); Anderson, 2 HUMAN GENE THER. 99-100 (1991)). Several ex vivo gene therapy studies in humans are reported (reviewed in Anderson, 256 SCIENCE 808-13 (1992) and Miller, 357 NATURE 455-60 (1992)).

In in vivo gene therapy, target cells are not removed from the subject. Rather, the transferred gene is introduced into cells of the recipient organism in situ, that is, within the recipient. In vivo gene therapy has been examined in several animal models (reviewed in Felgner et al., 349 NATURE 351-2 (1991)). Publications have reported the feasibility of direct gene transfer in situ into organs and tissues such as muscle (Ferry et al., 88 PROC. NATL. ACAD. SCI. 8377-781 (1991); Quantin et al., 89 PROC. NATL. ACAD. SCI. USA 2581-4 (1992)), hematopoietic stem cells (Clapp et al., 78 BLOOD 1132-9 (1991)), the arterial wall (Nabel et al., 244 SCIENCE 1342-4 (1989)), the nervous system (Price et al., 84 PROC. NATL. ACAD. SCI. USA 156-60 (1987)), and lung (Rosenfeld et al., 252 SCIENCE 431-4 (1991)). Direct injection of DNA into skeletal muscle (Wolff et al., 247 SCIENCE 1465-8 (1990)), heart muscle (Kitsis et al., 88 PROC. NATL. ACAD. SCI. USA 4138-42 (1991)) and injection of DNA-lipid complexes into the vasculature (Lim et al., 83 CIRCULATION 2007-11 (1991); Ledere et al., 90 J. CLIN. INVEST. 936-44 (1992); Chapman et al., 71 CIRC. RES. 27-33 (1992)) also have been reported to yield a detectable expression level of the inserted gene product(s) in vivo.

Gene therapy efforts have been aimed at the identification of various cell types for transformation, including keratinocytes (Morgan et al., 237 SCIENCE 1476-9 (1987)); fibroblasts (Palmer et al., 88 PROC. NATL. ACAD. SCI. USA 1330-34 (1991); Garver Jr. et al., 237 SCIENCE 762-4 (1987); International PCT Application WO 92/15,676); lymphocytes (Reimann et al., 89 J. IMMUNOL. METH. 93-101 (1986)); myoblasts (Barr et al., 254 SCIENCE 1507-9 (1991); Dai et al., 89 PROC. NATL. ACAD. SCI. 10892-5 (1992); Roman et al., 18 SOM. CELL MOL. GEN. 247-58 (1992)); smooth muscle cells (Lynch et al., 89 PROC. NATL. ACAD. SCI. USA 1138-42 (1992)); and epithelial cells (Nabel et al., 244 SCIENCE 1342-4 (1989); International PCT Application WO 90/06,997, the contents of which references and patent/patent applications are incorporated herein by reference).

The delivery of an effective dose of a prophylactic or therapeutic agent in situ depends on the efficiency of transfection (or transduction) as well as the number of target cells. Epithelial cell-based gene therapy, in particular, involves a relatively small area available in situ for receiving genetically modified epithelial cells. The delivery of an effective dose of prophylactic or therapeutic agent in situ thus depends upon the total number of implanted epithelial cells.

In one embodiment of the invention, exogenous genetic material (e.g., a cDNA encoding a polypeptide antagonist of the Pde2 polypepetide alone or with the Cap1 polypeptide, SEQ ID NO. 1, of the present invention, is introduced into a syngeneic host cell ex vivo or in vivo by genetic transfer methods, such as transfection or transduction, to provide a genetically modified host cell. Various expression vectors (i.e., vehicles for facilitating delivery of exogenous genetic material into a target cell) are known to one skilled in the art. In an alternate embodiment of the present invention, the exogenous genetic material encoding a polypeptide antagonist of the polypeptide of the PDE2 gene is introduced into a syngeneic host cell ex vivo or in vivo by genetic transfer methods, such as transfection or transduction, to provide a genetically modified host cell.

Transfection refers to the insertion of nucleic acid into a mammalian host cell using physical or chemical methods. Several transfection techniques are known to those of ordinary skill in the art including: calcium phosphate DNA co-precipitation (*Gene Transfer and Expression Protocols* in METHODS IN MOLECULAR BIOLOGY, Vol. 7 (E. J. Murray, ed., Humana Press) (1991)); DEAE-dextran; electroporation; cationic liposome-mediated transfection; and tungsten particle-facilitated microparticle bombardment (Johnston, 346 NATURE 776-7 (1990)). Strontium phosphate DNA co-precipitation (Brash et al., 7 MOL. CELL. BIOL. 2031-4 (1987)) is a preferred transfection method.

In contrast, transduction refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced host cell. A host cell that has been transduced with a chimeric DNA virus (e.g., an adenovirus carrying a cDNA encoding a therapeutic agent) will not have the exogenous genetic material incorporated into its genome, but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an enhancer is simply any non-translated DNA sequence, which works contiguous with the coding sequence to change the basal transcription level dictated by the promoter. Preferably, the exogenous genetic material is introduced into the host cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally occurring constitutive promoters control the expression of essential cell functions. As a result, a gene under the control of a constitutive promoter is expressed under all conditions of cell growth. Exemplary constitutive promoters include the promoters for the following genes which encode certain constitutive or housekeeping functions: hypoxanthine phosphoribosyl transferase (HPRT), dihydrofolate reductase (DHFR) (Scharfmann et al., 88 PROC. NATL. ACAD. SCI. USA 4626-30 (1991)), adenosine deaminase, phosphoglycerol kinase (PGK), pyruvate kinase, phosphoglycerol mutase, the beta-actin promoter (Lai et al., 86 PROC. NATL. ACAD. SCI. USA 10006-10 (1989)), and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and, the thymidine kinase promoter of Herpes Simplex Virus, among many others. Accordingly, any such constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs), which stimulate transcription when their inducing factors are bound. For example, there are REs for serum factors, steroid hormones, retinoic acid and cyclic AMP. Promoters containing a particular RE can be chosen in order to obtain an inducible response, and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified host cell. If the gene encoding the prophylactic or therapeutic agent is under the control of an inducible promoter, delivery of the agent in situ is triggered by exposing the genetically modified cell in situ to conditions for permitting transcription of the prophylactic or therapeutic agent, e.g., by intraperitoneal injection of specific inducers of the inducible promoters which control transcription of the agent. For example, in situ expression by genetically modified host cells of a therapeutic agent encoded by a gene under the control of the metallothionein promoter is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene (i.e., whether the promoter is constitutive or inducible, strong or weak); (2) the number of copies of the exogenous gene that are inserted into the host cell; (3) the number of transduced/transfected host cells that are administered (e.g., implanted) to the patient; (4) the size of the implant (e.g., graft or encapsulated expression system); (5)

the number of implants; (6) the length of time the transduced/transfected cells or implants are left in place; and (7) the production rate of the prophylactic or therapeutic agent by the genetically modified host cell. Selection and optimization of these factors for delivery of an effective dose of a particular prophylactic or therapeutic agent is deemed to be within the scope of one of skill in the art, taking into account the above-disclosed factors and the clinical profile of the patient.

In addition to at least one promoter and at least one heterologous nucleic acid encoding the prophylactic or therapeutic agent, the expression vector preferably includes a selection gene, for example, a neomycin resistance gene, for facilitating selection of host cells that have been transfected or transduced with the expression vector. Alternatively, the host cells are transfected with two or more expression vectors, at least one vector containing the gene(s) encoding the prophylactic or therapeutic agent(s), the other vector containing a selection gene. The selection of a suitable promoter, enhancer, and selection gene and/or signal sequence is deemed to be within the scope of one skilled in the art.

The prophylactic or therapeutic agent can be targeted for delivery to an extracellular, intracellular or membrane location. If it is desirable for the gene product to be secreted from the host cells, the expression vector is designed to include an appropriate secretion signal sequence for secreting the therapeutic gene product from the cell to the extracellular milieu. If it is desirable for the gene product to be retained within the host cell, this secretion signal sequence is omitted. In a similar manner, the expression vector can be constructed to include retention signal sequences for anchoring the prophylactic or therapeutic agent within the host cell plasma membrane. For example, membrane proteins have hydrophobic transmembrane regions that stop translocation of the protein in the membrane and do not allow the protein to be secreted. The construction of an expression vector including signal sequences for targeting a gene product to a particular location is deemed to be within the scope of one of skill in the art.

In an embodiment, vectors for mammalian host cell gene therapy are viruses, more preferably replication-deficient viruses (described in detail below). Exemplary viral vectors are derived from: Harvey Sarcoma virus; ROUS Sarcoma virus; MPSV; Moloney murine leukemia virus; and DNA viruses (e.g., adenovirus) (Temin, *Retrovirus vectors for gene transfer*, in GENE TRANSFER 149-87 (Kucherlapati, ed., Plenum) (1986)).

Replication-deficient retroviruses are capable of directing synthesis of virion proteins, but are incapable of making infectious particles. Accordingly, these genetically altered retroviral expression vectors have general utility for high-efficiency transduction of genes in cultured cells, and specific utility for use in the method of the present invention. Such retroviruses further have utility for the efficient transduction of genes into host cells in vivo. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in Kriegler, GENE TRANSFER AND EXPRESSION, A LABORATORY MANUAL (W.H. Freeman Co.) (1990) and Murray, E. J., ed., METHODS IN MOLECULAR BIOLOGY, Vol. 7 (Humana Press Inc.) (1991).

The major advantage of using retroviruses for gene therapy is that the viruses insert the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types (see e.g., Hilberg et al., 84 PROC. NATL. ACAD. SCI. USA 5232-6 (1987); Holland et al., 84 PROC. NATL. ACAD. SCI. USA 8662-6 (1987); Valerio et al., 84 GENE 419-27 (1989)). In vivo gene therapy using replication-deficient retroviral vectors to deliver a therapeutically effective amount of a therapeutic agent can be efficacious if the efficiency of transduction is high and/or the number of target cells available for transduction is high.

Yet another viral candidate useful as an expression vector for transformation of mammalian host cells is the adenovirus, a double-stranded DNA virus. The adenovirus is frequently responsible for respiratory tract infections in humans and thus appears to have an avidity for the epithelium of the respiratory tract (Straus, THE ADENOVIRUS 451-96 (H. S. Ginsberg, ed., Plenum Press) (1984)). Moreover, the adenovirus is infective in a wide range of cell types, including, for example, muscle and epithelial cells (Larrick et al., GENE THERAPY. APPLICATION OF MOLECULAR BIOLOGY 71-104 (Elsevier Science Publishing Co., Inc.) (1991)). The adenovirus also has been used as an expression vector in muscle cells in vivo (Quantin et al., 89 PROC. NATL. ACAD. SCI. USA 2581-4 (1992)).

Like the retrovirus, the adenovirus genome is adaptable for use as an expression vector for gene therapy, i.e., by removing the genetic information that controls production of the virus itself (Rosenfeld et al., 252 SCIENCE 4314 (1991)). Because the adenovirus functions in an extrachromosomal fashion, the recombinant adenovirus does not have the theoretical problem of insertional mutagenesis.

Thus, as will be apparent to one skilled in the art, a variety of suitable viral expression vectors are available for transferring exogenous genetic material into mammalian host cells. The selection of an appropriate expression vector to express an agent for the identification, prevention or treatment of microbial infection amenable to gene replacement therapy and the optimization of the conditions for insertion of the selected expression vector into the cell are within the scope of one of skill in the art without the need for undue experimentation.

In an alternative embodiment, the expression vector is in the form of a plasmid, which is transferred into the target host cells by one of a variety of methods: physical (e.g., microinjection (Capecchi; 22 CELL 479-88 (1980)); electroporation (Andreason et al., 6 BIOTECHNIQUES 650-60 (1988)); scrape loading, microparticle bombardment (Johnston, 346 NATURE 776-7 (1990)); and cellular uptake as a chemical complex (e.g., calcium or strontium co-precipitation, complexation with lipid, complexation with ligand) (*Gene Transfer and Expression Protocols* in METHODS IN MOLECULAR BIOLOGY, Vol. 7 (E. J. Murray, ed., Humana Press) (1991)). Several commercial products are available for cationic liposome complexation including Lipofectin (Invitrogen, Carlsbad, Calif.) (Feigner et al., 84 PROC. NATL. ACAD. SCI. USA 7413-7 (1987)) and Transfectam™ (ProMega, Madison, Wis.) (Behr et al., 86 PROC. NATL. ACAD. SCI. USA 6982-6 (1989); Loeffler et al., 54 J. NEUROCHEM. 1812-5 (1990)). However, the efficiency of transfection by these methods is highly dependent on the nature of the target cell and accordingly, the conditions for optimal transfection of nucleic acids into host cells using the above-mentioned procedures must be optimized. Such optimization is within the scope of one of skill in the art.

In an embodiment, the preparation of genetically modified host cells contains an amount of cells sufficient to deliver a prophylactically or therapeutically effective dose of a disrupted gene of the present invention to the recipient in situ. The determination of an effective dose of the prophylactic or therapeutic agent for a known microbial infection is within the scope of one of skill in the art. Thus, in determining the effective dose, the skilled artisan would consider the condition of the patient, the severity of the condition, as well as the results of clinical studies of the prophylactic or therapeutic agent being administered.

If the genetically modified host cells are not already present in a pharmaceutically acceptable carrier, they are placed in such a carrier prior to administration to the recipient. Such pharmaceutically acceptable carriers include, for example, isotonic saline and other buffers as appropriate to the patient and therapy. The genetically modified cells are administered by, for example, intraperitoneal injecting or implanting the cells or a graft or capsule containing the cells in a host cell-compatible site of the recipient. As used herein, host cell-compatible site refers to a structure, cavity or fluid of the recipient into which the genetically modified cell(s), host cell graft, or encapsulated host cell expression system can be implanted, without triggering adverse physiological consequences. Representative host cell-compatible sites include, for example, the peritoneal, pleural and pericardial cavities. Preferably, the host cell-compatible site communicates with the lymphatic system, thereby enabling delivery of the therapeutic agent to the vascular system.

In one embodiment, the host cell-compatible site may be denuded prior to implanting the cells. Exemplary denuding methods include but are not limited to: (1) injection of distilled water into the site (e.g., the peritoneal cavity) for 20 minutes, followed by scraping off a portion of the epithelial layer; (2) injection of 0.1% buffered trypsin for 20 minutes followed by scraping; (3) removal of epithelial cells by gentle scraping with a cell scraper and (4) touching a piece of Gelfilm (Upjohn, Kalamazoo, Mich.) to the endothelium.

The genetically modified host cells are implanted in a host cell-compatible site, alone or in combination with other genetically modified host cells. Thus, the instant invention embraces a method for modifying the epithelial system of a recipient by using a mixture of genetically modified host cells, such that a first modified cell expresses a first prophylactic or therapeutic agent of the present invention and a second modified cell expresses a second prophylactic or therapeutic agent. Other genetically modified cell types (e.g., hepatocytes, smooth muscle cells, fibroblasts, glial cells, mesothelial cells or keratinocytes) can be added, together with the genetically altered epithelial cells, to produce expression of a complex set of introduced genes. Moreover, more than one recombinant gene can be introduced into each genetically modified cell on the same or different vectors, thereby allowing the expression of multiple prophylactic or therapeutic agents of the present invention by a single cell.

The instant invention further embraces an epithelial cell graft. The graft may comprise a plurality of the above-described genetically modified cells attached to a support that is suitable for implantation into a mammalian recipient, preferably into the oral cavity. The support can be formed of a natural or synthetic material. According to another aspect of the invention, an encapsulated host cell expression system is provided. The encapsulated system includes a capsule suitable for implantation into a mammalian recipient and a plurality of the above described genetically modified host cells contained therein. The capsule can be formed of a synthetic or naturally occurring material. The formulation of such capsules is known to one of ordinary skill in the art. In contrast to the host cells that are directly implanted into the mammalian recipient (i.e., implanted in a manner such that the genetically modified cells are in direct physical contact with the host cell-compatible site), the encapsulated cells may remain isolated (i.e., not in direct physical contact with the site) following implantation. Thus, the encapsulated host cell system is not limited to a capsule including genetically modified non-immortalized host cells, but may contain genetically modified immortalized host cells.

Polypeptides

As used herein, polypeptide refers to a linear series of amino acid residues connected to one another by peptide bonds between the alpha-amino groups and carboxy groups of adjacent amino acid residues. Additional covalent bonds between portions of the peptide are also present to restrain the conformation of the molecule, such as amide and disulfide bonds. When used herein, protein also refers to a linear series of amino acid residues connected one to the other as in a peptide. The term synthetic peptide means a chemically derived chain of amino acid residues linked together by peptide bonds that is free of naturally occurring proteins and fragments thereof.

Polypeptides of the present invention may include any analog, fragment or chemical derivative of the polypeptide capable of stimulating increases in cAMP levels which in turn promotes bud-hypha transitions or any analog, fragment or chemical derivation of an inhibitor of the polypeptide capable of stimulating increases in cAMP levels which in turn promotes bud-hypha transitions. Polypeptides thus may include soluble peptides, Ig-tailed fusion peptides, members of random peptide libraries (see, e.g., Lam et al., 354 NATURE 824 (1991); Houghten et al., 354 NATURE 84-6 (1991)), combinatorial chemistry-derived molecular library made of D- and/or L-configuration amino acids, and phosphopeptides (including members of random or partially degenerate, directed phosphopeptide libraries, see, e.g., Songyang et al., 72 CELL 767-78(1993)).

Such polypeptides may include those derived from the transcription and translation of the CAP1 gene (SEQ ID NO. 2), those derived from the C. albicans Cap1 (SEQ ID NO. 1), and those derived from the PDE2 gene sequence. The term analog refers to any polypeptide having an amino acid sequence, in comparison to the amino acid sequences of the polypeptides of the present invention, in which one or more amino acids have been substituted with other amino acids; where the substituted amino acids allow or require the polypeptide to assume the equilibrium conformation of the domain of the parent protein. Often, cysteine, lysine and glutamic acid will be used for their side chains, which can form covalent linkages to restrict the conformation of a peptide.

The term analog shall also include any polypeptide, which has one or more amino acids deleted from or added to an amino acid sequence of the C. albicans pde2 or Cap1, but which still retains stimulatory activity in increasing cAMP levels in the cAMP-PKA signaling pathway. The term fragment includes any portion of an amino acid sequence, which retains at least one structural or functional characteristic of the subject C. albicans Pde2 or Cap1, wherein the fragment is capable of stimulating increases in cAMP levels, which in turn promote bud hypha transitions. Any polypeptide or fragment which has one or more amino acids deleted from or added to an amino acid sequence of a *C. albicans* Cap1 antagonist and/or pde2 antagonist which inhibits stimulatory activity in increasing cAMP levels in the cAMP-PKA signaling pathway is also included.

The polypeptides of the present invention may be prepared by any known techniques. Conveniently, the polypeptides may be prepared using the solid-phase synthetic technique initially described by Merrifield (15 J. AM. CHEM. SOC. 2149-54 (1963)). Other peptide synthesis techniques may be found, for example, in Bodanszky et al., PEPTIDE SYNTHESIS ($2^{nd}$ ed. John Wiley & Sons) (1976) as well as in other reference works known to those skilled in the art. A summary of peptide synthesis techniques may be found in Stuart and Young, SOLID PHASE PEPTIDE SYNTHELIA (Pierce Chemical Co.) (1984). The synthesis of peptides by solution methods may also be used, as described in THE PROTEINS 105-237 (H. Heurath et al., eds., $3^{rd}$ ed., Vol. 11, Academic Press) (1976). Appropriate protective groups for use in such syntheses will be found in the above referenced texts as well as in McOmie, PROTECTIVE GROUPS IN ORGANIC CHEMISTRY (Plenum Press) (1973). In general, these synthetic methods involve the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side functional group, such as lysine.

Using solid phase peptide synthesis as an example, the protected or derivatized amino acid is attached to an inert solid support, known as the 'resin,' through its unprotected carboxyl or amino terminus. The majority of known solid phase peptide syntheses are performed with the amino acid carboxyl terminus linked to solid support due to the preponderance of side reactions found with peptide chain extension using amino acids that are N-linked to solid support. In such cases, synthesis would continue with the removal of the N-terminus protecting group of the resin bound amino acid followed by introduction of a suitably protected amino acid under conditions required for amide bond formation. The N-terminus protecting group of the newly formed dipeptide is then removed and the next amino acid (suitably protected) in the sequence added, and so forth. After all the desired amino acids have been linked in the proper sequence, any remaining terminal and side chain protecting group(s) (and solid support) are removed sequentially or concurrently, to provide the final peptide. The polypeptides of the invention preferably are devoid of benzylated or methylbenzylated amino acids. Such protecting group moieties may be used in the course of synthesis, but they are removed before the polypeptides are used. Additional reactions may be necessary, as described elsewhere to form intramolecular linkages to restrain conformation if desired. The polypeptides of the present invention may also be linked to an additional sequence of amino acids either or both at the N-terminus and at the C-terminus. Such additional amino acid sequences, or linker sequences, can be conveniently affixed to a detectable label, solid matrix, or carrier. Typical amino acid residues used for linking are tyrosine, cysteine, lysine, glutamic acid and aspartic acid, or the like.

Of course, the present polypeptides may also be prepared by recombinant DNA techniques. The present invention also relates to vectors comprising DNA molecules of the present invention, host cells which are genetically engineered with vectors of the invention and the production of polypeptides of the invention by recombinant techniques. Host cells may be genetically engineered (transduced or transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying genes. The culture conditions, such as temperature, pH and the like, are preferably those previously used with the host cell selected for expression, and will be apparent to the skilled artisan. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by SAMBROOK ET AL., supra.

The polypeptides of the present invention may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic-procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

Another embodiment of the present invention is the identification and production of a polypeptide antagonist of a polypeptide comprising the amino acid sequence of PDE2 alone or with the polypeptide comprising the amino acid sequence of SEQ. ID No. 1. In this embodiment (1) molecular modeling of the *C. albicans* Pde2 alone or with Cap1 is performed to determine secondary structure and important protein/receptor interactions, (2) a library of polypeptide substrates are designed to mimic the interaction of *C. albicans* Pde2 alone or with Cap1 with its receptor, (3) the substrates are subject to functional assays to determine antagonistic activity, and (4) the most potent antagonist is produced through molecular biology and synthetic methods described in the present invention.

An additional embodiment is the use of plant cell cultures to produce the polypeptide and polypeptide antagonists of the present invention. The employment of plant host systems to produce proteins has been described by Zenk, 30 PHYTOCHEM. 3861-63 (1991) and by Goodman, see U.S. Pat. No. 5,550,038. A basic plant vector construct can be employed where the heterologous gene is not readily amenable to detection. Such construct would have a prokaryote selectable marker, preferably suitable for determining if a plant cell has been transformed. A suitable sequence to permit integration of the heterologous sequence into the plant genome is also preferred.

For use in a method of prevention or treatment, such as the prevention or treatment of infection of a mammalian host by a microorganism, the polypeptides of the present invention may be present in a pharmaceutical composition in admixture with a pharmaceutically acceptable sterile vehicle. The pharmaceutical composition may be compounded according to conventional pharmaceutical formulation techniques. In one embodiment, the polypeptide antagonists of the present invention may be used as a vaccine for preventing infection by a microorganism of a mammalian host comprising an effective amount of antagonist against Pde2 and/or Cap1 in a pharmaceutically acceptable sterile vehicle. In a preferred embodiment, the vaccine is capable of interfering with biochemical signaling pathways of the microorganism with the cells of the host. In another preferred embodiment, the vaccine is capable of interfering with the cAMP-PKA signaling pathways of the microorganism, where the cAMP-PKA signaling pathway operates to increase levels of cAMP in the microorganism. In an alternate embodiment of the present invention, the vaccine is capable of interfering with the cAMP-PKA signaling pathway of the microorganism, where the cAMP-PKA signaling pathway operates to decrease levels of cAMP in the microorganism.

The vehicle may take a wide variety of forms depending on the form of preparation desired for administration, e.g., sublingual, rectal, nasal, oral or parenteral. Compositions for oral dosage form may include any of the usual pharmaceutical media, such as, for example, water, oils, alcohols, flavoring agents, preservatives, coloring agents and the like in the case of oral liquid preparations (e.g., suspensions, elixirs and solutions) or carriers such as starches, sugars, diluents, granulating agents, lubricants, binders, disintegrating agents and the like in the case of oral solid preparations (e.g., powders, capsules and tablets). Controlled release forms may also be used. Because of their ease in administration, tablets and capsules represent an advantageous oral dosage unit form, in which case solid pharmaceutical carriers may be employed. If desired, tablets may be sugar coated or enteric coated by standard techniques.

For compositions to be administered parenterally, the carrier will usually comprise sterile water, although other ingredients to aid solubility or for preservation purposes may be included. Injectable suspensions may also be prepared, in which case appropriate liquid carriers, suspending agents and the like may be employed. The parenteral routes of administration may be intravenous injection, intramuscular injection or subcutaneous injection.

For intravenous administration, the polypeptides may be dissolved in an appropriate intravenous delivery vehicle containing physiologically compatible substances such as sodium chloride, glycine and the like, having a buffered pH compatible with physiologic conditions. Such intravenous delivery vehicles are known to those skilled in the art.

The polypeptides of the invention may be administered to subjects where alteration of PDE2 gene alone or with CAP1 gene expression is desired. The peptides may be administered by any convenient means. Oral administration is presently contemplated as a preferred administration route. The amount administered will depend on the activity of the particular compound administered, which may readily be determined by those of ordinary skill in the art.

Antibodies

Antibodies of the present invention may include any polyclonal, monoclonal, humanized, anti-idiotypic, chimeric or single chain antibodies, and FAb, F(ab')$_2$ and FAb expression library fragments, and epitope-binding fragments thereof.

Another embodiment of the present invention relates to a monoclonal antibody to the polypeptide of the PDE2 nucleic acid sequence alone or with the polypeptide of SEQ ID NO. 1 of the present invention (or an antigenic portion thereof), which may be produced by methods recognized in the art, including the formation of monoclonal antibody-producing hybridomas (Kohler et al., 256 NATURE 495-97 (1975); Kohler et al. 6 EUR. J. IMMUNOL. 511-19 (1976)).

The monoclonal antibodies of the present invention can be used as probes in detecting discrete antigens expressed by microorganisms. The expression or lack of expression of these antigens can provide clinically exploitable information that is not apparent after standard histopathological evaluations. It may thus be possible to correlate the immunophenotypes of individual microorganisms with various aspects of microbial-mammalian host interaction and responsiveness to certain types of therapies, thereby establishing important classifications of prognosis.

The antibodies may also be used to detect drug resistance in microorganisms. For example, drug resistant *C. albicans* can make hyphae (germ tubes) in the presence of drug, but susceptible strains cannot (see 138 J. GEN. MICROBIOL. 1901-11 (1992)). Because CAP1 is a marker of bud/hypha transition, the detection of the presence or absence of CAP1 may be useful in the monitoring of drug resistance in *C. albicans*. In an alternate embodiment of the present invention, the detection of the presence of absence of PDE2 may be useful in monitoring the drug resistance in *C. albicans*.

The use of the monoclonal antibodies described herein can be extended to the screening of human biological fluids for the presence of the specific antigenic determinant recognized. In vitro immunoserological evaluation of sera withdrawn from patients thereby permits non-invasive diagnosis of microbial infection. By way of illustration, human fluids, such as pleural fluids or lymph, can be taken from a patient and assayed for the specific epitope, either as released antigen or membrane-bound on cells in the sample fluid, using monoclonal antibodies against the polypeptides of the present invention in standard radioimmunoassays or enzyme-linked immunoassays known in the art or competitive binding enzyme-linked immunoassays.

The monoclonal antibodies of this invention are potentially useful for targeting microbial infection in vivo. They can therefore be used in humans for localization and monitoring of the microbial infection. For this application, it is preferable to use purified monoclonal antibodies. Purification of monoclonal antibodies for human administration by ammonium sulfate or sodium sulfate precipitation followed by dialysis against saline and filtration sterilization has been described by Miller et al. in HYBRIDOMAS IN CANCER DIAGNOSIS AND THERAPY 134 (1982).

In an alternate embodiment, the antibodies described herein are used to stimulate the production of corresponding anti-idiotypic antibodies. In brief, anti-idiotypic antibodies, or antiidiotypes are antibodies directed against the antigen-combining region or variable region (idiotype) of another antibody. Based on Jerne's network model of idiotypic relationships (Jerne, 125 ANN. IMMUNOL. 373 (1974); Jerne et al., 1 EMBO 234 (1982)), immunization with an antibody molecule expressing a paratope (antigen-combining site) for a given antigen should produce a group of anti-antibodies, some of which share with the antigen a complementary structure to the paratope. Immunization with a subpopulation of antiidiotypic antibodies should in turn produce a subpopulation of antiidiotypic antibodies, which bind the initial antigen. Thus, the administration of the monoclonal antibodies of the present invention may result in a modification of the host's anti-microbial immune response, as the consequence of the formation of anti-idiotypic antibodies, which may develop during therapy with the monoclonals.

The monoclonal antibodies of this invention can be used in conjunction with a broad spectrum of pharmaceutical or cytotoxic agents that selectively affect a microorganism over the mammalian host. The methods used for binding the cytotoxic agents to the monoclonal antibody molecule can involve either non-covalent or covalent linkages. Since non-covalent bonds are more likely to be broken before the antibody complex reaches the target site, covalent linkages are preferred. For instance, carbodiimide can be used to link carboxy groups of the pharmaceutical agent to amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde that is then reacted with the antibody molecule. Attachment occurs via formation of a Schiff base with amino groups of the antibody molecule. Additionally, drugs with reactive sulfhydryl groups have been coupled to antibody molecules.

Another embodiment of the invention relates to a diagnostic kit for detecting a microorganism expressing a protein. The diagnostic kit may further comprise, where necessary, other components of the signal producing system, including agents for reducing background interference, control reagents, or an apparatus, container or other solid support for conducting the test. The binding of antibody to the target can be detected by well known methods, including radiation (e.g., use of a radioactive nucleotide), colorimetry (e.g., use of an enzyme that can cause a color change in a substrate), fluorescence (e.g., use of a dye such as propidium iodide, fluorescein, or rhodamine), and luminescence (e.g., use of an alkaline phosphatase substrate that releases photons upon cleavage or luciferin). Detection can be qualitative or quantitative.

Antisense Compounds

A further embodiment of the present invention involves the use of oligomeric antisense compounds, particularly oligonucleotides, for inhibiting the function of nucleic acid molecules encoding *C. albicans* PDE2 alone or with the CAP1 (SEQ ID NO. 1). Antisense technology has successfully inhibited expression of a variety of genes (Agrawal, 10 TRENDS BIOTECH. 152 (1992)). These include inhibition of murine and human IL-1-stimulated PGE2 synthesis (Burch and Mahan, 88 J. CLIN. INVEST. 1190 (1991)), inhibited expression of a mutated human procollagen gene (Colige et al., 32 BIOCHEM. 7 (1993)), and inhibition of mutant Ha-ras mRNA expression (Monia et al., 267 J. BIOL. CHEM. 19954 (1992)). Hybridization of the antisense compound to one or more of the nucleic acids encoding Pde2 and/or Cap1 interferes with normal function of the nucleic acid(s). In this case, the mRNA transcribed from the PDE2 and/or CAP1 gene is targeted. The preferred sites for interference are the regions encompassing the translation initiation or termination codon of the open reading frame for the gene.

Antisense oligonucleotides are the preferred form of antisense compounds but oligonucleotide mimetics may also be used. Oligonucleotides are composed of heterocyclic bases and sugars linked by a phosphodiester group. Oligonucleotide mimetics are therefore compounds that retain the basic structure and function of an oligonucleotide but contain modified or novel groups replacing one or more heterocyclic base, sugar or phosphodiester linkage or any combination thereof. Examples of modified nucleobases include synthetic and natural nucleobases such as those described in U.S. Pat. No. 3,687,808, described in THE CONCISE ENCYCLOPEDIA OF POLYMER SCIENCE AND ENGINEERING 858-859 (Kroschwitz ed., John Wiley & Sons) (1990), disclosed by Englisch et al., 30 ANGEW CHEM., INT. ED., 613 (1991), and disclosed by Sanghvi, ANTISENSE RESEARCH AND APPLICATIONS 289-302 (Crooke and Lebleu, eds., CRC Press) (1993). Substituted sugar moieties include 2' substituted OH; F; O—, S—, or N-alkyl; O—, S—, or N-alkenyl; O—, S—, or N-alkynyl; or O-alkyl-O-alkyl among others, as well as 3' substituted sugars of the 3' terminal nucleotide and the 5' substituted sugars of 5' terminal nucleotide. Examples of modified backbones or non-natural internucleoside linkages include phosphorothioates, chiral phosphorothioates, phosphorodithioates, phosphotriesters, aminoalkylphosphotriesters, methyl and other alkyl phosphonates, chiral phosphonates, phosphinates, phosphoramidates, aminoalkylphosphoramidates, thionophosphoramidates, thiono-alkylphosphonates, thionoalkylphosphotriesters, and boranophosphates. Peptide nucleic acids (PNA), which replace both the sugar and the internucleoside linkage, may also be used as oligonucleotide mimetics (Nielsen et al., 254 SCIENCE, 1497-1500 (1991)).

Ribozymes

The invention further embraces the synthesis of ribozymes, which may inhibit Pde2 and/or Cap1 expression. Ribozymes are RNA molecules having an enzymatic activity, which is able to repeatedly cleave other separate RNA molecules in a nucleotide base sequence specific manner. Such enzymatic RNA molecules may be targeted to virtually any RNA transcript, and efficient cleavage achieved in vitro. See generally Kim et al., 84 PROC. NATL. ACAD. SCI. USA 8788 (1987); Haseloff & Gerlach, 334 NATURE 585 (1988); Cech, 260 JAMA 3030 (1988); Jefferies et al., 17 NUCL. ACIDS RES. 1371 (1989).

Six basic varieties of naturally occurring enzymatic RNAs are known presently. Each can catalyze the hydrolysis of RNA phosphodiester bonds in trans (and thus can cleave other RNA molecules) under physiological conditions. In general, enzymatic polynucleotides act by first binding to a target RNA. Such binding occurs through the target binding portion of a enzymatic polynucleotide which is held in close proximity to an enzymatic portion of the molecule that acts to cleave the target RNA. Thus, the enzymatic polynucleotide first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic polynucleotide has bound and cleaved its RNA target, it is released from that RNA to search for another target and can repeatedly bind and cleave new targets.

The enzymatic nature of a ribozyme may be advantageous over other technologies, such as antisense technology (where a polynucleotide molecule simply binds to a polynucleotide target to block its translation) because the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA.

In addition, the ribozyme is a highly specific inhibitor, with the specificity of inhibition depending not only on the base pairing mechanism of binding, but also on the mechanism by which the molecule inhibits the expression of the RNA to which it binds. In other words, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is likely that the specificity of action of a ribozyme is greater than that of antisense oligonucleotide binding the same RNA site.

The ribozyme of the present invention may comprise one of several motifs including hammerhead (Rossi et al., 8 AIDS RESEARCH AND HUMAN RETROVIRUSES 183 (1992)), hairpin (Hampel and Tritz, 28 BIOCHEM. 4929 (1989); Hampel et al., NUCL. ACIDS RES. 299 (1990)), hepatitis delta virus motif (Perrotta and Been, 31 BIOCHEM. 16 (1992), group I intron (U.S. Pat. No. 4,987,071), RNaseP RNA in association with an RNA guide sequence (Guerrier-Takada et al., 35 CELL 849 (1983)), and Neurospora VS RNA (Saville & Collins, 61 CELL 685-96 (1990); Saville & Collins, 88 PROC. NATL. ACAD. SCI. USA 8826-30 (1991); Collins & Olive, 32 BIOCHEM. 2795-99 (1993)). These specific motifs are not limiting in the invention and those skilled in the art will recognize that all that is important in an enzymatic polynucleotide molecule of this invention is that it has a specific substrate binding site which is complementary to one or more of the target gene RNA regions, and that it have nucleotide sequences within or surrounding that substrate binding site which impart an RNA cleaving activity to the molecule.

As in the antisense approach, the ribozymes of the present invention may be composed of modified oligonucleotides (e.g., for improved stability, targeting, etc.) and may be delivered to cells that express Pde2 and/or Cap1 polypeptides in vivo. Polynucleotide constructs encoding the ribozymes may be introduced into the cell in the same manner as described above for the introduction of antisense encoding DNA. In one embodiment, delivery involves using a DNA construct "encoding" the ribozyme under the control of a strong constitutive promoter, such as, for example, RNA Polymerase II or RNA Polymerase III promoter, so that transfected cells will produce sufficient quantities of the ribozyme to destroy endogenous Pde2 and/or Cap1 messages and inhibit their translation. Because ribozymes, unlike antisense molecules, are catalytic, a lower intracellular concentration may be required for efficiency.

Ribozymes may be administered to cells by a variety of methods known to those familiar to the art, including, but not restricted to, encapsulation in liposomes, by ionophoresis, or by incorporation into other vehicles, such as hydrogels, cyclodextrins, biodegradable nanocapsules, and bioadhesive microspheres. Furthermore, ribozymes may be directly delivered ex vivo to cells or tissues with or without the aforementioned vehicles. Alternatively, the RNA/vehicle combination may be locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. See generally WO 94/02595; WO 93/23569.

The invention has been disclosed broadly and illustrated in reference to representative embodiments described above. Those skilled in the art will recognize that various modifications can be made to the present invention without departing from the spirit and scope thereof. Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Example 1

C. albicans Strains and Growth Conditions

The E. coli strain HB101 was used to propagate plasmids (Boyer et al., 41 J. MOL. BIOL. 459-72 (1969)). C. albicans strains are listed in FIG. 1. Yeast forms were grown in yeast extract peptone dextrose (YPD) or yeast nitrogen base containing 50 mM glucose (YNB) (ROSE ET AL., METHODS IN YEAST GENETICS (Cold Spring Harbor Laboratory Press) (1990)). Mass conversion of stationary phase yeasts (grown at 30° C. for 48 h) to germ tubes was induced at 37° C. in the following pre-warmed media, Lee's media (pH 6.8) (Lee et al., 13 SABOURAUDIA 148-53 (1975)), Medium 199 (Gibco-BRL, Carlsbad, Calif.) with 150 mM HEPES (pH 7.0) (M199), M199 containing 5% bovine calf serum (Sigma, St. Louis, Mo.) (M199+serum), 50 mM potassium phosphate (pH 6.0) plus 10% bovine calf serum (Feng et al., supra), 10 mM imidazole-HCl buffer media (pH 7.0) containing 0.2 mM $MnC_2$ with the following inducing agents: 1) 4 mM N-acetylglucosamine, 2) 10 mM L-proline plus 10 mM glucose, and 3) 2.5 mM glutamine plus 2.5 mM glucose. Shepard et al., 26 CAN. J. MICROBIOL. 21-6 (1980), Dabrowa, et al., 127 J. GEN. MICROBIOL. 391-7 (1981). Whole human saliva was collected on ice and clarified by centrifugation at 10,000×g for 15 min at 4° C. (Kimura et al., 21 INFECT. IMMUN. 64-8 (1978)). Tetracycline was added to clarified saliva at a concentration of 50 μg/ml to inhibit bacterial growth.

For growth analysis in agar-containing media, stationary phase yeasts were mixed (100 cells/20 ml media) with liquified agar containing, M199 adjusted to neutral pH with 7.5% sodium bicarbonate, Spider medium (Liu et al., 266 SCIENCE 1723-6 (1994)), 2% agar containing 4% bovine calf serum (Lo et al., 90 CELL 939-49 (1997)), and synthetic low ammonium dextrose (SLAD) containing 50 μM ammonium sulfate (Csank et al., 66 INFECT. IMMUN. 2713-21 (1998)). Filamentous growth on YPD agar was assessed by streaking strains on YPD plates followed by incubation at room temperature for two weeks. Each plate was examined daily for the presence of filamentous growth.

To determine the effect of exogenous cAMP on bud-hypha transitions and filamenious growth of cap1/cap1 mutants, stationary phase yeasts were induced to form germ tubes and hyphae in liquid M199+serum ($10^6$ cells/ml) or in SLAD agar plates containing 10 mM cAMP or dbcAMP (Sigma). M199+serum containing cAMP or dbcAMP were incubated at 37° C. for 20 h and the frequency of germ tube formation was measured at various time points. SLAD plates containing cAMP or dbcAMP were incubated at 37° C. for 5 days, and filamentous growth was monitored daily.

Example 2

Isolation and DNA Sequencing of cDNA and Genomic Clones for CAP1

CAP1 cDNA clones were found while attempting to identify germ tube-specific surface antigens by screening a *C. albicans* germ tube cDNA library (Sundstrom et al., 174 J. BACTERIOL. 6789-99 (1992)) but cDNAs encoding cell wall surface proteins were not found. Five of the thirteen cDNA clones isolated encoded proteins with homology to adenylate cyclase associated proteins. pBluescript SK-phagemids of the five clones were rescued by in vivo excision (Strategene) according the manufacturer's directions. pCAP1, with a 1655 bp CAP1 cDNA insert was analyzed further.

Three λ genomic CAP1 clones (CAP2, CAP3, and CAP5) were isolated by screening a λ GEM12 genomic library of *C. albicans* SC5314 (Birse et al., 61 INFECT. IMMUN. 3648-55 (1993)) with CAP1 cDNA excised from pCAP1 with XbaI and XhoI. pGHCP17 was constructed by subcloning the 3.7 kbp CAP1 genomic HindIII fragment of CAP5 into pBluescript SK- and transforming *E. coli* HB101 (Boyer et al., 41 J. MOL. BIOL. 459-72 (1969)). DNA sequences of cDNA and genomic clones were determined by automated cycle sequencing using an automated DNA sequencer (ABI Prism, model 377 and 373, Perkin-Elmer Co.).

Complete genomic DNA sequence of CAP1 was compared with the sequence of SRV2 in the current assembly 6 of the *C. albicans* genomic sequences from the Stanford DNA Sequencing and Technology Center website at http://www.sequence.stanford.edu/group/*candida*.

Example 3

Disruption of CAP1

To disrupt CAP1 in *C. albicans*, plasmid pCAPURA3 was constructed by replacing 132 bp StyI-BsmI fragment of CAP1 cDNA in pCAP1 with the 4.0 kbp BamHI-BglII hisG-URA3-hisG cassette from p5921 (Fonzi et al., 134 GENETICS 717-28 (1993)) after generating blunt ends using T4 DNA polymerase (Gibco-BRL) and the Klenow fragment of *E. coli* DNA polymerase I. *E. coli* HB101 served as the host strain for transformation and propagation of pCAPURA3.

CAI4 (CAP1/CAP1, ura3/ura3) was transformed using spheroplast transformation (Kurtz et al., 6 MOL. CELL. BIOL. 142-9 (1986)) with 10 µg of pCAPURA3 digested with PstI to release the CAP1 disruption cassette. Ura$^+$ transformants with an CAP1/cap1::hisG-URA3-hisG genotype were identified by Southern blotting using HindIII-digested genomic DNA (Scherer et al., 25 J. CLIN. MICROBIOL. 675-9 (1987)). Southern blots were probed with hisG-URA3hisG from p5921 and PCR-1.2 (FIG. 2A). PCR-1.2 (nucleotides 98 to 1318) was generated by PCR using pGHCP17 as template and oligonucleotides CAP-R4 (5'CCATTTTCCAAGAGGAAGCA3'; SEQ ID NO:20) and CAP-F4 (5'CCGACACTGCATTTGCTTTA3'; SEQ ID NO:21). Probes were labeled using the enhanced chemiluminescence (ECL) Direct Nucleic Acid Labeling and Detection System (Amersham). CAC1-1 (ura3/ura3 CAP1/cap1::hisG) was selected on YNB media (0.002% uridine) containing 0.05% 5-fluoroorotic acid (5-FOA) (Boeke et al., 197 MOL. GEN. GENET. 345-6 (1984)) and used in a second round of transformation to disrupt the remaining copy of CAP1. Colony PCR (van Zeijl et al., 59 J. BIOTECH. 221-4 (1997)), using the TaqPlus® Long PCR system (Stratagene) with primers CAP-R4 and CAP-F4, and Southern blotting were used to determine genotypes. Gene inactivation was confirmed by Northern blot analysis and RT-PCR.

Complementation of cap1/cap1 mutants at the CAP1 genomic locus was accomplished by co-transformation of a ura3 homozygous cap1/cap1 mutant strain, CAC1-1A1 with eno::URA3 (Staab et al., 283 SCIENCE 1535-8 (1999)) and PCR-1.2 creating CACRE1. DNA sequencing of genomic DNA clones from CACRE1 confirmed that mutations were not inadvertently introduced from PCR-1.2 into the CAP1 locus in the revertant.

Cell morphologies were examined using a 40× or 20× objective and differential interference contrast microscopy (OLYMPUS BX60) and photographed (OLYMPUS Magnafire, Model S99806). Colonial morphologies were examined using a stereomicroscope (OLYMPUS SZX12) (1.6× objective) with a transmitted light console base or OLYMPUS BX60 microscope (4× objective), and cellular morphologies at colony rims were examined with brightfield illumination using a light microscope (Nikon, LABOPHOT-2)(10× objective) equipped with a CCD video camera system (OPTRONICS). Photographed images were processed using Adobe PhotoShop 2.5.

Example 4

Northern Blot Analysis

Total RNA was isolated (Staab et al., 271 J. BIOL. CHEM. 6298-305 (1996)) from middle logarithmic phase yeast cultured in 250 ml YNB at 27° or germ tubes (yeasts for the cap1/cap1 mutant) cultured for three hours in M199 at 37° C. and treated with RNase-free DNase I (GIBCO-BRL) . Probes were PCR-1.2 (FIG. 2A) and a 687 bp PCR product amplified from the 18S rRNA gene of *C. albicans* SC5314 (Makimura et al., 40 J. MED. MICROBIOL. 358-64 (1994)) using primers (5'-ACTTTCGATGGTAG-GATAG-3', SEQ ID NO:22; and 5'-TGATCATCTTCGATC-CCCTA-3', SEQ ID NO:23). Electrophoresis, radiolabeling of probes using the random primer method (Feinberg and Vogelstein, 132 ANAL. BIOCHEM. 6-13 (1983); Feinberg and Vogelstein 137 (Addendum) ANAL. BIOCHEM. 266-7 (1984)), hybridization and molecular size determination were performed as described by Staab et al. (J. BIOL. CHEM., supra), except that blots were hybridized first with the CAP1 probe ($10^7$ cpm), autoradiographed and then used with the 18S rRNA probe ($10^6$ cpm).

Example 5

RT-PCR

The first-strand cDNA was synthesized using 1 µg of total RNA according to the manufacturer's directions (Promega; Reverse Transcription System) and was diluted in a final 100

μl volume of nuclease-free water. Two PCR products representing the 5'-(1 to 605) and 3'-(922 to 1634) portions of CAP1 message (FIG. 2A) were amplified from the first-strand cDNA (10 μl) using oligonucleotides CAP-NRT1 (5'-ATGTCAACCGAGGAGAGTCA-3'; SEQ ID NO:24) and CAP-F1 (5'-ATGTACGAGATTGGTGTAGG-3'; SEQ ID NO:25) and CAP-R3 (5'-AGTGAAAATCCATCTC-CAGC-3'; SEQ ID NO:26) and CAP-3F1 (5'-CCAGCAT-GTTCAACAATTTGAG-3'; SEQ ID NO:27) respectively. ACT1 cDNA (304 bp), amplified using two ACT1-specific primers, ACT-3R (5'-GGAGTTGAAAGTGGTTTGGT-CAATAC-3'; SEQ ID NO:28) and ACT-5L (5'-GGCTGG-TAGAGACTTGACCAACCATTTG-3'; SEQ ID NO:29) (Naglik et al., 67 INFECT. IMMUN. 2482-90 (1999)) served as a control. PCR products were detected by Southern blotting using PCR-1.6, which spanned the entire CAP1 coding region, as a probe (FIG. 2A) PCR-1.6 (nucleotides 1 to 1634) was generated by PCR using pGHCP17 and oligonucleotides CAP-NRT1 and CAP-3F1. Probe PCR-1.6 was labeled with [$\alpha$-$^{32}$P]-dCTP (Amersham) as for Northern blot except that $2\times10^6$ cpm was added to the membrane.

Example 6

Cyclic AMP Assay

Intracellular cAMP levels in M199 was extracted as previously described by Fedor-Chaiken et al., (supra) and measured using the cAMP enzyme immunoassay (Amersham). Strains (UnoPP-1, CAC1, CAC1-1A, and CACRE1) were grown to middle logarithmic phase ($OD_{600nm}$=0.6-0.7) in M199 at 27° C. and then inoculated ($4\times10^6$ cells/ml) into M199 prewarmed to 37° C. to induce germ tubes or fresh M199 at 27° C. for budding growth. At each time point during germ tube formation (or budding in the case of the cap1/cap1 mutant), 27 and 1.5 ml portions were withdrawn for measurement of cAMP levels and protein concentration, respectively.

Protein concentrations (Coomassie protein assay, Pierce) were determined on cell extracts from 1.5 ml of culture lysed by boiling of 5 min in 50 μl of 2N NaOH. Bovine serum albumin (5-25 μg/ml) was used to generate a standard curve.

Example 7

Screening and DNA Sequence Analysis of Genomic CAP1

C. albicans cDNAs homologous to CAP (also called SRV2) genes were used to isolate three independent genomic clones, each containing a 3.7 kb HindIII fragment (diagrammed in FIG. 2A) found in C. albicans genomic DNA (FIG. 2B, lane 1). A gene encoding an open reading frame identical to that found in the cDNA was named CAP1 because of similarities to CAP genes from other organisms as described below. The protein product of CAP1 was designated Cap1. Two, silent, nucleotide difference was found between C. albicans CAP1 and C. albicans SRV2 reported by the Stanford DNA Sequencing and Technology Center (assembly 6).

Figure 3:
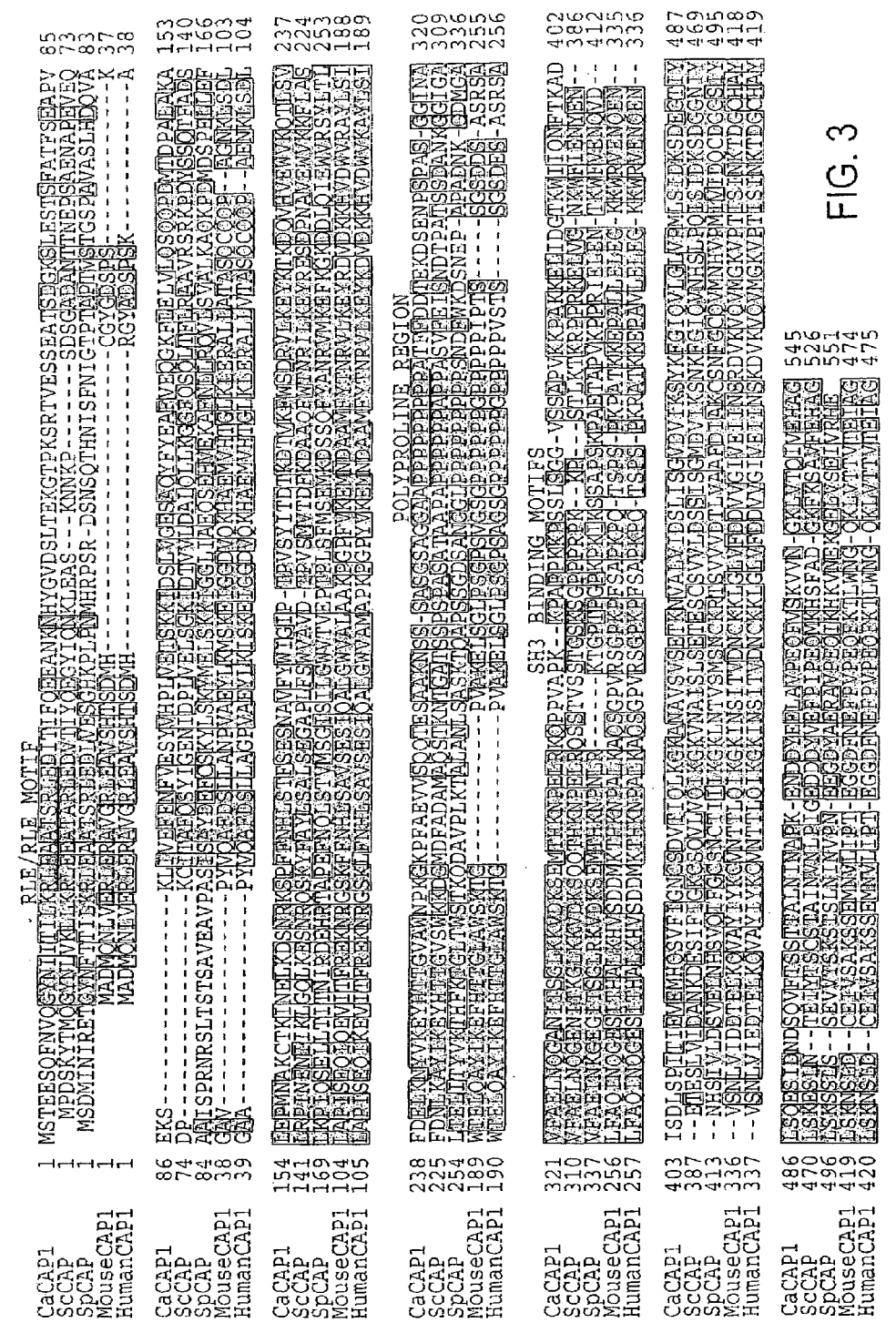

The predicted C. albicans Cap1 was 28-44% identical in overall primary amino acid sequence to CAPs from other organisms. The conserved RLE/RLE motif important for monomer association, protein localization, and Ras/cAMP dependent signaling (Shima et al., 20 MOL. CELL. BIOL. 26-33 (2000); Yu et al., supra; Zelicof et al., supra), the universally conserved and centrally-located stretch of proline residues of unknown function, and two consensus SH3-binding motifs (PXXP) were found in C. albicans Cap1 (FIG. 3). Interestingly, the first 100 amino acids of C. albicans Cap1 showed more dissimilarities to CAPs from other organisms than did the remainder of the protein. The first 100 amino acids of C. albicans Cap1 showed only 28.2 and 26.5% identity to the corresponding regions of S. cerevisiae and S. pombe CAPs, respectively, compared with 45.1 and 41.1% identity in carboxy terminal regions, respectively.

Predicted secondary structures of C. albicans Cap1 and CAP of S. cerevisiae were strikingly conserved with amino terminal halves consisting of $\alpha$-helices separated by loops with small regions of $\beta$-sheet and carboxy terminal thirds consisting of $\beta$-sheets and loops. The central domain containing prolines was predicted to be a loop in both proteins. Hydrophobicity profiles of the two proteins were also similar (Kyte and Doolittle, 157 J. MOL. BIOL. 105-32 (1982)).

Example 8

Expression of the CAP1 Gene

CAP1 was neither a highly expressed nor a developmentally regulated gene (FIG. 4). Detection of the 1.7 kb CAP1 transcript in yeast (FIG. 4A) and germ tube RNA (FIG. 4B) by Northern blotting required lone exposure times. Low mRNA abundance was consistent with unbiased codon usage in that the effective number of codons (Wright, 87 GENE 23-9 (1990)) 43.1, was typical of genes that are expressed at low levels such as PKC1 and MKC1 with values of 45 and 54.8 respectively.

Example 9

Construction of cap1/cap1 Mutant and CAP1 Complemented Strain of C Albicans

Reiterative site-specific disruption of genomic CAP1 DNA sequences with hisG-URA3-hisG or hisG produced HindIII fragments of 7.6 and 4.7 kb in size, respectively, that hybridized to probes for CAP1 (FIG. 2B) and hisG-URA3-hisG DNA. To verify that phenotypes of the cap1/cap1 mutant were caused by disruption of CAP1 genes, a complemented strain, CACRE1, was constructed by reintroducing the wild type CAP1 DNA into one of the cap1::hisG loci of the Ura⁻ cap1/cap1 mutant using co-transformation (Staab et al., 283 SCIENCE 1535-8 (1999)). CAP1 disruption was confirmed by the absence of CAP1 RNA in the cap1/cap1 mutant CAC1-1A in Northern blot analysis (FIGS. 4A and 4B). To show that read-through or truncated CAP1 mRNA was not present in the cap1/cap1 mutant, RT-PCRs were performed using CAP1-specific primers. CAP1 mRNA could not be detected using a probe (PCR-1.6) which spans the entire coding region of CAP1 (FIG. 4C). Equivalent levels of ACT1 cDNA (304 bp) were present in all strains (FIG. 4C). The cap1/cap1 mutant does not have CAP1 mRNA and cannot produce full or truncated Cap1 proteins.

Example 10

Analysis of cap1/cap1 Mutants

Growth rates of the cap1/cap1 mutant were equivalent to that of the other strains in rich media (YPD) but were reduced in minimal media (YNB) (FIG. 5). Budding appeared morphologically normal in both media.

Figure 6A:
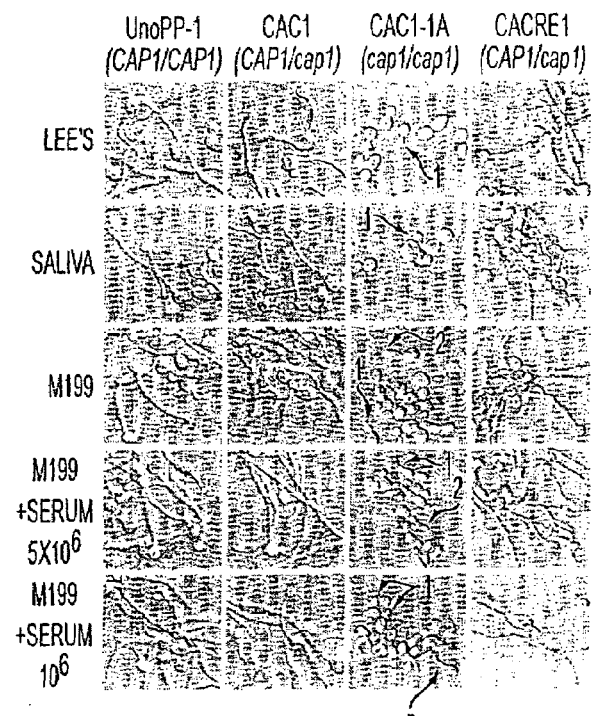
FIGS. 6A-6B depict the phenotypic analyses of cap1/cap1 mutants in liquid media. cap1/cap1 strains were defective in bud-hypha transitions. Germ tubes were induced at cell concentrations of 5×10$^6$ cells/ml (first four rows in FIGS. 6A and 6B) of 1×10$^6$ cells/ml (bottom row) in prewarmed Lee's media, saliva, M199, or M199+serum for 5 and 20 h. cap1/cap1 mutant cells formed buds (arrows "1") or pseudohyphae at low frequency (arrows "2") whereas strains having CAP1 (UnoPP-1, CAC1, and CACRE1) produced typical germ tubes (first two and fourth columns in FIGS. 6A and 6B). At 20 h a few cap1/cap1 mutant yeasts (<10%) produced germ tubes in saliva or M199 (arrows "3"). In the presence of serum the frequency of germ tube formation was higher (20-30%) (arrow "4"). Reducing the inoculum concentration in the presence of serum led to production of germ tubes by 40% of cap1/cap1 mutant yeasts at 5 h (arrow "5") and at 20 h the majority of yeasts had formed germ tubes that were shorter than those of the other strains (arrow "6"). Bars indicate a length of 5 μm.
Figure 6B:
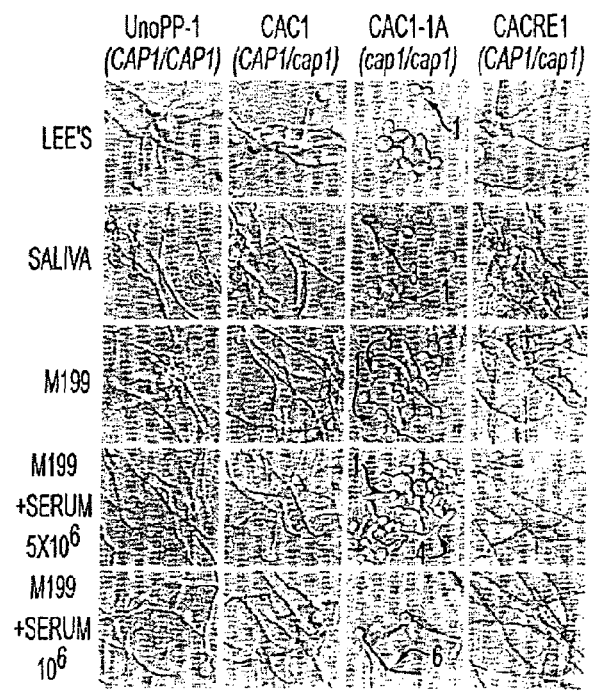

Mass conversion of yeasts to germ tubes (bud-hypha transitions) were performed in liquid media. cap1/cap1 mutants were unconditionally deficient in producing germ tubes in liquid suspension compared to CAP1/cap1 and CAP1/CAP1 strains. For the latter strains the percentages of yeasts with germ tubes approached 100% in Lee's media (pH 6.8), M119, M199 with 5% bovine serum albumin, and saliva (FIGS. 6A-6B). Media containing simple inducers also did not support germ tube production by cap1/cap1 yeasts. cap1/cap1 yeast cells in M199 with or without serum appeared elongated or pseudohyphal, but germ tubes were not seen. cap1/cap1 mutant cells budded in all conditions as determined by cell counting and differential labeling of parent yeasts with anti-C. albicans antiserum, permitting unlabeled nascent buds and yeasts produced during the incubation period to be distinguished from inoculum yeasts.

Upon prolonged incubation, germ tubes were found at low frequencies in cultures of the cap1/cap1 mutant (FIG. 6B). After 20 h of incubation in M199 and in saliva a few (<10%) cap1 yeast cells had germ tubes. In M199 containing 5% serum the percentage was higher (approximately 20-30%), resembling cultures of wild type strains inoculated at cell concentrations that exceed the threshold for germ tube formation (Hazen et al., 24 INFECT. IMMUN. 661-6 (1979)). Reducing the inoculum led to the emergence of germ tubes in approximately 40% of the cells after five hours of incubation in M1199+serum. By nine hours most cap1/cap1 mutant cells (>80%) had formed germ tubes. Germ tubes of cap1/cap1 mutant cells were shorter in length than wild type germ tubes at 20 h. Further reductions in inoculum concentration did not lead to a higher frequency of germ tube formation. Germ tube formation in the cap1/cap1 mutant in the presence of serum was deficient in that the time to form germ tubes averaged four to five times longer and average frequencies of germ tube-forming cells were reduced for cap1/cap1 mutant cells compared to strains with CAP1. Similar results were found in 10% serum with 50 mM potassium phosphate buffer (pH 6.0).

The ability of cap1/cap1 mutant cells to form germ tubes upon prolonged incubation was limited to media containing serum. Lowering the cell concentration did not enhance germ tube formation in any other media tested, including saliva or M199 without serum.

The cap1/cap1 mutant was also unconditionally deficient in producing filamentous growth on agar-containing media (FIGS. 7A-7B). CAP1 strains grew predominantly as hyphae but in some cases, pseudohyphae were also seen. The term "filamentous growth" refers collectively to the production of pseudohyphae as well as true hyphae. The periphery of colonies with circular symmetry of CAP1 strains in Spider or M199 media consisted of extended hyphae with short branches whereas hyphae in SLAD had septae with numerous buds and thick-walled terminal buds resembling chlamydospores at hyphal tips. Characteristics of CAP1 strains in asymmetric colonies in serum media were mixed, consisting primarily of numerous branched hyphae bereft of buds and infrequent filaments coated with buds. The spectrum of morphological responses exhibited by strains with CAP1 was absent in colonies produced by cap1/cap1 mutant cells that consisted of budding yeasts independent of media composition. Strains with CAP1 formed filamentous growth on YPD agar as early as one week, but cap1/cap1 mutant colonies were devoid of filamentous growth even after two weeks of culture.

A single allele of CAP1 was sufficient for normal bud-hypha transitions and filamentous growth of C. albicans. Differences in the timing of germ tube emergence or in the length of hyphae in liquid media, or in colonial morphologies in agar media between strains with one or two copies of the CAP1 gene were not observed.

Example 11

Measurement of Intracellular cAMP Levels During Germ Tube Induction

Cytoplasmic cAMP levels were measured under conditions that induce germ tubes (M199 at 37° C.) or lead to budding (M199 at 27° C.) in wild type stains. Yeasts grown to middle logarithmic phase in M199 at 27° C. were used as the inoculum. Under germ tube inducing conditions, the majority of the cells (>95%) in strains with CAP1 had germ tubes by 3 h whereas cap1/cap1 cells produced buds (FIG. 8C).

Figure 8:
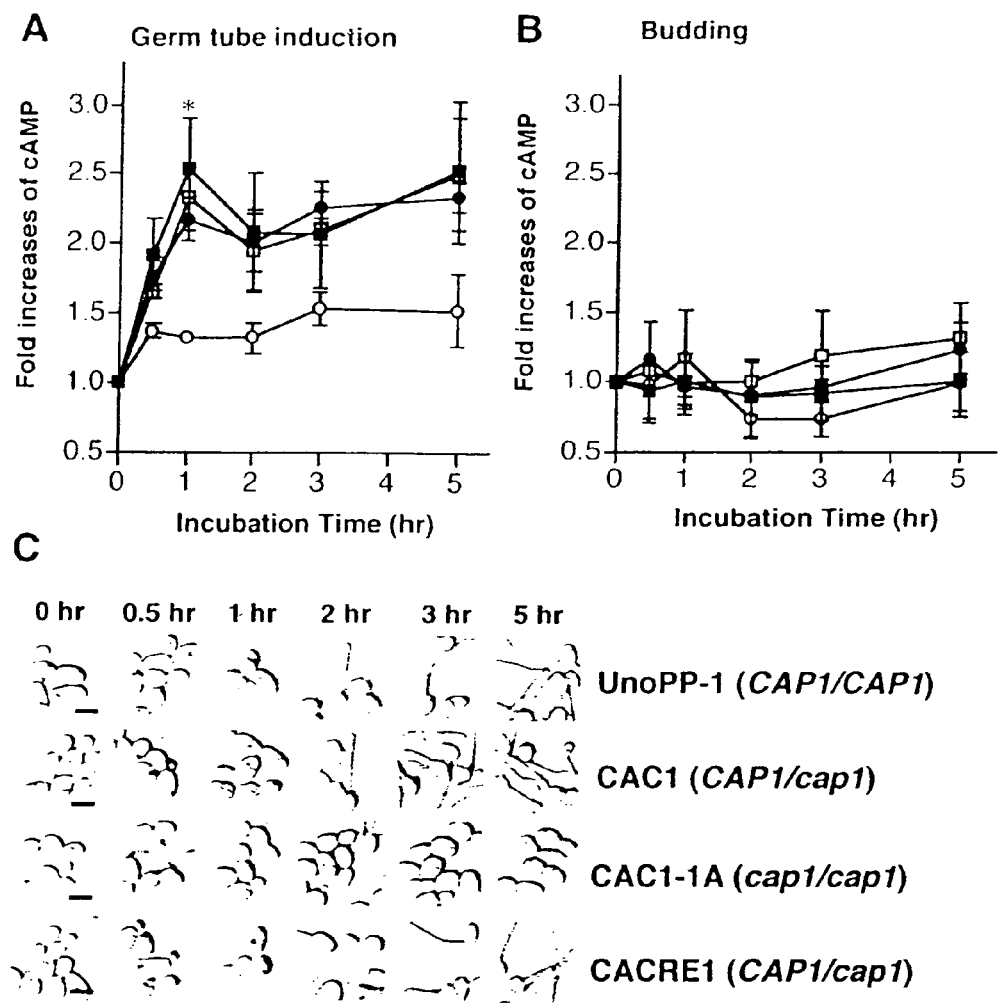
FIGS. 8A-8C depict the reduced cAMP levels of the *C. albicans* cap1/cap1 mutant in germ tube inducing conditions compared to strains with CAP1. Intracellular cAMP levels in each strain (UnoPP-1(CAP1/CAP1, □), CAC1 (CAP1/cap1, v), CACRE1 (CAP1/cap1, λ), and CAC1-1A (cap1/cap1, ○)) were measured. Each value in the Y axis indicates the fold increase in cAMP over the basal level in each strain at time zero. Error bars indicate the standard deviation of each value from three independent experiments performed in triplicate.

Intracellular cAMP levels of strains with CAP1 increased sharply after placement in induction conditions, peaking at levels that were 2 to 2.5 fold higher than initial concentrations at one hour (FIG. 8A). After a small decrease at two hours, cAMP levels gradually increased over the five-hour incubation period. Consistent with the results for germ tube induction described above, copy number effects were not seen for CAP1 in regulating cAMP levels prior to germ tube emergence. Significant differences in cAMP levels between CAP1/CAP1 and CAP1/cap1 strains were not observed. The cap1/cap1 mutant exhibited a small increase in cAMP at 30 min that plateaued, and achieved only a 1.5 fold increase over the five hour period.

The cAMP level increase in CAP1 strains was not seen under conditions where germ tubes were not induced (FIG. 8B).

Example 12

The Effect of cAMP or dbcAMP on Colonial Morphologies and Bud-hypha Transitions and of the cap1/cap1 Mutant If the reduced cAMP levels were responsible for the defective bud-hypha transitions and colonial morphologies, of the cap1/cap1 mutant, then exogenous addition of cAMP should reverse the defects. Both cAMP and dbcAMP dramatically altered the colony morphology of the cap1/cap1 mutant (FIG. 9A). Filamentous growth that closely resembled that of the positive control CAP1 strain was induced. The timing of onset of filamentous growth for CAP1 strains and for the cap1/cap1 mutant induced by cAMP and dbcAMP was the same, two days. dbcAMP was more dramatic in restoring filamentous growth to the cap1/cap1 mutant strain than cAMP (FIG. 9A), indicating that dbcAMP may be more efficiently taken up by cells than cAMP. Filamentous growth of the wild type strain also appeared to be slightly enhanced in the presence of cAMP and dbcAMP (FIG. 9A).

Hypha formation of the cap1/cap1 mutant in liquid media (M1 99+serum) was also enhanced by the addition of dbcAMP (10 mM). Hyphae of the cap1/cap1 mutant were much longer and more hyphae and pseudohyphae were seen if the media contained dbcAMP. The results appeared most dramatic at 13 h (FIG. 9B). At 3 h twice as many pseudohyphae were detected and the pseudohyphae were longer in the presence of dbcAMP. Thus the dbcAMP decreased the time required for emergence of filamentous structures. It was difficult to estimate the effect of exogenous dbcAMP on enhancing hyphal formation of the wild type strain because of extensive hyphae formation produced independent of the presence of dbcAMP (FIG. 9B). Exogenous cAMP (10 mM) produced similar but less dramatic effects on hyphal formation of the cap1/cap1 mutant.

These results are consistent with CAP1 regulation of bud-hypha transitions of *C. albicans* by modulating cAMP levels.

Example 13

CAP1 Gene is Required for Virulence in a Murine Model of Systemic Candidiasis

The role of the CAP1 gene in the pathogenesis of systemic candidiasis was investigated using male CBA/J mice (5-6 weeks of age) as previously described (Staab et al., 283 SCIENCE 1535-8 (1999)). *C. albicans* strains (SC5314 (CAP1/CAP1), CAC1 (CAP1/cap1), CAC1-1A (cap1/cap1) and CACRE1 (CAP1/cap1, revertant)) were grown to stationary phase in peptone-dextrose (PD) media. Cells were then harvested, washed, and resuspended in 0.9% NaCl at a concentration of $10^6$ cells/ml. Four groups of mice (six per group) were injected via the lateral tail vein with $2 \times 10^5$ cells in a final volume of 200 µl in two independent studies. Survival was monitored daily. Kidney tissue were cultured on YPD plated to determine colony forming units (CFU) per gram of tissue and to verify germ tube formation phenotypes. Survival curves were illustrated by the Kaplan-Meier method using the PRISM program 2.0b (GraphPad Software, San Diego, Calif.) and statistical differences between paired groups were compared using the log-rank test.

Figure 10:
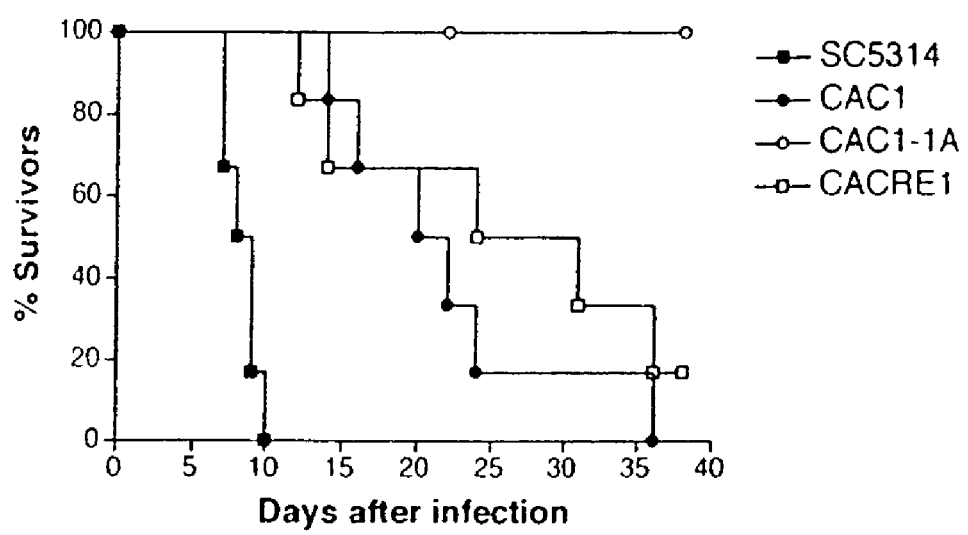
FIG. 10 depicts the survival curves of mice (CBA/J, 5-6 weeks of age) infected with $2\times10^5$ cells of C. albicans strains SC5314 (CAP1/CAP1; n=6), CAC1 (CAP1/cap1; n=6), CAC1-1A (cap1/cap1; n=6), and CACRE1 (CAP1/cap1, revertant; n=6). Similar results were obtained in two independent experiments. Survival curves were illustrated according to the Kaplan-Meier method using the PRISM program and compared using the log-rank test. A p value <0.05 was considered significant.

Mice injected with the wild type *C. albicans* strain (SC5314) expired within 10 days after injection (FIG. 10). *C. albicans* strains with a single copy of the CAP1 gene (CAC1 and CACRE 1) showed reduced virulence when compared with the parental CAP1/CAP1 strain (p=0.0006) but 80% of the mice became ill and were sacrificed by 35 days (FIG. 10). In contrast, six mice given the cap1/cap1 mutant survived and behaved normally during the entire period of observation (FIG. 10). Survival of mice injected with the cap1/cap1 mutant was significantly reduced relative to control strains (SC5314 vs. CAC1-1A, p=0.0006; CAC1 vs. CAC1-1A, p=0.0007; CACRE1 vs. CAC1-1A, p=0.0069). No statistically significant difference was found between the heterozygous CAP1/cap1 mutant (CAC1) and the revertant (CACRE1) (p=0.3661). Colony-forming units of *C. albicans* were detected in sacrificed mice injected with CAP1 strains ($10^7$ cfu per gram kidney). Of the 6 mice injected with the cap1/cap1 mutant, three had infected kidneys ($1.9 \times 10^8$ cfu per gram kidney) and three cleared the infection. Yeasts isolated from kidneys of mice that received the cap1/cap1 mutant showed the same defects in forming germ tubes as those used for intravenous injection, verifying the authenticity of strains and the importance of delayed germ tube formation in virulence.

The avirulence of the cap1/cap1 mutant extends the findings of other studies (Calera et al., 68 INFECT. IMMUN. 518-25 (2000); Calera et al., 67 INFECT. IMMUN. 42804 (1999); Lo et al., 90 CELL 939-49 (1997); Schweizer et al., 38 MOL. MICROBIOL. 43545 (2000); Yamada-Okabe et al., 181 J. BACTERIOL. 7243-7 (1999)) in showing that the ability to produce hyphae with normal kinetics as well as the absolute ability to produce hyphae is important for candidiasis. The avirulence of cap1/cap1 mutants is also supportive of an important role for the cAMP signaling pathway in growth of *C. albicans* in host tissue. The rapid production of hypha-specific factors such as the Hwp1 adhesin (Staab et al., SCIENCE, supra) and others (Schaller et al., 34 MOL. MICROBIOL. 169-80 (1999); Staib et al., supra) coincident with germ tube formation are likely to be important for systemic candidiasis in mice. The virulence study shows that *C. albicans* joins other pathogenic fungi in the involvement of the cAMP signaling pathway in pathogenesis. Disruption of the gene encoding the catalytic subunit of cAMP dependent PKA and disruption of the GPA1 gene affect the virulence of *M. grisea*, and *Cryptococcus neoformans*, respectively.

Example 14

Gene Expression Analysis

Gene expression analysis using microarray technology may be useful in the context of a diagnostic kit for candidiasis or to affirm expression or lack thereof of mutant strains of *C. albicans*. It is desirable to include in the sample of target nuclei acids, a labeled set of standard DNA molecules that are present in known amounts and can be used as calibrating agents in subsequent analysis. The standard may be provided by reverse transcribing the standard RNA into end-labeled cDNA under conditions substantially the same as, and preferably identical to, the conditions used to prepare the labeled target nucleic acid sample. The resultant end-labeled standard is then printed in an allocated area of the microarray.

Methods of isolating RNA from cells, tissues, organs or whole organisms are known to those of skilled in the art and are described in SAMBROOK ET AL., (supra). Isolated sample mRNA is reverse transcribed into end-labeled target nucleic acid by hybridizing an appropriately labeled oligo(dT) primer to the mRNA under conditions sufficient for enzymatic extension of the hybridized polymer. The primer is sufficiently long to provide for efficient hybridization to the polyA tail. Alternatively, for amplification of fragments of sample mRNA, one may optionally provide for a short sequence 3' of the oligo dT region, where the dNTP immediately adjacent to the oligo dT region will not be a dTTP and usually the sequence will comprise no dTTP. The primer will carry the label, as described above. The primer is incubated with the mRNA in the presence of reverse transcriptase and other reagents necessary for primer extension under conditions sufficient for first strand cDNA synthesis, where additional reagents include dNTPs; buffering agents, e.g. Tris.Cl; cationic sources, both monovalent and divalent, e.g. KCl, $MgCl_2$; RNAase inhibitor and sulfhydryl reagents, e.g. dithiothreitol; and the like. DNA polymerase can be used for the first strand cDNA synthesis step.

First stand synthesis is completed by adding isolated RNA and the appropriate primer. The primer/RNA mix is incubated followed by the addition of first strand reaction buffer, DTT, dNTPs, RNasin®, and Superscript™ II (GIBCO-BRL) to the mix. Following a second incubation period, second strand synthesis buffer, dNTPs, DNA polymerase, RNase, DNA ligase, and RNase-free water are added. Following a third incubation period, DNA polymerase is added to each sample. Following a fourth incubation period, the cDNA is extracted and washed 3× with water in a column. After collection from the column, the cDNA is dried for in vitro transcription.

A transcription kit may be used to amplify RNA. In a microfuge tube, double-stranded cDNA, RNA polymerase buffer, ATP, CTP, GTP, UTP, DTT, and RNA polymerase are added and then incubated. The amplified RNA is washed 3× in a column, collected, and dried.

Amplified RNA (aRNA) from the first round amplification is mixed with random hexamers, incubated, chilled on ice, and then equilibrated at room temperature. For the initial reaction, first stand buffer, DTT, dNTPs, RNasin®, and reverse transcriptase are added to the aRNA mix, and then incubated. RNase is then added and the sample is incubated again. For second strand cDNA synthesis, primer is added to the aRNA reaction mix and the sample is incubated. Second strand synthesis buffer, dNTPs, DNA Polymerase, RNase, DNA ligase, and RNase-free water are added to the sample mix and the sample is incubated again. DNA polymerase is then added followed by sample incubation. The double-stranded cDNA is extracted to remove extraneous protein and purified to remove the unincorporated nucleotides and salts.

aRNA and random hexamers are mixed in a solution containing RNase-free water, heated, and then chilled on ice. For the labeling reaction, first strand buffer, DTT, RNasin®, d(GAT)TP, dCTP, labeled-dCTP, and reverse transcriptase are added to the aRNA mix and incubated at room temperature. The aRNA template is degraded and the sample incubated again at a suitable temperature. The probes are purified with Microcon® 30 Columns and Qiagen® Nucleotide Removal Columns. The probes are vacuum-dried and resuspend in hybridization buffer.

Microarray matrices are treated to ensure amino-linkage of cDNAs to the slides, and then are boiled in water to denature the cDNA. Labeled probes are heated, cooled to room temperature, and then applied to the slides. The slides are covered with glass cover slips, sealed with DPX (Fluka) and hybridized.

At the end of hybridization, the slides are cooled to room temperature. The slides are washed and are ready for scanning. In order to evaluate the relationship between hybridization signal and sample probe concentration, hybridization intensity is measured as a function of concentration of the RNAs for one or more of the target genes. Sample RNA concentration is compared with standard RNA concentration to determine expression level.

Example 15

Identify Potential Virulence Genes that are Activated by Signaling Pathways Involving Cap1 Protein Using Microarray Technology By way of example, one may identify potential virulence genes that are activated by signaling pathways involving Cap1 protein using microarray technology. The strategy is to compare mRNA's from the cap1 gene null mutants to parent strain mRNA to identify individual transcripts that are absent in the mutant and present in the parent or in the heterozygous CAP1/cap1 gene mutant. The basic approach is to use RNA from the isogenic strains with or without the Cap1s that were grown in hyphae-inducing conditions, such as M199 at 37 degrees C., to prepare labeled cDNA. RNA samples are taken at 1 and 2 h after induction. The analysis for this approach involves the identification of transcripts that are absent or greatly reduced in the mutant compared to the other strains using microarrays. The microarrays may be used to compare gene expression in the mutant to parental and/or revertant strains.

Figure 11:
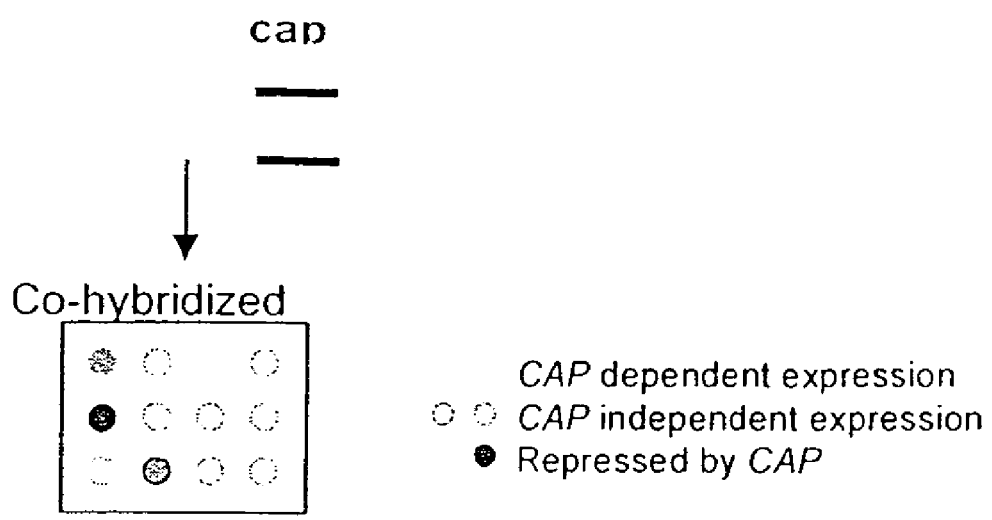
FIG. 11 depicts the identification of potential virulence genes that are activated by signaling pathways involving Cap1 protein using microarray technology.

C. albicans microarrays are produced by methods known to those skilled in the art. For comparing gene expression in the cap1 gene null mutants to parental or revertant strains, poly $A^+$ mRNA from the two strains are reverse transcribed to form cDNA's which are labeled with different fluorescent dyes (red Cy3 for the mutant reference cDNA or green Cy5 for the strain with a wild type CAP1 gene) and co-hybridized onto a single array as previously described to be read with a confocal laser scanning microscope (see FIG. 11). The quantitative ratio of green to red signal for each spot (gene) reflects the relative abundance of the each labeled cDNA hybridized to the spot (gene) between the two experimental samples. A gene whose transcription depends on Cap1 is greatly reduced in the cap1/cap1 mutant compared to the parent or revertant, and will hybridize a relative abundance of green wavelength-labeled cDNA compared to genes whose expression do not depend on the mutated gene. Virulence genes (or housekeeping genes that are controlled by the CAP1 gene) will also give high green to red ratios, genes that do not depend on the CAP1 gene will be equally abundant in green and red wavelengths, appearing yellow, and genes that are repressed by the CAP1 gene will have a low abundance of green color and will be red.

HWP1 DNA serves as a standard for the degree of difference (ratio of green dye-labeled cDNA in the parental relative to the mutant strain) that would be expected for other genes regulated in a similar manner and to verify that the design successfully identifies genes controlled by the CAP1 gene.

To confirm the results from array experiments, the identified putative virulence genes are cloned and used to prepare probes for Northern blotting, to show that their transcripts have the predicted pattern of expression in the CAP1 mutant compared to the parental strain.

The genes that depend on Cap1 for expression are analyzed by standard homology searches in order to gain insight into the functional category of the gene product; cell wall protein, metabolism, signal transduction, secretion and others. Genes that are predicted to function specifically in host interactions and have motifs suggestive of adhesins, proteinases, phospholipases, and those that resist toxic oxygen and nitrogen radicals produced during host defense are selected for creation of null mutants and virulence assays in animal models. In contrast, housekeeping genes will not be pursued for a role in pathogenesis, but will be used to predict metabolic pathways employed by C. albicans when growing in host cells. The identity of the genes will form the bases of new hypotheses about pathogenic mechanisms that will be directly testable in the following aim. These experiments have a very high probability of revealing a Cap1-dependent set of genes that C. albicans deploys that permits invasion and proliferation in host tissues.

Mini and microarray approaches to pathogenic questions will be extremely important for advancing knowledge about C. albicans because of the present inability to employ random mutagenesis approaches with this diploid organism. Furthermore, the availability of membranes and/or chips for C. albicans is imminent.

Example 16

Identification and Disruption of the C. Albicans PDE2 Gene C. Albicans Strains and Growth Condition C. albicans strains used in this study are listed in FIG. 12. Yeast forms were grown in yeast extract peptone (YPD) or yeast nitrogen base containing 50 mM glucose (YNB) at 30° C. for 48 h. Germ tubes were induced at 37° C. in medium 199 (M199, Gibco-BRL), M199 with 5% bovine calf serum, and Lee's media (pH 6.8)(Lee et al., 13 SABOURAUDIA 148-153 (1975)) using an inoculum of $5 \times 10^6$ cells/ml. For growth analysis in agar-containing media, stationary-phase yeasts were mixed (200 cells/25 ml of medium) with liquefied agar Spider medium (Liu et al., 266 SCIENCE 1723-1726 (1994)), SLAD (synthetic low ammonium dextrose)(Csank et al., 66 INFECT. IMMUN. 2713-2721 (1998)), and 2% agar containing 4% bovine calf serum (Lo et al., 90 CELL 939-949 (1997).

Cell morphologies were examined using differential interference contrast microscopy (OLYMPUS BX60) with a 40× or 20× objective and photographed (OLYMPUS Magnafire, model S99806). Colonial morphologies were observed using a stereoscope (OLYMPUS SZX12)(1× objective) with a transmitted light console base. Photographed images were processed using Adobe PhotoShop 2.5.

Example 17

Cloning of the C. Albicans PDE2 Gene

A 3-kbp DNA segment containing an open reading frame with sequence similarity to the S. cerevisiae PDE2 ene was synthesized by PCR (Taq polymerase) using SC5314 genomic DNA as a template and the following oligonucleotides:

```
PDE2-5UR1
(5'-GCAAATAAATCCGTAGGAAACG-3');   (SEQ ID NO. 6)
and

PDE2-3UR1
(5'-CCACCAACACCAACAGAAAA-3').     (SEQ ID NO. 7)
```

This PCR product, which included a 650-bp 5' UTR, a 1713-bp entire open reading frame (ORF), and a 637-bp 3' UTR of PDE2 was cloned into the pBluescript SK(–) T vector, generating pPDE2.1. The 3-kbp PDE2 insert of pPDE2.1 was confirmed by automated DNA sequencing (ABI Prism, model 377 and 373, Perkin-Elmer Co., Boston, Mass.). The predicted amino acid sequence of PDE2 in pPDE2.1 (570 amino acids) was identical to that of Pde2 in the Stanford Candida genome database (Seq ID No. 8) described above, except that a string of threonines at position 64 to 74 was reduced by one in the cloned fragment compared to the Stanford sequence. The shorter length of the threonine string was also present in an independent clone of the PDE2 gene to create pPDE2W (see below) suggesting that the shorter string of threonines reflects the sequence of genomic DNA of SC5314. In the previously reported amino acid sequence from PDE2 gene of C. albicans strain 1161 in GenBank database, accession number CAA21984 (SEQ ID NO. 9), the string of threonines was broken by an alanine (64TTTTTTTATTT74) (SEQ ID NO. 10) suggesting frequent variability in this region.

Plasmid pPDE2.1 was used for construction of PDE2 disruption cassette and to construct the revertant described infra. Plasmid pPDE2.1M was constructed from pPDE2.1, by removal of the EcoRI site in pBluescript SK(–) using the GeneEditor in vitro site-directed mutagenesis system (Promega, Madison, Wis.). The unique EcoRI site of pPDE2.1M within the PDE2 gene could then be used for generating the PDE2 disruption plasmid. Escherichia coli JM109 served as the host strain for transformation and propagation of pPDE2.1 and pPDE2.1M.

Example 18

Disruption of the C. Albicans PDE2 Gene

To disrupt the PDE2 gene in C. albicans, plasmid pPDE2.1MdURA3 was constructed by replacing 1388-bp (+323 to +1710, relative to ATG) of the coding region including the highly conserved phosphodiesterase signature sequence and 232-bp of the 3' untranslated region (UTR) of PDE2 with the 4.0-kbp BamHI-BglII digested hisG-URA3-hisG cassette from p5921 (Fonzi and Irwin, 134 GENETICS 717-728 (1993)). The pPDE2.1M was cleaved by EcoRI and AflII, treated with Klenow fragment (Gibco-BRL, Carlsbad, Calif.) to generate blunt ends, and ligated to a similarly treated hisG-URA3-hisG cassette having blunt ends.

E. coli HB101 served as the host strain for transformation and propagation of the plasmid, pPDE2.1MdURA3. Plasmid pPDE2.1MdURA3 was linearized by digestion with BamHI and KpnI, and 10 μg of DNA was used to transform Ura-C. albicans by the spheroplast method (Kurtz et al., 6 MOL. CELL BIOL. 142-149 (1986)).

Integration of disrupted PDE2 DNA at the PDE2 locus was verified by Southern blotting using HindIII- or EcoRI digested genomic DNA prepared using the MasterPure yeast DNA purification kit (Epicentre, Madison, Wis.)(FIG. 14B). Southern blots were probed with a 1713-bp fragment containing the entire coding region of PDE2, which was generated by PCR using SC5314 genomic DNA and the following two oligonucleotides:

```
PDE2W-R1
(5'-GGGATGGCAGAAGTATTATCATT-3');     (SEQ ID NO. 11)
and

PDE2W-F1
(5'-GGGCTGCAGTTATTTCTTTGCTCTTTCCA-3').  (SEQ ID NO. 12)
```

The probes were labeled using the enhanced chemiluminescence (ECL) direct nucleic acid labeling and detection system (Amersham, Piscataway, N.J.). The heterozygous PDE2/pde2 mutants, BPS1 and BPS16, were isolated by transformation of the Ura-strains, CAI4 (Fonzi and Irwin, 1993) and CAC1-1A1 (Bahn and Sundstrom, 2001)(FIG. 14B, lane 1 and 7), respectively, with the PDE2 disruption cassette.

The PDE2/pde2 isolates exhibited a predicted 11.4-kb hybridization band for a disrupted PDE2 allele (pde2:: hisG-URA3-hisG), and two bands of 3.0 and 5.8-kb corresponding to the wild type allele (FIG. 14B, lanes 2 and 8). The Ura-derivatives with PDE2 disrupted by a single copy of hisG were selected in YNB media (0.002% uridine) containing 0.05% 5-fluoroorotic acid (5-FOA) (Boeke et al., 197 MOL. GEN. GENET. 345-346 (1984)) and exhibited the expected size of a 8.5-kb pde2:: hisG hybridization band (FIG. 14B, lanes 3 and 9).

The homozygous pde2/pde2 and cap1/cap1 pde2/pde2 mutants, BPS4 and BPS 18, were constructed by the second round of transformation of Ura-BPS2 and BPS 17, respectively, with the PDE2 disruption cassette. The predicted hybridization pattern of an 8.5-kb of pde2::hisG allele and an 11.4-kb of pde2::hisG-URA3-hisG allele was observed in the pde2/pde2 mutants (FIG. 14B, lanes 4 and 10). Two independent homozygous pde2/pde2 mutants were isolated from the wild type and cap1/cap1 mutant genetic background (FIG. 12).

To rule out the possibility that the genetic location of the URA3 selectable marker may affect the phenotypic analysis of pde2 mutants, homozygous pde2/pde2 and cap1/cap1 pde2/pde2 mutants having URA3 targeted to the ENO1 locus were constructed by transforming Ura-BPS7 and BPS20 (FIG. 12) with the XhoI/XbaI digested linearized eno1::URA3 fragment of p24enura (Postlethwait and Sundstrom, 177 J. BACTERIOL. 1772-1779 (1995)). The targeted integration of eno1::URA3 into each strain described supra was confirmed by Southern analysis.

To complement pde2/pde2 and cap1/cap1 pde2/pde2 mutants with the wild type PDE2, pde2/pde2 and cap1/cap1 pde2/pde2 mutant strains (BPS7 and BPS20, respectively) were cotransformed with the 3-kbp PDE2 insert of pPDE2.1 and the eno1::URA3 fragment of p24enura as a selectable marker (FIG. 14B, lanes 6 and 12)(Postlethwait and Sundstrom, supra; and Staab et al., 283 SCIENCE 1535-1538 (1999)). Three revertants were isolated. In the one revertant, BPS9, a single allele of pde2:: hisG was replaced with PDE2 (FIG. 12), whereas both alleles of pde2 were replaced with wild type PDE2 genes in the revertants, BPS10 and BPS11 (data not shown).

Example 19

Overexpression of PDE2

The 1713-bp ORF of PDE2 (SEQ. ID. NO. 13) was amplified by PCR (Pfu polymerase) using SC5314 genomic DNA and the two oligonucleotides, PDE2W-R1 and PDE2W-F1 as described above. This PCR product was cleaved with PstI, ligated to the SmaI/PstI digested pBluescript SK(−), and transformed into *E. coli* JM 109, generating pPDE2W. The correct sequence of the entire PDE2 coding region was confirmed by automated DNA sequencing. The PDE2 insert was isolated by SmaI/PstI digestion of pPDE2W and treated with T4 DNA polymerase (Promega, Madison, Wis.) to generate blunt ends. Next, the 734-bp of yEGFP3 was removed from the plasmid, pENO1GFP3, which has the ENO1 promoter upstream of yEGFP3 by double digestion with HindIII and PstI, which was followed by T4 DNA polymerase treatment to generate blunt ends. The 1713-bp PDE2 insert was ligated to the HindIII/PstI fragment of pENO1GFP3, and transformed into *E. coli* TOP10 generating pENO1PDE2-3. For targeting to the ENO1 locus, pENO1PDE2-3 and pENO1GFP3 (control plasmid) linearized at the unique ClaI site within the ENO1 coding region were transformed into Ura-*C. albicans* CAI4 as described above. Integration of ClaI-digested linearized pENO1PDE2-3 and pENO1GFP3 into ENO1 locus were confirmed by Southern blot analysis.

Example 20

RT-PCR

RT-PCR was performed as previously described (Bahn and Sundstrom, supra) using the oligonucleotides PDE2W-R1 and PDE2W-F1. ACT1 cDNA (304 bp) amplified using the following two ACT1-specific primers:

ACT-3R (5'-GGAGTTGAAAGTGGTTTGGTCAATAC-3'); (SEQ ID NO. 14)

and

ACT-5L (5'-GGCTGGTAGAGACTTGACCAACCATTTG-3') (SEQ ID NO. 15)

served as a control (Naglik et al., 1999).

Example 21

Northern Blot Analysis

For analyzing expression patterns of PDE2 in wild type strain (SC5314) and the cap1/cap1 mutant (CAC1-1A), total RNA was isolated from different growth phases of yeast cultures (early, middle, and late logarithmic, and early stationary phases) in YNB at 30° C., or from germ tubes of various time points (0, 10, 20, 30, 45, 60, 90, 120, 180, 300, and 420 minutes) cultured in M199 at 37° C. The probe for PDE2 was the 1713-bp PCR fragment of PDE2 as described previously and the probe for HWP1 was the gel-extracted 609-bp HWP1 insert of a phagemid clone (pBS+13) (Staab et al., 271 J. BIOL. CHEM. 6298-6305 (1996)). As a probe for loading control, a 687-bp PCR product of the 18S 30 rRNA gene of *C. albicans* SC5314 was generated as previously described (Bahn and Sundstrom, supra; and Makimura et al., 40 J. MED. MICROBIOL. 358-364 (1994)). Methods for electrophoresis in formaldehyde gels, transfer, radiolabeling of probes, hybridization, and molecular size determination were similar to those previously described (Bahn and Sundstrom, supra; and Staab et al., 1996, supra) except for the following: the blots were hybridized first with the PDE2 probe (107 cpm), autoradiographed (2 day exposure), and then hybridized with the 18S rRNA probe ($2 \times 10^6$ cpm). For detection of HWP1, the same blots were stripped by repeated boiling in a 0.05×SSC solution containing 10 mM EDTA (pH8.0) and 0.1% SDS (Sambrook et al., supra), and re-hybridized with the HWP1 probe ($4 \times 10^6$ cpm). Quantitative analysis was performed by normalizing amounts of PDE2 RNA in indicated time points with 18S rRNA by using Phosphorimaging analysis and ImageQuant software (Molecular Dynamics, Piscataway, N.J.). Fold induction was calculated by dividing normalized amount of PDE2 RNA in each indicated time point by that in a zero time point.

To determine whether PDE2 is constitutively overexpressed in strains integrated with pENO1PDE2-3 (EPDE2-3) as compared to the control strain (EGFP3), yeast cells were grown to the stationary phase in YNB at 30° C. for 48 hours, washed, and resuspended in 1×PBS. For total RNA purification, yeast cells were inoculated at a concentration of $5 \times 10^6$ cells/ml into the pH4.5 of Lee's media (25° C.) for budding growth or pH6.8 of Lee's media (37° C.) for germ tube induction. After a 3 hour period of incubation, total RNA (10 μg/lane) was isolated and analyzed by Northern blot with probes specific to PDE2 and 18S rRNA as described before. The membrane was exposed to X-ray film overnight for detection of PDE2 mRNA and for 4 hours for detection of 18S rRNA. Fold induction was calculated by dividing amount of PDE2 RNA normalized by 18S rRNA in EPDE2-3 by that in the control strain.

Example 22

Test for Sensitivity to Exogenous cAMP

*C. albicans* strains were grown in YNB at 30° C. to middle-logarithmic phase, and then an equal number of cells were subcultured into YNB or YNB containing 4 mM and 40 mM cAMP and grown for 6 to 9 hours. Every hour during incubation, optical density and cell number/ml of cultures were measured by a photoelectric colorimeter (Klett-Summerson, Klett MFG. Co., Inc, NY, N.Y.) and hemacytometer, respectively. The percent of dead cells was determined by staining with 0.1% methylene blue (Sigma, St. Louis, Mo.). Also, cell morphologies were observed by microscopy. After a 6-hour incubation of each strain with YNB containing the indicated amounts of exogenous cAMP, culture samples were serially diluted, spread on YPD plates, and incubated for 2 days to determine the number of colony forming units (CFU). The percent relative growth was calculated by using the following formula:

[(*CFU* of a strain incubated for 6 h in YNB having an indicated concentration of cAMP)/(CFU of the strain incubated for 6 h in YNB only)]×100%.

Example 23

Indirect Immunofluorescence Assay

Indirect Immunofluorescence assays (IFAs) were performed, as previously described (Staab et al., 1996, supra) using a rabbit polyclonal antiserum raised against a recombinant Hwp1 as a primary antibody (Cov1) at a dilution of 1:200 and fluorescein isothiocyanate (FITC) conjugated goat anti-rabbit IgG (Zymed, San Francisco, Calif.) as a secondary antibody at a dilution of 1:50. Cov1 was raised against the recombinant Hwp1 comprised of amino acids 40-187 produced in *Pichia pastoris* (Staab et al., 1996, supra). Naive rabbit serum was used as negative control. Naturally occurring anti-*Candida* antibodies were removed from the sera by adsorption to SC5314 yeasts (Staab et al., 1996, supra), prior to use IFAs. FA Rhodamine (Difco, Sparks, Md.) was used as a counterstain at a dilution of 1:30.

Example 24

Test for Sensitivity to Nutrient Deprivation and Glycogen Accumulation

*C. albicans* strains were grown to stationary phase in YNB at 30° C. for 2 days, washed, resuspended in 1×PBS at a concentration of $10^4$ cells/ml, and incubated at either 30° C. or 37° C. for 24 hours. Resuspended cells were spread onto YPD plates after 0, 4, 8, 16, and 24 h of incubation and incubated at 30° C. for 2 days. To determine the CFU, percent survival of *C. albicans* strains in each time point during incubation in PBS were calculated by the following formula:

[(CFU of a strain at indicated time point of PBS incubation)/(CFU of the strain incubated at zero time point]×100%.

Level of glycogen accumulation of each *C. albicans* strain was examined by iodine/iodide staining as previously described (Toda et al., supra). Briefly, the indicated *C. albicans* strains were streaked on YPD plates, and grown for 2 days at 30° C., then 10 ml of 0.2% iodine/0.4% potassium iodide was gently applied to cover the colonies, and the plates were photographed after 2 minutes.

Example 25

Virulence Studies

*C. albicans* strains having URA3 targeted and integrated at the ENO1 locus (UnoPP-1 (WT), BPS13 (PDE2/pde2 heterozygotes), BPS15 (pde2/pde2 homozygotes), BPS9 (PDE2 revertant), and CAC1-1A1E1 (cap1/cap1 homozygotes)) were used in this study (FIG. 12). The cells were grown in YNB at 25° C. for 2 days, harvested, briefly sonicated, washed, and resuspended in pyrogen-free 0.9% NaCl at a concentration of $5 \times 10^7$ cells/ml.

Five groups of BALB/c mice (six mice per group) were injected via the lateral tail vein with $5 \times 10^6$ cells in a final volume of 100 μl. The kidneys were bisected longitudinally and one half from each kidney was used to determine CFU/gram kidney on YPD plates and the other halves were examined histologically. Survival curves were demonstrated by the Kaplan-Meier method using the PRISM program 2.0b (GraphPad Software, San Diego, Calif.) and statistical difference was analyzed by the log-rank test.

Authenticity of the strains was verified both phenotypically and genotypically. For phenotypic analysis of strains, colony morphologies on YPD plates and germ tubes induced in M199 at 37° C. were observed as previously described. For genotypic analysis of strains, Southern blots were performed with HindIII-digested genomic DNA isolated from strains recovered from kidneys of each mouse. The membrane was probed with the 1713-bp PDE2 probe previously described or the CAP1 probe (PCR-1.6)(Bahn and Sundstrom, supra). For histological analysis, halves of kidneys from each mouse were fixed in 1×PBS containing 0.5% formalin, placed in parafilm blocks, sectioned, and stained with periodic acid-Schiff reagent.

Example 26

Analysis of Undisrupted and Disrupted PDE2 DNA at the PDE2 Locus

To search for open reading frames (ORFs) in the SC5314 (Gillum et al., 198 MOL. GEN. GENET. 179-182 (1984) *C. albicans* genome database (the Stanford DNA sequencing and Technology Center, found on the world wide web at sequence.stanford.edu/group/*candida*) encoding a PDE2 gene, a BLAST search using the entire amino acid sequence (571 amino acids) of *S. cerevisiae* Pde2 (also called Sra5) was performed. One ORF, 1713-bp in length, was found on Contig6-2423 and its predicted amino acid sequence showed 28.2% homology to that of *S. cerevisiae* PDE2. The amino acid sequence differed at three positions of the non-conserved regions of Pde2 in *C. albicans* strain 1161 that had previously been reported (GenBank Accession Number CAA21984, (Tait et al., 21 FUNGAL GENET. BIOL. 308-314 (1997)(10L, 71T, and 509D in Pde2 of SC5314 strain versus 10S, 71A, and 510H in Pde2 of 1161 strain). A highly conserved 3', 5' cyclic nucleotide phosphodiesterase signature sequence was found between amino acid 333 to 484 (FIG. 13). Null pde2/pde2 mutants were derived from *C.* albicans CAI4 (wild type) and the cap1/cap1 mutant (CAC1-1A1) to study the function of PDE2 in morphogenesis and to investigate the relationship between PDE2 and CAP1 (FIG. 12). PDE2 genes were disrupted with the Urablaster system (Fonzi and Irwin, supra) as described above and illustrated in FIG. 14A. The 3-kbp rescue fragment containing the wild-type PDE2 gene was re-introduced into pde2/pde2 (BPS7) and pde2/pde2 cap1/cap1 (BPS20) strains by co-transformation together with the eno1::URA3 fragment as described previously (Bahn and Sundstrom, supra; and Staab et al., supra). Integration of PDE2-disrupted and undisrupted DNA at the PDE2 locus was verified by Southern blot analysis of HindIII-digested genomic DNA of each strain probed with the entire PDE2 ORF (FIG. 14B). To confirm that the PDE2 genes had been inactivated in the null mutants, RT-PCR analysis was performed using oligonucleotides that amplify the entire ORF of PDE2 (FIG. 14C). PDE2 cDNA was not detectable in pde2/pde2 and cap1/cap1 pde2/pde2 mutants, whereas equivalent levels of ACT1 cDNA were found in all strains (FIG. 14C, lanes 3 and 7). Expression of PDE2 was recovered in revertant strains (FIG. 14C, lanes 4 and 8, data not shown for BPS10 and BPS 11).

It has be reported that the genetic location of URA3 selectable marker may affect the interpretation of phenotypic analysis of mutants made by Ura-blaster mutagenesis (Sundstrom et al., 2002b, supra). To separate the URA3 auxotrophic marker from the gene of interest, PDE2, and to place the URA3 gene at the same position in complemented and mutant strains, homozygous pde2/pde2 mutants having the URA3 gene targeted to the ENO1 locus were generated. These strains are isogenic with the control strain UnoPP-1. The strains were constructed by transformation of Ura-pde2/pde2 and cap1/cap1 pde2/pde2 strains with the eno1::URA3 fragment (Postlethwait and Sundstrom, supra)(BPS15 and BPS27, FIG. 12). No phenotypic differences were observed between the strains with URA3 located at ENO1 as compared to those with URA3 located in the coding region of PDE2.

Example 27

The pde2/pde2 Mutants are Hyperfilamentous

Figure 15:
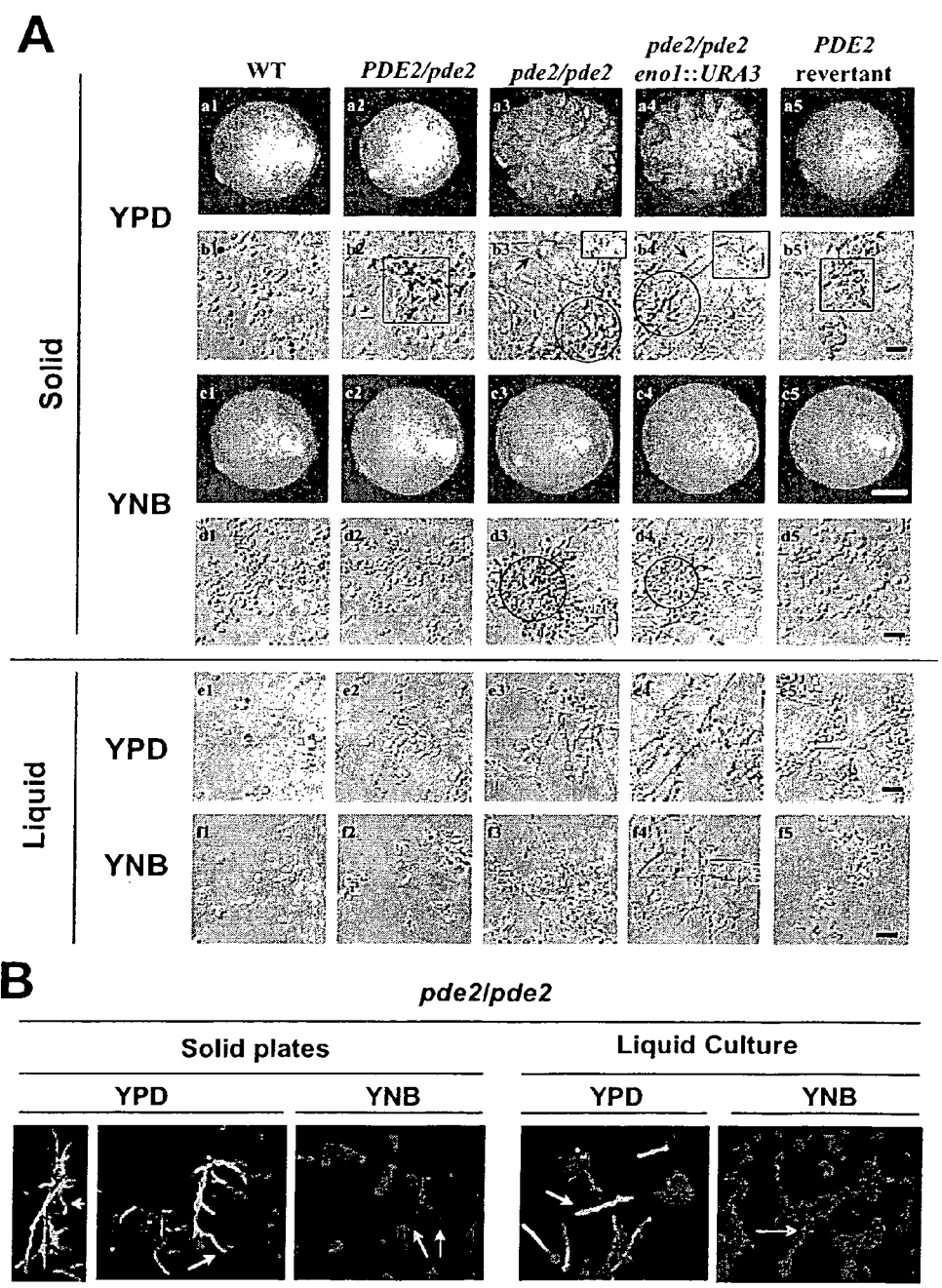
FIGS. 15A-15B depict hyperfilamentous growth of strains with mutations in the PDE2 gene.

Under conditions that normally cause wild type strains to form smooth colonies composed of budding yeasts on YPD agar media, the homozygous pde2/pde2 mutant formed colonies that appeared wrinkled, neither the heterozygous PDE2/pde2 mutant or the revertant, however, formed wrinkled colonies. The wrinkled colonies were mixtures of yeast and filamentous forms, and the yeasts appeared more elongated than yeasts from smooth colonies formed by wild type cells (FIG. 15A). These filamentous cells were also highly aggregated (FIG. 15A, second row). The wrinkled colony phenotype and extent of filamentation depended on the media and PDE2 gene copy number. On YNB media, even though colonies formed by the pde2/pde2 mutant were smooth, elongated yeasts and pseudohyphae but not true hyphae were present (FIG. 15A, third and fourth rows). When streaked on the surface of Spider media (data not shown), the homozygous pde2/pde2 mutant formed extensively wrinkled colonies as compared to those found on YPD. Colonies formed by the heterozygous PDE2/pde2 mutant and the revertant grown on the surface of Spider media, however, differed from those grown on YPD in that colonies were mildly wrinkled, exhibiting a ring-shaped appearance. Thus hyperfilamentous growth was most pronounced on Spider media, but was also seen on YPD and YNB.

Cell aggregation was correlated with hyperfilamentous growth and appeared to be a sensitive indicator of PDE2 gene inactivation. Hyphae of the pde2/pde2 mutant were massively aggregated on YPD. Even the elongated yeasts and pseudohyphae formed by the pde2/pde2 mutant on YNB were aggregated as well as the elongated cells of the PDE2/pde2 mutant grown on YPD (FIG. 15A). The hyperfilamentous growth of the mutant strains in liquid media was similar to that seen in solid media (FIG. 15A, fifth and sixth rows). The pde2/pde2 mutant was hyperfilamentous in both liquid YNB and YPD, however, true hypha were not seen in YNB. In liquid YPD, but not YNB, filamentous cells were more frequent in the heterozygous PDE2/pde2 mutant and in the revertant (about 20 to 30%) as compared to the wild type strain (less than 5%)(FIG. 15A, see e2 and e5).

To determine if the hypha-specific protein, Hwp1, which functions in stabilized adhesion to host tissue was present on the filamentous forms of the pde2/pde2 mutant; an IFA was performed using antibody specific for Hwp1 (Staab et al., supra (1996); and Staab et al., supra (1999)). Hwp1 positive hyphae of the homozygous pde2/pde2 mutant were frequently observed on YPD plates and liquid media, although production of Hwp1 positive hyphae was favored on solid media. In YNB media, filamentous forms of the pde2/pde2 mutant were Hwp1 negative and appeared pseudohyphal (FIG. 15B).

Germ tube production by the homozygous pde2/pde2 mutant was accelerated in conditions used to generate germ tubes in wild type strains (FIG. 16A). Short germ tubes were seen on greater than 90% of homozygous pde2/pde2 mutant cells after 1 hour of incubation, whereas only 50 to 60% of wild type strain had short germ tubes after 1.5 hours of incubation. By 1.5 hours, hyphae of pde2/pde2 mutant cells appeared comparable in length to those of wild type strains incubated for 5 hours.

The rapid extension of hyphae of the pde2/pde2 mutant in liquid media was also reflected in the presence of longer hyphae as compared to the other strains in solid media pour plates, conditions that generally promote hyphae formation (FIG. 16B). After 3 to 4 days of incubation in either Spider media or 4% serum media at 30° C., colony diameters of pde2/pde2 mutants were about 2.0-2.2 mm and about 1.5-1.7 mm in Spider and 4% serum media, respectively, as compared to about 1.0-1.2 mm and about 0.7-0.8 mm for UnoPP-1. Filaments of pde2/pde2 mutants were devoid of buds whereas a wild type PDE2 gene was correlated with the presence of buds on filaments in Spider media. In solid media containing serum, filaments of the PDE2/pde2 heterozygote appeared to lack buds. In SLAD media, filamentous growth of the pde2/pde2 mutant was also enhanced as compared to the wild type, the heterozygous PDE2/pde2, and revertant strains, however, levels of hyperfilamentation were not as pronounced as in Spider media and in 4% serum (data not shown).

The location of the URA3 gene did not affect the phenotypes of pde2/pde2 mutants described above (FIGS. 15A and 16B). Heterozygous PDE2/pde2 mutants having the URA3 gene targeted to ENO1 (BPS13, data not shown) showed the same morphological characteristics (i.e. mild filamentation and aggregation) in YPD media as those of revertant (BPS9) (FIG. 15A, see b5 and e5) and the heterozygous PDE2/pde2 mutants (BPS1) (FIG. 15A, see 15A b2 and e2) with URA3 located at the PDE2 locus. These results and those of the previous sections show that PDE2 represses filamentous growth of C. albicans.

Example 28

Figure 17:
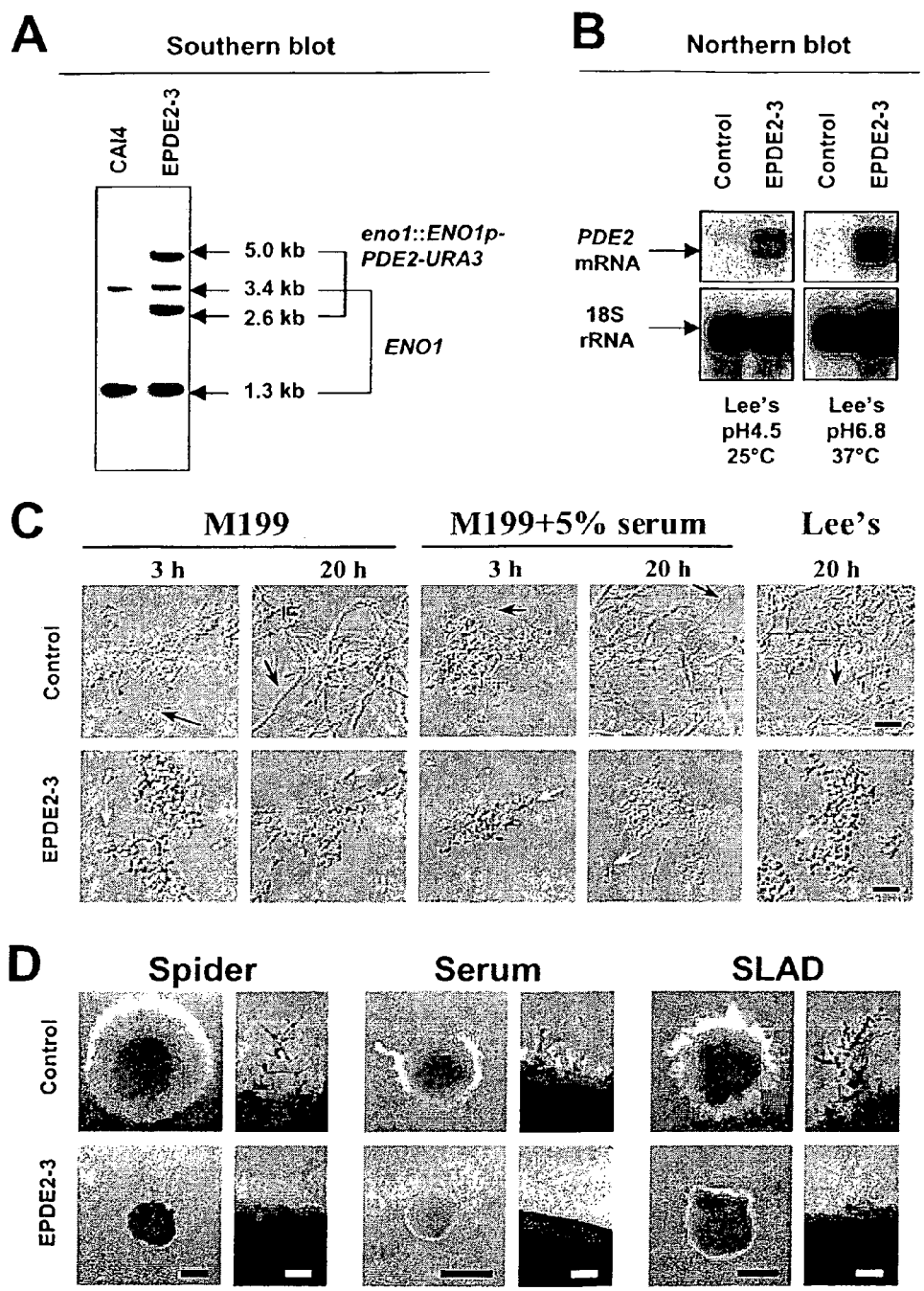
FIGS. 17A-17D show the inhibition of bud-hypha transitions by overexpression of PDE2.

Constitutive Overexpression of PDE2 Blocked Bud-hypha Transitions and Filamentous Growth of C. albicans If hyperfilamentation results from the inability to degrade cAMP in the pde2/pde2 mutant, then overexpression of PDE2 should decrease filamentation. As expected, placing the PDE2 gene under the control of the ENO1 promoter led to increased levels of PDE2 mRNA as compared to the endogenous PDE2 gene given that ENO1 is a highly expressed gene (Postlethwait and Sundstrom, supra)(FIG. 17B). 1-kb of the 5' UTR of ENO1 is sufficient for abundant expression of a GFP reporter protein in both yeast and hyphal morphologies using an integrative plasmid. Therefore, placement of PDE2 under the control of the ENO1 promoter allows the effect of increased and constitutive expression of PDE2 on cell morphology to be assessed. The PDE2 overexpression plasmid (pENO1PDE2-3) was targeted to the ENO1 locus of CAI4 as described above (FIG. 17A). Strains with pENO1PDE2-3 had PDE2 mRNA levels that were 10 to 12-fold higher both in yeast (Lee's media (pH4.5) at 25° C.) and hyphae (Lee's media (pH6.8) at 37° C.)(FIG. 17B). Results for only a single transformant are shown, however, three additional independent transformants gave identical results.

Overexpression of PDE2 (EPDE2-3, FIG. 12) led to defective bud-hypha transitions in liquid media and filamentous growth that was sustained upon prolonged incubation (FIG. 17C). Additionally, overexpression of PDE2 also led to defective filamentous growth in solid Spider, SLAD, and 4% serum media at 37° C. (FIG. 17D). The suppression of filamentous growth is correlated with overexpression of the PDE2 gene whereas enhanced filamentous growth of C. albicans is associated with disruption of the PDE2 gene. Indeed, the above results show that the PDE2 gene represses filamentous growth.

Example 29

Inactivation of the PDE2 Gene Suppresses Defects in Bud-hypha Transitions and Filamentous Growth of the cap1/cap1 Null Mutant Given the similarity of the PDE2 gene product to phosphodiesterases, it is likely that the PDE2 gene represses bud-hypha transitions and filamentous growth by degrading cAMP. Further support for this mechanism of regulation was obtained by analysis of cap/cap pde2/pde2 double mutants. cap1/cap1 null mutants produce basal levels of cAMP, however pulses of cAMP are not generated and bud-hypha transitions are defective. If PDE2 regulates filamentous growth by degrading cAMP, deletion of PDE2 in the cap1/cap1 null mutant background should accumulate cAMP in the cap1/cap1 pde2/pde2 double mutant, thereby correcting the bud-hypha transition defect generated by inactivation of the CAP1 gene.

The cap1/cap1 pde2/pde2 mutant (BPS 18) was equivalent to wild type in the kinetics and frequency of bud-hypha transitions in liquid media (FIG. 18A, see a1 to a10), and in the production of the hypha-specific protein Hwp1 (data not shown). Both the cap1/cap1 (CAC1-1A) and the cap1/cap1 PDE2/pde2 (BPS17) mutant were defective in bud-hypha transitions even after inducing germ tubes for 20 hours. Adding back a wild-type PDE2 gene to the cap1/cap1 pde2/pde2 mutant caused reversion back to defective bud-hypha transitions, confirming that PDE2 controlled bud-hypha transitions in cap1/cap1 cells.

Figure 18:
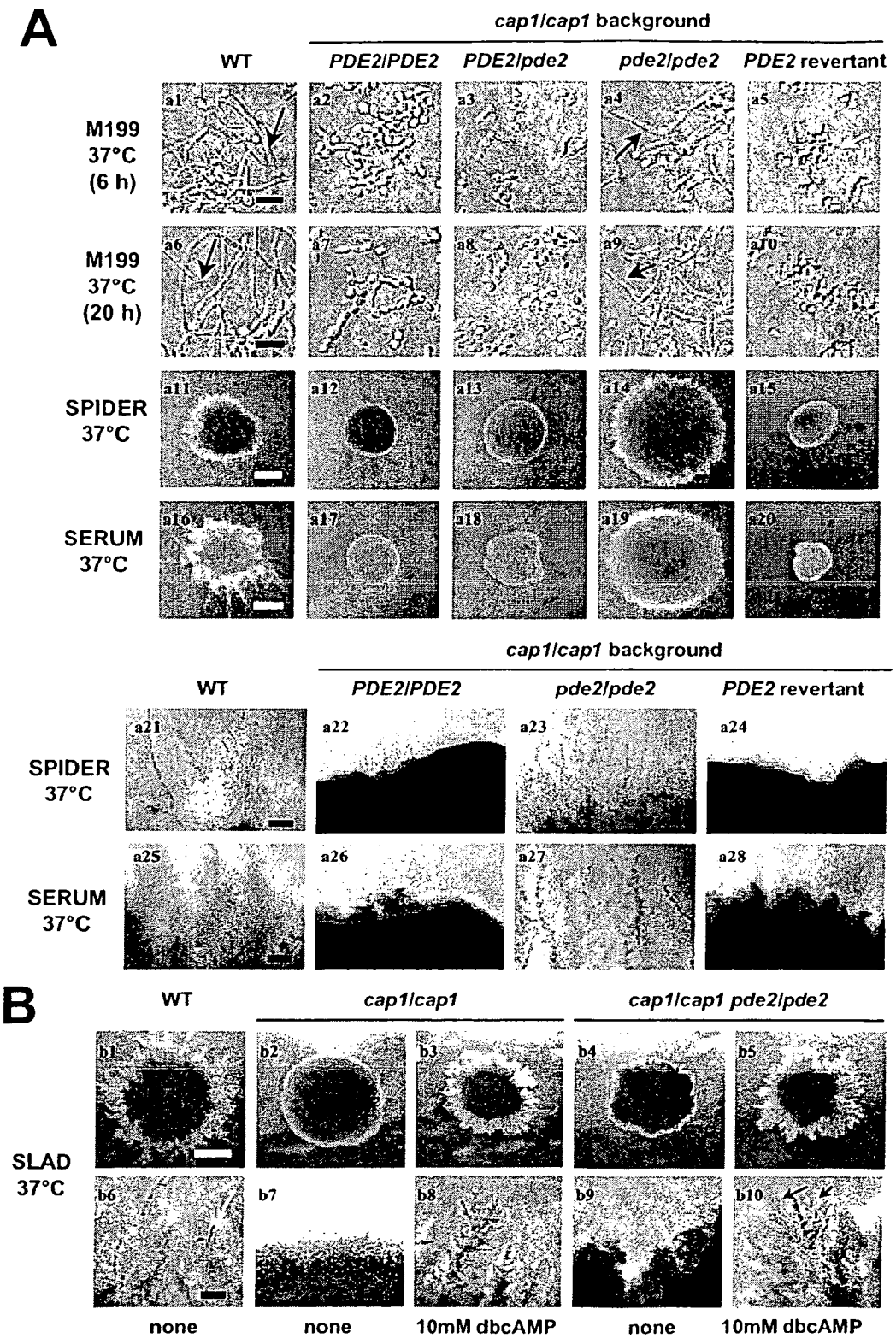
FIGS. 18A-18B show the restoration of normal bud-hypha transitions and filamentous growth to cap1/cap1 mutants by disruption of PDE2.

The cap1/cap1 pde2/pde2 double mutant appeared hyperfilamentous compared to the wild type strain in both Spider (FIG. 18A, see a11-15 and a21-24) and 4% serum media (FIG. 18A, see a16-20 and a25-28). In SLAD media, the restoration of filamentation was less pronounced (FIG. 18B, compare b4 to b2 and b9 to b7). Filamentation of the cap1/cap1 pde2/pde2 mutant was less than that of the wild type strain (FIG. 18B, compare b4 to b1 and b9 to b6). Colony edges of the cap1/cap1 pde2/pde2 mutant were more irregular than those of the cap1/cap1 mutant indicative of increased filamentation (FIG. 18B, compare b9 to b7), however, the filaments were masked by florid budding. The relative increase in the amount of budding of the double mutant on SLAD media shows that basal levels of cAMP in the cap1/cap1 mutant are reduced on SLAD as compared to the other media and that certain factors act together with CAP1 in the wild type strain to achieve cAMP levels consistent with wild type levels of filamentation. Whereas elimination of phosphodiesterase activity by deleting PDE2 was not sufficient for restoring cAMP levels supportive of filamentation in SLAD media, the addition of exogenous dibutyryl cAMP (dbcAMP) did increase filamentation of the cap1/cap1 pde2/pde2 mutant to near wild type levels. This result is consistent with a direct relationship between cAMP levels and filamentation (FIG. 18B). In the presence of external dbcAMP, however, more buds were seen on filaments of the cap1/cap1 pde2/pde2 mutant than on the wild type strain (FIG. 18B, compare b10 to b6), indicating that addition of exogenous cAMP may not restore wild-type levels of cAMP inside the cell.

It has been demonstrated that expression of HWP1 was reduced in the cap1/cap1 mutant, which is coincident with the block in germ tube formation. Recovery of bud-hypha transition and filamentous growth by disruption of PDE2 genes in cap1/cap1 mutants was accompanied by normal levels of expression of HWP1. Expression of HWP1 was recovered in cap1/cap1 pde2/pde2 mutants to the level of wild type strain and pde2/pde2 mutants in M199 containing 5% serum (data not shown). Therefore, Pde2 negatively regulates the Cap1-mediated cAMP-signaling pathway, repressing bud-hypha transitions and filamentous growth by degrading cAMP.

Example 30

Hyperfilamentous pde2/pde2 Mutants Invade Agar

The in vitro agar invasion test was performed to assess the role of the cAMP-signaling pathway on adhesive properties of C. albicans cells. The pde2/pde2 mutant was invasive on both YPD and YNB agar plates whereas the wild type, cap1/cap1, and cap1/cap1 pde2/pde2 mutants were not (data not shown). The PDE2 complemented strain was weakly invasive consistent with a copy number effect of the PDE2 gene on invasion (data not shown). The lawn of pde2/pde2 cells that resisted removal in the invasion assay appeared denser on YPD plates than YNB plates, which correlates with the observation that pde2/pde2 mutants were more filamentous on YPD than on YNB plates. This was further supported by the cellular morphology of cells that resisted washing. Cells washed off from YPD plates appeared to be a mixed population of yeast and filamentous forms, but the cells that resisted washing were predominantly filamentous. Cells that were not removed from YNB plates by washing mostly consisted of elongated buds or pseudohyphal forms, although less filamentous than cells remaining in YPD plates after washing. Indeed, the data show that filamentous growth and invasiveness are related traits and both are controlled by the cAMP-signaling pathway.

Example 31

Figure 19:
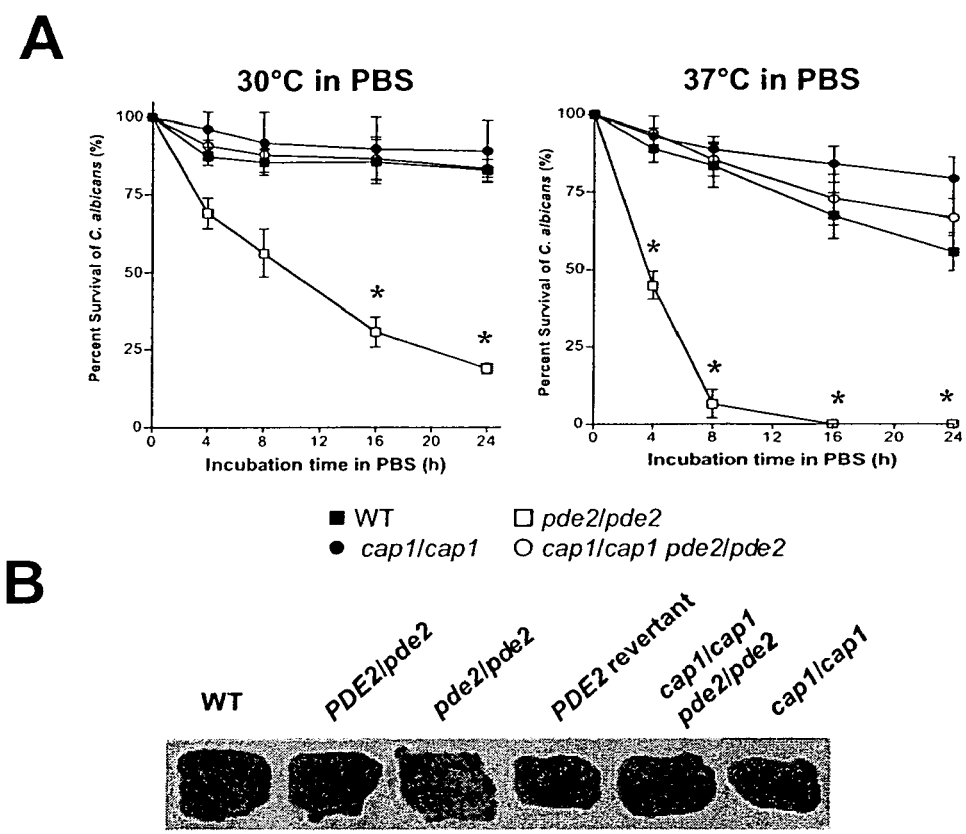
FIGS. 19A-19B illustrate the sensitivity of the C. albicans pde2/pde2 to nutrient deprivation and entry into stationary phase.

The pde2/pde2 Mutants are Sensitive to Nutrient Deprivation and Defective in Entry into Stationary Phase Hyperfilamentous growth, rapid bud-hypha transitions and increased expression of pro-adhesive Hwp1 of pde2/pde2 mutants are attributes that are correlated with virulence. Hyperactivation of cAMP signaling, however, is also associated with detrimental effects including increased sensitivity to nutrient deprivation and entry into stationary phase in *S. cerevisiae* (Broach, 1 GENET. DEV. 370-377 (1991); Harashima and Heitman, supra; and Toda et al., supra). The *C. albicans* pde2/pde2 mutant was more susceptible to nutritional starvation than the other strains. The most dramatic differences in viability were observed at 37° C. (FIG. 19A). More than 50% of pde2/pde2 mutants were killed after 4 hours in PBS at 37° C., whereas about 90% of other strains survived. Differences at 30° C. were also significant.

The *C. albicans* pde2/pde2 mutants were also defective in entry into stationary phase as assessed by iodine/iodide staining to measure levels of glycogen as previously described. Toda et al., supra. Whereas wild type and PDE2/pde2 strains grown for 2 days at 30° C. on YPD media were stained brown by aqueous iodine/iodide solution, pde2/pde2 mutants were yellow, showing reduced glycogen accumulation (FIG. 19B). Glycogen accumulation was recovered in the PDE2 revertant and cap1/cap1 pde2/pde2 mutant. In contrast, cap1/cap1 mutants produced more glycogen than wild type strains based on the dark brown color of patched cells (FIG. 19B). In conclusion, the data demonstrate that sensitivity to nutrient starvation and entry into stationary phase are controlled by the cAMP-signaling pathway in *C. albicans*.

Example 32

Figure 20:
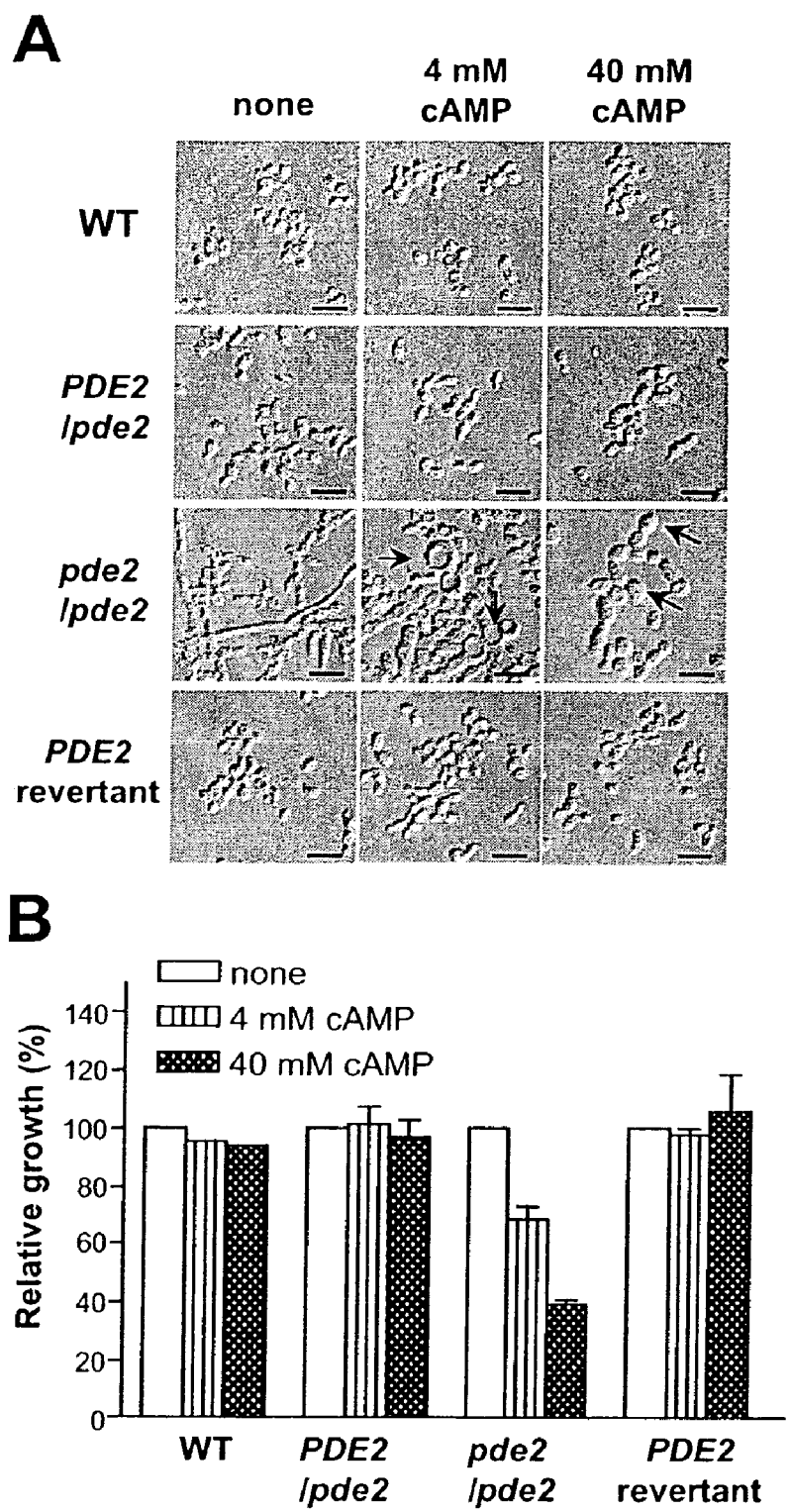
FIGS. 20A-B illustrates the effect of exogenous cAMP on morphology and growth rate.

Aberrant Morphology and Reduced Growth Rate of *C. albicans* pde2/pde2 Mutant in the Presence of Exogenous cAMP The *C. albicans* pde2/pde2 mutant was hypersensitive to the presence of about 4 or 40 mM exogenous cAMP, as shown by reduction in growth rates and viabilities, and by the presence of swollen cells. These phenotypes were not observed in the wild type, heterozygous PDE2/pde2 mutant, and PDE2 revertant strains in the presence of cAMP (FIG. 20). More swollen pde2/pde2 mutant cells (greater than 90% of cells) in the presence of 40 mM cAMP were observed than in 4 mM cAMP (~50% of cells)(FIG. 20A). The doubling time of pde2/pde2 mutants was 3.7 hours in YNB with 4 mM cAMP and 4.8 hours in YNB with 40 mM cAMP as compared to 2.6 hours in the absence of cAMP. Doubling times of strains with a wild type PDE2 gene were 2.5 to 2.6 hours for the wild type, heterozygous pde2/PDE2 mutant, and PDE2 revertant strains in YNB with or without the presence of cAMP. The sensitivity of the pde2/pde2 mutant to cAMP was also shown by the reduced number of CFUs following incubation in YNB containing 4 mM and 40 mM cAMP (about 70% and 40% of growth, respectively, in YNB alone)(FIG. 20B). In sum, these results show that *C. albicans* PDE2 is essential for maintaining an appropriate level of intracellular cAMP for normal growth and cellular morphology.

Example 33

Transcriptional Regulation of PDE2 During Bud-hypha Transitions

The toxicity of cAMP suggest that elevation of cAMP levels for signaling must be transient and tightly regulated. One possible mechanism for controlling cAMP may be direct activation of the PDE2 gene by cAMP itself. To test this idea, PDE2 expression was monitored in both wild type (SC5314) and cap1/cap1 strains by Northern blot analysis. During budding growth of the wild type strain in YNB at 30° C., PDE2 expression was low overall and decreased from early logarithmic phase to stationary phase (FIG. 21A). Surprisingly, PDE2 expression was rapidly induced, showing a 8-fold increase in less than 10 minutes of placement of yeasts in germ tube-inducing conditions. The 10-fold increase in PDE2 message peaked at 20 minutes, thereby preceding the peak of intracellular cAMP at 1 hour. Bahn and Sundstrom, supra. The message decreased over the next 3 hours (FIG. 21). HWP1 expression was detectable at 20 to 30 minutes after induction, and was subsequently maintained at high levels (FIG. 21).

The data are consistent with the hypothesis that PDE2 expression is activated by intracellular cAMP. The rapid induction of PDE2 message was absent in the cap1/cap1 mutant during germ tube induction conditions. PDE2 expression levels were comparable to those found in stationary phase cells and increased gradually, reaching only a 3-fold increase over the 3-hour period. This pattern is similar to the modest change in cAMP levels in the cap1/cap1 mutant during germ tube induction. Bahn and Sundstrom, supra. HWP1 mRNA levels were delayed and reduced in the cap1/cap1 mutant as compared to the wild type strain (FIG. 21A). To gain evidence for the dependence of induction of PDE2 during bud-hypha transitions on cAMP, cAMP (10 mM) was added to cultures of the cap1/cap1 mutant followed by Northern blot analysis. PDE2 mRNA expression was the same with or without exogenous cAMP (data not shown).

It may be likely that exogenous cAMP is not efficiently taken up into the cells or may not be present in high enough quantities or with the proper kinetics to induce PDE2 expression in the cap1/cap1 mutant. Nevertheless, the results strongly suggest that expression of PDE2 Is induced by cAMP during bud-hypha transitions.

Example 34

The pde2/pde2 Mutant is Avirulent in a Murine Model of Systemic Candidiasis

Figure 22:
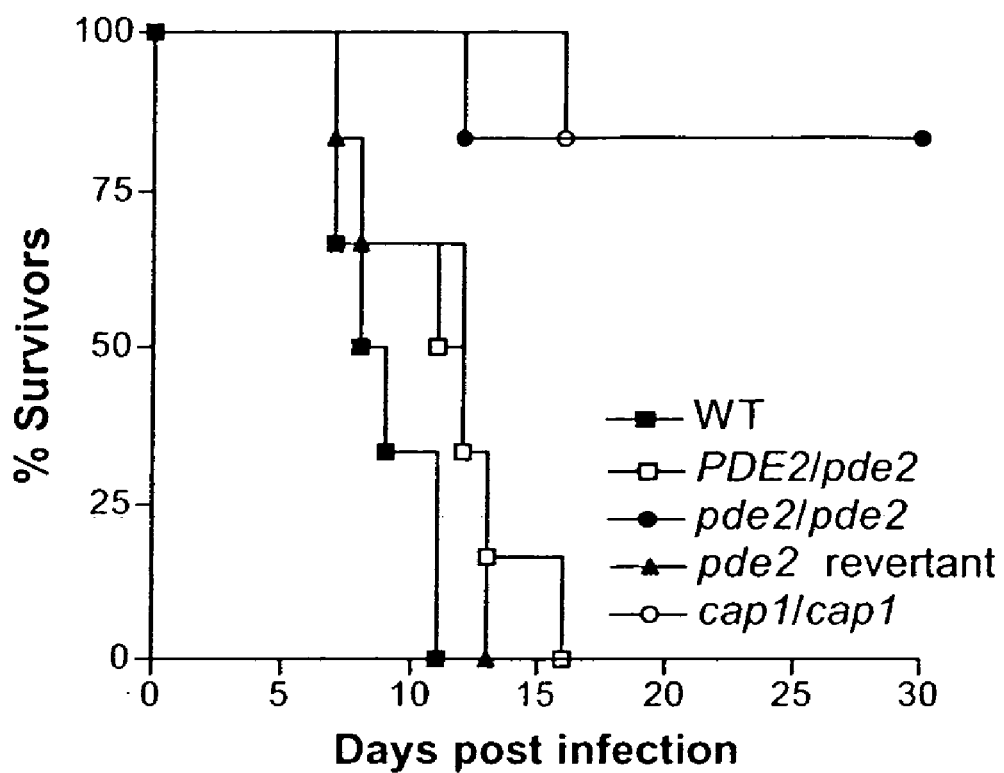
FIG. 22 depicts the avirulence of the pde2/pde2 mutant in a murine model of systemic candidiasis. Survival curves of mice (BALB/c, 5 to 6 weeks old, six mice per group) injected with $5 \times 10^6$ cells of isogenic C. albicans strains UnoPP-1 (WT, ■), BPS13 (DE2/pde2, □), BPS9 (PDE2 revertant, ▲), BPS15 (pde2/pde2, ●), and CAC1-1A1E1 (cap1/cap1, ○). Survival curves were illustrated according to the Kaplan-Meier method using the PRISM program and compared using the log-rank test. A P value of <0.01 was considered significant. Note that virulence of the cap1/cap1 and pde2/pde2 strains are significantly reduced compared to the wild type, heterozygous PDE2/pde2, and PDE2 revertant strains (P<0.01). Heterozygous PDE2/pde2 are as virulent as the wild type strain (P=0.1039) and PDE2 revertant strains (P=0.8656).

The murine model of systemic candidiasis was used to assess the virulence of the hyperfilamentous pde2/pde2 mutant and to compare the virulence of this mutant to the hypofilamentous cap1/cap1 mutant. Since the genetic location of URA3 gene in mutant strains may affect interpretation of virulence studies in the murine model of systemic candidiasis (Staab and Sundstrom, TRENDS MICROBIAL (2003, in press); Sundstrom et al., 2002b, supra), all strains used in this study have URA3 gene integrated into an allele of ENO1 (FIG. 12). Strains were grown in YNB prior to injection so that the pde2/pde2 mutant, as well as the other strains, would grow as yeasts permitting accurate determination of cell concentrations. UnoPP-1 was used as the wild type control strain and CAC1-1A1E1 (cap1/cap1) as the avirulent control strain (Bahn and Sundstrom, supra). Mice (BALB/c) injected with the wild type strain expired within 11 days after injection (FIG. 22). The heterozygous PDE2/pde2 strains (BPS13) were as virulent as the wild type strain and PDE2 revertant (BPS9)(FIG. 22). In contrast, greater than 80% of the mice given the cap1/cap1 mutant (CAC1-1A1E1) or pde2/pde2 mutant (BPS15) survived through the entire period of observation (30 days). Only one mouse out of six mice injected with the cap1/cap1 or pde2/pde2 mutant became ill and had to be sacrificed at day 16 and 12, respectively (FIG. 22). The survival of mice injected with pde2/pde2 mutants was significantly greater than that of mice given strains having at least one PDE2 gene (UnoPP-1 versus BPS15, P=0.0007, BPS13 versus BPS15, P-0.0036, BPS9 versus BPS15 P=0.0056).

The survival of mice injected with cap1/cap1 mutants was significantly greater than that of the wild type control strain (UnoPP-1 versus CAC1-1A1E1, P=0.0007), which is consistent with previous results (Bahn and Sundstrom, supra). No statistical difference in survival between pde2/pde2 mutants and cap1/cap1 mutants (BPS15 versus CAC1-1A1E1, P=0.9486) were found. C. albicans strains were recovered from sacrificed mice. CFU per gram kidney isolated from mice injected with UnoPP-1, BPS13, or BPS9 was approximately 105 to 106. Of the 6 mice injected with the pde2/pde2 mutant, three had infected kidneys (106 CFU per gram kidney from ill mouse sacrificed at day 12 and 105 to 107 CFU per gram kidney from healthy mice terminated at 30 days) and three cleared the infection. Two of the 6 mice injected with the cap1/cap1 mutant cleared infection, which is consistent with previous results (Bahn and Sundstrom, supra). Histological analysis of kidney tissue showed the presence of fungal balls composed mostly of hyphae in renal calices surrounded by numerous polymorphonuclear leukocytes in mice injected with C. albicans with mutations in PDE2 or CAP1 (data not shown). Phenotypic and genotypic analysis was performed to confirm the authenticity of the strains (data not shown). Yeasts recovered from the kidneys of mice injected with the cap1/cap1 mutant or the pde2/pde2 mutant showed nonfilamentous or hyperfilamentous growth, respectively, in vitro.

The disclosures of all references and publications cited above are expressly incorporated by reference in their entireties to the same extent as if each were incorporated by reference individually.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in molecular biology or related fields, are intended to be within the scope of the following claims.

What is claimed is:

1. A method for altering the virulence properties of *C. albicans* comprising contacting *C. albicans* with a *C. albicans* PDE2 gene or PDE2 binding partner thereby altering the expression of the *C. albicans* PDE2 gene encoding a protein comprising the amino acid sequence of SEQ ID NO:3, wherein said altered expression affects the virulence properties of *C. albicans*.

2. The method of claim 1, wherein said inhibiting expression of PDE2 gene results in one or more of the group consisting of enhanced activation of the cAMP-PKA signaling pathway, hyperactive germ tube formation, avirulence, attenuated arvirulence, hyperproduction of HWP1, sensitivity to nutrient starvation, defective entry into stationary phase, and increased sensitivity to exogenous cAMP.

3. The method of claim 1, wherein said inhibiting expression of PDE2 gene comprises interfering with PDE2 gene transcription mediated by cis acting sequences.

4. The method of claim 3, wherein said cis-acting sequences comprise cis-regulatory elements.

5. The method of claim 4, wherein said cis-regulatory elements comprise UAS.

6. The method of claim 4, wherein said cis-regulatory elements comprise URS.

7. The method of claim 4, wherein said cis-regulatory elements comprise a cAMP response element (CRE).

8. The method of claim 3, wherein said interfering with PDE2 gene transcription comprises interfering with DNA binding proteins (BP) that bind to PDE2 cis-regulatory elements.

9. The method of claim 8, wherein said DNA BP comprises the CRE binding protein.

10. The method of claim 1, wherein said PDE2 gene overexpression results in one or more of the group consisting of defects in germ tube formation, inhibition of bud-hypha transitions, reduced filamentous growth, and a down-regulation of the cAMP-PKA signaling pathway.

11. The method of claim 1, wherein said virulence properties comprise adhesive properties.

12. The method of claim 11, wherein said adhesive properties comprise ability of *C. albicans* to adhere to one or more human tissues.

13. The method of claim 12, wherein said human tissues are one or more human tissues selected from the group consisting of vaginal, penile, oral, esophageal, gastrointestinal, and umbilical tissues.

14. The method of claim 1, wherein said virulence properties comprise invasive properties.

15. The method of claim 14, wherein said invasive properties comprise abilities of *C. albicans* to degrade extracellular matrix proteins.

16. The method of claim 14, wherein said invasive properties comprise abilities of *C. albicans* to block neutrophil oxygen radical production and degranulation.

17. The method of claim 1, wherein said virulence properties comprise proliferative properties.

18. The method of claim 1, wherein said *C. albicans* has infected a patient.

19. The method of claim 18, wherein said patient suffers from a disease.

20. The method of claim 19, wherein said disease is human immunodeficiency virus.

21. The method of claim 19, wherein said disease comprises complications associated with acquired immune deficiency syndrome.

22. The method of claim 19, wherein said disease comprises complications associated with an acquired immune deficiency syndrome related complex.

23. The method of claim 19, wherein said disease comprises one or more diseases selected from the group consisting of HIV, mucosal candidiasis, oral candidiasis, esophageal candidiasis, thrush, hemoatogenously disseminated candidiasis, and candida vaginitis.

24. The method of claim 18, wherein said patient is immunocompromised.

25. The method of claim 18, wherein said patient is an organ transplant recipient.

26. The method of claim 18, wherein said patient is undergoing a treatment regimen.

27. The method of claim 26, wherein said treatment regimen is chemotherapy.

28. The method of claim 26, wherein said treatment regimen is a drug regimen.

29. The method of claim 28, wherein said drug regimen suppresses the immune system.

30. The method of claim 28, wherein said drug regimen incorporates the use of one or more drugs that are selected from the group consisting of azathioprine, steroids, cyclosporine, antilymphocyte globulins, monoclonal anti-T cell antibodies, prednisone, methylprednisone, and cyclophosphamide.

* * * * *

UNITED STATES PATENT AND TRADEMARK OFFICE
CERTIFICATE OF CORRECTION

PATENT NO. : 7,270,975 B2
APPLICATION NO. : 10/672074
DATED : September 18, 2007
INVENTOR(S) : Paula Sundstrom It is certified that error appears in the above-identified patent and that said Letters Patent is hereby corrected as shown below:

At column 1, line 18: Please delete "numbers 2R01DE011375 and" and insert --number--.

At column 11, line 65: Please delete "(cap1/cap1,)" and insert --(cap1/cap1,•)-- .

At column 30, line 21: Please delete "demonstrate" and insert --demonstrated--.

At column 40, line 34: Please delete "4314" and insert --431-4--.

At column 40, line 60: Please delete "Feignere" and insert --Felgner--.

At column 50, line 46: Please delete "$MnC_2$" and insert --$MnCl_2$--.

At column 51, line 2: Please delete "filamenious" and insert --filamentous--.

At column 52, line 43: Please delete "27°" and insert --27°C--.

At column 56, line 58: Please delete "(M1 99+serum)" and insert --(M199+serum)--.

At column 57, line 58: Please delete "Immun. 42804" and insert --Immun. 4280-4--.

At column 57, line 60: Please delete "43545" and insert --435-45--.

At column 61, line 21: Please delete "PDE2 ene" and insert --PDE2 gene--.

Signed and Sealed this

Twenty-second Day of June, 2010

David J. Kappos
*Director of the United States Patent and Trademark Office*

CERTIFICATE OF CORRECTION (continued)
U.S. Pat. No. 7,270,975 B2

At column 89, line 64: Please delete Claim 1 in its entirety and insert --A method for altering the virulence properties of *C. albicans* comprising inhibiting the expression or over expressing *C. albicans* *PDE2* gene encoding a protein comprising the amino acid sequence of SEQ ID NO:3, wherein said inhibition or over expression affects the virulence properties of *C. albicans*.--

At column 91, line 12: Please delete "UAS" and insert --upstream activating sequence (UAS)--.

At column 91, line 14: Please delete "URS" and insert --upstream regulatory sequence (URS)--.

SEQUENCE LISTING

<160> NUMBER OF SEQ ID NOS: 15

<210> SEQ ID NO 1
<211> LENGTH: 545
<212> TYPE: PRT
<213> ORGANISM: Candida albicans

<400> SEQUENCE: 1

```
Met Ser Thr Glu Glu Ser Gln Phe Asn Val Gln Gly Tyr Asn Ile Ile
1               5                   10                  15

Thr Ile Leu Lys Arg Leu Glu Ala Ala Thr Ser Arg Leu Glu Asp Ile
            20                  25                  30

Thr Ile Phe Gln Glu Glu Ala Asn Lys Asn His Tyr Gly Val Asp Ser
        35                  40                  45

Leu Thr Glu Lys Gly Thr Pro Lys Ser Arg Thr Val Glu Ser Ser Glu
    50                  55                  60

Ala Thr Ser Asp Gly Lys Ser Leu Glu Ser Thr Ser Phe Ala Thr Phe
65                  70                  75                  80

Ser Glu Ala Pro Val Glu Lys Ser Lys Leu Ile Val Glu Phe Glu Asn
                85                  90                  95

Phe Val Glu Ser Tyr Val His Pro Leu Val Glu Thr Ser Lys Lys Ile
            100                 105                 110

Asp Ser Leu Val Gly Glu Ser Ala Gln Tyr Phe Tyr Glu Ala Phe Val
        115                 120                 125

Glu Gln Gly Lys Phe Leu Glu Leu Val Leu Gln Ser Gln Gln Pro Asp
    130                 135                 140
```

-continued

```
Met Thr Asp Pro Ala Leu Ala Lys Ala Leu Glu Pro Met Asn Ala Lys
145                 150                 155                 160

Cys Thr Lys Ile Asn Glu Leu Lys Asp Ser Asn Arg Lys Ser Pro Phe
                165                 170                 175

Phe Asn His Leu Ser Thr Phe Ser Glu Ser Asn Ala Val Phe Tyr Trp
            180                 185                 190

Ile Gly Ile Pro Thr Pro Val Ser Tyr Ile Thr Asp Thr Lys Asp Thr
        195                 200                 205

Val Lys Phe Trp Ser Asp Arg Val Leu Lys Glu Tyr Lys Thr Lys Asp
    210                 215                 220

Gln Val His Val Glu Trp Val Lys Gln Thr Leu Ser Val Phe Asp Glu
225                 230                 235                 240

Leu Lys Asn Tyr Val Lys Glu Tyr His Thr Thr Gly Val Ala Trp Asn
                245                 250                 255

Pro Lys Gly Lys Pro Phe Ala Glu Val Val Ser Gln Gln Thr Glu Ser
            260                 265                 270

Ala Ala Lys Asn Ser Ser Ala Ser Gly Ser Ala Gly Gly Ala Ala
        275                 280                 285

Pro Pro Pro Pro Pro Pro Pro Ala Thr Phe Phe Asp Asp Thr
290                 295                 300

Glu Lys Asp Ser Glu Asn Pro Ser Pro Ala Ser Gly Gly Ile Asn Ala
305                 310                 315                 320

Val Phe Ala Glu Leu Asn Gln Gly Ala Asn Ile Thr Ser Gly Leu Lys
                325                 330                 335

Lys Val Asp Lys Ser Glu Met Thr His Lys Asn Pro Glu Leu Arg Lys
            340                 345                 350

Gln Pro Pro Val Ala Pro Lys Lys Pro Ala Pro Pro Lys Lys Pro Ser
        355                 360                 365

Ser Leu Ser Gly Gly Val Ser Ser Ala Pro Val Lys Lys Pro Ala Lys
    370                 375                 380

Lys Glu Leu Ile Asp Gly Thr Lys Trp Ile Ile Gln Asn Phe Thr Lys
385                 390                 395                 400

Ala Asp Ile Ser Asp Leu Ser Pro Ile Thr Ile Glu Val Glu Met His
                405                 410                 415

Gln Ser Val Phe Ile Gly Asn Cys Ser Asp Val Thr Ile Gln Leu Lys
            420                 425                 430

Gly Lys Ala Asn Ala Val Ser Val Ser Glu Thr Lys Asn Val Ala Leu
        435                 440                 445

Val Ile Asp Ser Leu Ile Ser Gly Val Asp Val Ile Lys Ser Tyr Lys
    450                 455                 460

Phe Gly Ile Gln Val Leu Gly Leu Val Pro Met Leu Ser Ile Asp Lys
465                 470                 475                 480

Ser Asp Glu Gly Thr Ile Tyr Leu Ser Gln Glu Ser Ile Asp Asn Asp
                485                 490                 495

Ser Gln Val Phe Thr Ser Ser Thr Ala Leu Asn Ile Asn Ala Pro
            500                 505                 510

Lys Glu Asn Asp Asp Tyr Glu Glu Leu Ala Val Pro Glu Gln Phe Val
        515                 520                 525

Ser Lys Val Val Asn Gly Lys Leu Val Thr Gln Ile Val Glu His Ala
    530                 535                 540

Gly
545
```

-continued

<210> SEQ ID NO 2
<211> LENGTH: 1634
<212> TYPE: DNA
<213> ORGANISM: Candida albicans

<400> SEQUENCE: 2

| | | | |
|---|---|---|---|
| atgtcaaccg aggagagtca attcaatgtt caaggttaca atattatcac aatcttgaaa | 60 |
| agattagagg cagcaacgtc tcgtcttgag gacattacca ttttccaaga ggaagcaaac | 120 |
| aaaaaccaca tggagttgat tctctcactg aaagggaac ccccaaaagc agaactgttg | 180 |
| aatcgtcaga agcaacttcc gatggtaaat cactcgaatc tacatcattt gccacttttt | 240 |
| ctgaagctcc tgtagaaaaa tccaaattga ttgtggaatt tgagaacttt gttgaaagct | 300 |
| acgttcatcc acttgttgaa acatccaaaa agatcgattc cttggtgggg gagtccgccc | 360 |
| aatatttta tgaggcattt gtcgaacaag ggaattttt ggagcttgta ttgcaatccc | 420 |
| aacaaccaga tatgactgat ccagctttgg caaaggcatt agaaccaatg aatgctaaat | 480 |
| gcaccaaaat taacgaatta aaaattccaa tcgtaaatct ccattcttca atcatttaag | 540 |
| cactttcagt gaaagtaatg ccgttttta ttggattggg atccctacac cagtctcgta | 600 |
| cattactgat actaaagata cagtcaaatt ttggtctgac agagttttaa agaatacaa | 660 |
| gaccaaagac caagtgcatg ttgaatgggt aaaacaaaca ttatctgttt ttgacgaatt | 720 |
| gaagaattat gttaaagaat atcacacaac tggtgttgct tggaacccca aggaaagcc | 780 |
| ttttgcagaa gttgtatctc agcaaacaga gagtgctgct aagaattctt cgtctgcttc | 840 |
| tggttctgca ggaggagcag ctccaccacc acctccacct ccacctccag caacgttttt | 900 |
| tgatgacact gaaaaagaca gtgaaaaatcc atctcagctt caggtggtat taatgcggtt | 960 |
| ttgctgaatt gaatcaaggt gccaacatca catctggttt aaaaaaagtc gacaaatctg | 1020 |
| agatgacgca taagaaccct gaattaagaa acagccacc agttgcacca aaaaaaccag | 1080 |
| caccccaaa gaagccatct agtttatccg gtggtgtgag ttcagctcca gtaaagaagc | 1140 |
| ctgctaagaa ggagttgatt gacggtacaa atggataat tcaaaatttt acaaaagctg | 1200 |
| atatttccga tttgagtcca attaccattg aagttgagat gcatcaatct gttttcattg | 1260 |
| gtaattgtag tgatgtcacc attcagttga aggtaaagc aaatgcagtg tcggtatcgg | 1320 |
| aaaccaagaa tgtggctctt gtcattgatt cgttgatttc cggagtcgat gttattaaat | 1380 |
| cctacaagtt tggtatacaa gttttaggtt tggtaccaat gttgagtatt gataaatcag | 1440 |
| atgaagggac tatctatttg tcgcaagaaa gcattgacaa tgatagtcag gttttactac | 1500 |
| gtagcactac agcactcaac atcaatgcac caaggaaaa tgatgattat gaagaattgg | 1560 |
| ctgttcctga acaattgtt agtaaggttg tgaatggcaa attagtcact caaattgttg | 1620 |
| aacatgctgg ataa | 1634 |

<210> SEQ ID NO 3
<211> LENGTH: 150
<212> TYPE: PRT
<213> ORGANISM: Candida albicans

<400> SEQUENCE: 3

Asn Pro Ile Gln Thr Leu Gly Leu Leu Val Ala Ala Leu Gly His Asp
1               5                   10                  15

Val Gly His Pro Gly Thr Thr Asn Asp Phe Met Ile Lys Phe Ser Ala
            20                  25                  30

Pro Thr Ala Leu Leu Tyr Asn Asp Arg Ser Val Leu Glu Ser Tyr His

```
                35                  40                  45
Ala Ser Leu Phe Ile Asn Lys Val Leu Arg Ile Cys Trp Pro Asp Leu
     50                  55                  60

Leu Thr Cys Thr Ile Glu Glu Lys Ser Glu Leu Thr Ile Arg Ser Leu
 65                  70                  75                  80

Ile Ile Ser Ser Ile Leu Ala Thr Asp Met Gly Glu His Asn Glu Tyr
                 85                  90                  95

Val Asn Arg Leu Lys Ser Phe Lys Thr His Asn Glu Ile Leu Asn His
            100                 105                 110

Asp Asn Thr Val Lys Leu Ile Ser Ala Leu Leu Ile Lys Cys Ala Asp
        115                 120                 125

Ile Ser Asn Val Thr Arg Pro Leu Arg Val Ser Ala Gln Trp Ala Met
    130                 135                 140

Val Leu Ser Arg Glu Phe
145                 150

<210> SEQ ID NO 4
<211> LENGTH: 135
<212> TYPE: PRT
<213> ORGANISM: Saccharomyces cerevisiae

<400> SEQUENCE: 4

Asn Pro Val Gln Thr Leu Leu Cys Met Ala Ala Ile Gly His Asp
 1               5                  10                  15

Val Gly His Pro Gly Thr Asn Asn Gln Leu Leu Cys Asn Cys Glu Ser
             20                  25                  30

Glu Val Ala Gln Asn Phe Lys Asn Val Ser Ile Leu Glu Asn Phe His
         35                  40                  45

Arg Glu Leu Phe Gln Gln Leu Leu Ser Glu His Trp Pro Leu Lys Leu
     50                  55                  60

Ser Ile Ser Lys Lys Phe Asp Phe Ile Ser Glu Ala Ile Leu Ala
 65                  70                  75                  80

Thr Asp Met Ala Leu His Ser Gln Tyr Glu Asp Arg Leu Met His Glu
                 85                  90                  95

Asn Pro Met Lys Gln Ile Thr Leu Ile Ser Leu Ile Ile Lys Ala Ala
            100                 105                 110

Asp Ile Ser Asn Val Thr Arg Thr Leu Ser Ile Ser Ala Arg Trp Ala
        115                 120                 125

Tyr Leu Ile Thr Leu Glu Phe
    130                 135

<210> SEQ ID NO 5
<211> LENGTH: 149
<212> TYPE: PRT
<213> ORGANISM: Homo sapiens

<400> SEQUENCE: 5

Glu Asp Ile Glu Ile Phe Ala Leu Phe Ile Ser Cys Met Cys His Asp
 1               5                  10                  15

Leu Asp His Arg Gly Thr Asn Asn Ser Phe Gln Val Ala Ser Lys Ser
             20                  25                  30

Val Leu Ala Ala Leu Tyr Ser Ser Glu Gly Ser Val Met Glu Arg His
         35                  40                  45

His Phe Ala Gln Ala Ile Ala Ile Leu Asn Thr His Gly Cys Asn Ile
     50                  55                  60

Phe Asp His Phe Ser Arg Lys Asp Tyr Gln Arg Met Leu Asp Leu Met
```

-continued

```
                65                  70                  75                  80
Arg Asp Ile Ile Leu Ala Thr Asp Leu Ala His His Leu Arg Ile Phe
                    85                  90                  95

Lys Asp Leu Gln Lys Met Ala Glu Val Gly Tyr Asp Arg Asn Asn Lys
                100                 105                 110

Gln His His Arg Leu Leu Leu Cys Leu Leu Met Thr Ser Cys Asp Leu
                115                 120                 125

Ser Asp Gln Thr Lys Gly Trp Lys Thr Thr Arg Lys Ile Ala Glu Leu
    130                 135                 140

Ile Tyr Lys Glu Phe
145

<210> SEQ ID NO 6
<211> LENGTH: 22
<212> TYPE: DNA
<213> ORGANISM: Candida albicans

<400> SEQUENCE: 6
gcaaataaat ccgtaggaaa cg                                            22

<210> SEQ ID NO 7
<211> LENGTH: 20
<212> TYPE: DNA
<213> ORGANISM: Candida albicans

<400> SEQUENCE: 7
ccaccaacac caacagaaaa                                               20

<210> SEQ ID NO 8
<211> LENGTH: 566
<212> TYPE: PRT
<213> ORGANISM: Candida albicans

<400> SEQUENCE: 8

Met Ala Glu Val Leu Ser Leu Val Asp Leu Glu Ile Pro Gln Val Thr
1               5                   10                  15

Asp Lys Tyr Tyr Lys Phe Asp Thr Phe Lys His Leu Ile Cys His Leu
                20                  25                  30

Phe Lys Lys Thr Ser Thr Glu Thr Asp Ser Asn Val Pro Ile Val Ile
                35                  40                  45

Ile Phe Pro Thr Asn Asp Ile Pro Ser Arg Lys Thr Arg Ser Thr
    50                  55                  60

Thr Thr Thr Thr Thr Thr Thr Thr Thr Asn Thr Ser Lys Leu Asp
65                  70                  75                  80

Asn Leu Pro Phe Ser Asp Lys Ser Leu Leu Ile Gln Phe Phe Thr
                85                  90                  95

His Leu Asn Ile Leu Met Ile Gln Gly Glu Asn Ser Asp Glu Gly Lys
                100                 105                 110

Leu Tyr Gln Glu Ile Ser Ser Ala Lys Glu Leu Leu Thr Asn Arg Ile
                115                 120                 125

Ser Arg Val Gly Asn Trp Gly Thr Thr His Phe Arg Tyr Cys Arg
    130                 135                 140

His Glu Asn Asp Cys Gly Leu Leu Asn Gln His Ser Lys Ile Ala Gly
145                 150                 155                 160

Ile Ile Pro Thr Met Thr Tyr Ile Leu Asn Cys Asn Ala Thr Arg Ser
                165                 170                 175

Glu Ile Ala Thr Asn Gln Leu Ile Tyr Leu Tyr Arg Leu Met Ile Glu
```

```
                    180                 185                 190
Glu Ile Asn Phe Ile Glu Leu Leu Gln Asp Ala Ser Thr Thr Arg Leu
            195                 200                 205

Ser Gln Leu Cys Tyr Ala Val Gly His Trp Ser Phe Pro Ala His Asn
210                 215                 220

Leu Ser Asn Asp Asp Leu Val Tyr Cys Val Tyr Leu Met Ile Asp Tyr
225                 230                 235                 240

Ala Ile Lys Gln Val Glu Gly Phe Asp Asn Ile Pro Leu Asn Glu Leu
                245                 250                 255

Leu Ala Phe Ile Phe Ile Val Arg Asp Thr Tyr Lys Asn Gly Asn Pro
            260                 265                 270

Phe His Asn Phe Arg His Ala Val Asp Val Leu Gln Ala Cys Phe His
        275                 280                 285

Phe Leu Ile Arg Leu Gly Ser Leu Pro Lys Phe Lys Gln Phe Val Glu
    290                 295                 300

Asp Pro Lys Leu Asp Tyr Thr Glu Val His Asp Thr His Thr Val Leu
305                 310                 315                 320

Ile Ala Leu Gln Asn Asn Ser Ser Glu Glu Lys Ala Ser Leu Asn Pro
                325                 330                 335

Ile Gln Thr Leu Gly Leu Leu Val Ala Ala Leu Gly His Asp Val Gly
            340                 345                 350

His Pro Gly Thr Thr Asn Asp Phe Met Ile Lys Phe Ser Ala Pro Thr
        355                 360                 365

Ala Leu Leu Tyr Asn Asp Arg Ser Val Leu Glu Ser Tyr His Ala Ser
    370                 375                 380

Leu Phe Ile Asn Lys Val Leu Arg Ile Cys Trp Pro Asp Leu Leu Thr
385                 390                 395                 400

Cys Thr Ile Glu Glu Lys Ser Glu Leu Thr Ile Arg Ser Leu Ile Ile
                405                 410                 415

Ser Ser Ile Leu Ala Thr Asp Met Gly Glu His Asn Glu Tyr Val Asn
            420                 425                 430

Arg Leu Lys Ser Phe Lys Thr His Asn Glu Ile Leu Asn His Asp Asn
        435                 440                 445

Thr Val Lys Leu Ile Ser Ala Leu Leu Ile Lys Cys Ala Asp Ile Ser
    450                 455                 460

Asn Val Thr Arg Pro Leu Arg Val Ser Ala Gln Trp Ala Met Val Leu
465                 470                 475                 480

Ser Arg Glu Phe Ala Glu Val Glu Leu Leu Lys Ser Val Ile Lys Lys
                485                 490                 495

Asp Ile Asp Leu Asp Phe Thr Lys Asp Leu Thr Tyr Asp Asp Val Pro
            500                 505                 510

His Glu Leu Arg Glu Ile Leu Glu Ile Gln Pro Asp Ile His Lys Gly
        515                 520                 525

Gln Ile Phe Phe Ile Asn Leu Phe Ala Glu Asn Leu Phe Asn Ser Val
    530                 535                 540

Ser Asp Leu Leu Pro Gln Leu Gln Tyr Thr Cys Asp Ile Ile Met Glu
545                 550                 555                 560

Asn Lys Leu Phe Trp Leu
                565

<210> SEQ ID NO 9
<211> LENGTH: 571
<212> TYPE: PRT
<213> ORGANISM: Candida albicans
```

<400> SEQUENCE: 9

```
Met Ala Glu Val Leu Ser Leu Val Asp Ser Glu Ile Pro Gln Val Thr
1               5                   10                  15

Asp Lys Tyr Tyr Lys Phe Asp Thr Phe Lys His Leu Ile Cys His Leu
            20                  25                  30

Phe Lys Lys Thr Ser Thr Glu Thr Asp Ser Asn Val Pro Ile Val Ile
        35                  40                  45

Ile Phe Pro Thr Asn Asn Asp Ile Pro Ser Arg Lys Thr Arg Ser Thr
    50                  55                  60

Thr Thr Thr Thr Thr Thr Ala Thr Thr Thr Asn Thr Ser Lys Leu Asp
65                  70                  75                  80

Asn Leu Pro Phe Ser Asp Lys Ser Leu Leu Ile Gln Phe Phe Phe Thr
                85                  90                  95

His Leu Asn Ile Leu Met Ile Gln Gly Glu Asn Ser Asp Glu Gly Lys
            100                 105                 110

Leu Tyr Gln Glu Ile Ser Ser Ala Lys Glu Leu Leu Thr Asn Arg Ile
        115                 120                 125

Ser Arg Val Gly Asn Trp Thr Gly Thr Thr His Phe Arg Tyr Cys Arg
    130                 135                 140

His Glu Asn Asp Cys Gly Leu Leu Asn Gln His Ser Lys Ile Ala Gly
145                 150                 155                 160

Ile Ile Pro Thr Met Thr Tyr Ile Leu Asn Cys Asn Ala Thr Arg Ser
                165                 170                 175

Glu Ile Ala Thr Asn Gln Leu Ile Tyr Leu Tyr Arg Leu Met Ile Glu
            180                 185                 190

Glu Ile Asn Phe Ile Glu Leu Leu Gln Asp Ala Ser Thr Thr Arg Leu
        195                 200                 205

Ser Gln Leu Cys Tyr Ala Val Gly His Trp Ser Phe Pro Ala His Asn
    210                 215                 220

Leu Ser Asn Asp Asp Leu Val Tyr Cys Val Tyr Leu Met Ile Asp Tyr
225                 230                 235                 240

Ala Ile Lys Gln Val Glu Gly Phe Asp Asn Ile Pro Leu Asn Glu Leu
                245                 250                 255

Leu Ala Phe Ile Phe Ile Val Arg Asp Thr Tyr Lys Asn Gly Asn Pro
            260                 265                 270

Phe His Asn Phe Arg His Ala Val Asp Val Leu Gln Ala Cys Phe His
        275                 280                 285

Phe Leu Ile Arg Leu Gly Ser Leu Pro Lys Phe Lys Gln Phe Val Glu
    290                 295                 300

Asp Pro Lys Leu Asp Tyr Thr Glu Val His Asp Lys His Thr Val Leu
305                 310                 315                 320

Ile Ala Leu Gln Asn Asn Ser Ser Glu Glu Lys Ala Ser Leu Asn Pro
                325                 330                 335

Ile Gln Thr Leu Gly Leu Leu Val Ala Ala Leu Gly His Asp Val Gly
            340                 345                 350

His Pro Gly Thr Thr Asn Asp Phe Met Ile Lys Phe Ser Ala Pro Thr
        355                 360                 365

Ala Leu Leu Tyr Asn Asp Arg Ser Val Leu Glu Ser Tyr His Ala Ser
    370                 375                 380

Leu Phe Ile Asn Lys Val Leu Arg Ile Cys Trp Pro Asp Leu Leu Thr
385                 390                 395                 400

Cys Thr Ile Glu Glu Lys Ser Glu Leu Thr Ile Arg Ser Leu Ile Ile
```

```
                405                 410                 415
Ser Ser Ile Leu Ala Thr Asp Met Gly Glu His Asn Glu Tyr Val Asn
            420                 425                 430

Arg Leu Lys Ser Phe Lys Thr His Asn Glu Ile Leu Asn His Asp Asn
        435                 440                 445

Thr Val Lys Leu Ile Ser Ala Leu Leu Ile Lys Cys Ala Asp Ile Ser
    450                 455                 460

Asn Val Thr Arg Pro Leu Arg Val Ser Ala Gln Trp Ala Met Val Leu
465                 470                 475                 480

Ser Arg Glu Phe Ala Glu Val Glu Leu Leu Lys Ser Val Ile Lys Lys
                485                 490                 495

Asp Ile Asp Leu Asp Phe Thr Lys Asp Leu Thr Tyr Asp His Val Pro
            500                 505                 510

His Glu Leu Arg Glu Ile Leu Glu Ile Gln Pro Asp Ile His Lys Gly
        515                 520                 525

Gln Ile Phe Phe Ile Asn Leu Phe Ala Glu Asn Leu Phe Asn Ser Val
    530                 535                 540

Ser Asp Leu Leu Pro Gln Leu Gln Tyr Thr Cys Asp Ile Ile Met Glu
545                 550                 555                 560

Asn Lys Leu Phe Trp Leu Glu Arg Ala Lys Lys
                565                 570

<210> SEQ ID NO 10
<211> LENGTH: 11
<212> TYPE: PRT
<213> ORGANISM: Candida albicans

<400> SEQUENCE: 10

Thr Thr Thr Thr Thr Thr Thr Ala Thr Thr Thr
1               5                   10

<210> SEQ ID NO 11
<211> LENGTH: 23
<212> TYPE: DNA
<213> ORGANISM: Candida albicans

<400> SEQUENCE: 11
gggatggcag aagtattatc att                                           23

<210> SEQ ID NO 12
<211> LENGTH: 29
<212> TYPE: DNA
<213> ORGANISM: Candida albicans

<400> SEQUENCE: 12
gggctgcagt tatttctttg ctctttcca                                     29

<210> SEQ ID NO 13
<211> LENGTH: 1716
<212> TYPE: DNA
<213> ORGANISM: Candida albicans

<400> SEQUENCE: 13
atggcagaag tattatcatt ggttgacctc gagattcctc aagtcactga taagtattat    60
aaatttgaca ctttaaaaca tttaatctgt cacttgttca agaaaaccag cacagaaact   120
gattcaaatg ttcctatagt aataatattc ccgaccaaca atgatatccc ttcgagaaag   180
actcgatcta ctactaccac caccactact actactacta ctaataccag caagttagac   240
```

```
-continued aatttgccat tcagtgataa atcgttgttg atacaattct tcttcaccca tttgaacata    300
ttgatgattc aaggagagaa ttcggatgag ggaaagttat atcaagaaat aagttcagcc    360
aaagaattat tgacaaatag gatatcacga gttggaaatt ggacaggaac aactcatttt    420
agatactgtc gacatgagaa tgattgtgga ctattgaatc aacattccaa aattgcagga    480
attataccca caatgactta cattctcaat tgtaatgcaa caagatcaga aattgccact    540
aaccaattga tatatttata tcgactcatg atagaggaga ttaattttat tgaattgtta    600
caagatgcat ctacgacaag attatctcag ttgtgttatg ctgtgggaca ttggagtttc    660
cctgctcata atttatcaaa tgacgatttg gtttattgtg tttatttgat gatagattac    720
gctatcaaac aagttgaagg gtttgacaac attcctttga atgaattatt ggcatttata    780
tttattgtta gagataccta taagaatggg aatccgttcc ataatttccg ccacgctgtg    840
gatgttctac aagcttgttt ccattttctt attagattgg gtagtttacc caaattcaag    900
caatttgtcg aggacccgaa attggattac accgaagttc atgacacaca tactgtattg    960
attgccttac aaaacaattc ctccgaggaa aaagcttctc ttaatccaat acaaacatta   1020
gggttattgg ttgcagcatt gggccatgat gtgggccacc caggtacgac aaatgatttc   1080
atgattaaat tcagtgcacc aacggcacta ctttacaatg acagatctgt tcttgaatct   1140
tatcatgcat ctttatttat caataaagtg ttaagaatat gttggccaga tttattaact   1200
tgtacaattg aggaaaaatc agagttaacc attagaagtt tgataatttc ttcgatattg   1260
gccaccgata tgggtgaaca taatgaatat gttaatcggt tgaaatcttt caagacccat   1320
aatgaaattt taaaccatga taacactgtt aaattgattt ctgccttgtt aatcaaatgt   1380
gctgatattt ctaacgtgac gagaccgttg agagtatctg cacaatgggc aatggtttta   1440
tcaagagaat ttgcagaagt tgagttgctc aaatcggtaa tcaaaaaaga tattgatctt   1500
gactttacca aagatttaac ttatgatgat gttccacatg aattacgcga aatacttgaa   1560
atacaacccg atatacataa aggacagata tttttcatca atttattcgc tgagaattta   1620
tttaatagtg ttagtgattt attacctcaa ttgcagtata cttgtgatat tattatggaa   1680
aacaaactat tttggttgga aagagcaaag aaataa                             1716
```

<210> SEQ ID NO 14
<211> LENGTH: 26
<212> TYPE: DNA
<213> ORGANISM: Candida albicans

<400> SEQUENCE: 14

```
ggagttgaaa gtggtttggt caatac                                          26
```

<210> SEQ ID NO 15
<211> LENGTH: 28
<212> TYPE: DNA
<213> ORGANISM: Candida albicans

<400> SEQUENCE: 15

```
ggctggtaga gacttgacca accatttg                                        28
```